US010918697B2

(12) United States Patent
He et al.

(10) Patent No.: US 10,918,697 B2
(45) Date of Patent: *Feb. 16, 2021

(54) CO-ACTIVATION OF MTOR AND STAT3 PATHWAYS TO PROMOTE NEURONAL SURVIVAL AND REGENERATION

(71) Applicant: Children's Medical Center Corporation, Boston, MA (US)

(72) Inventors: Zhigang He, Wellesley, MA (US); Duo Jin, Boston, MA (US); Fang Sun, Boston, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/225,727

(22) Filed: Dec. 19, 2018

(65) Prior Publication Data
US 2019/0125830 A1    May 2, 2019

Related U.S. Application Data

(63) Continuation of application No. 15/696,993, filed on Sep. 6, 2017, now Pat. No. 10,195,247, which is a (Continued)

(51) Int. Cl.
*C12N 15/11*    (2006.01)
*A61K 48/00*    (2006.01)
(Continued)

(52) U.S. Cl.
CPC ...... *A61K 38/1709* (2013.01); *A01K 67/0276* (2013.01); *A61K 9/0085* (2013.01);
(Continued)

(58) Field of Classification Search
CPC .............. A61K 31/713; A61K 31/7088; C07K 14/4703; C12N 15/113; C12N 15/1138
See application file for complete search history.

(56) References Cited

U.S. PATENT DOCUMENTS 9,511,036 B2    12/2016 He et al.
10,195,247 B2 *    2/2019 He ........................ A61K 31/11
(Continued)

FOREIGN PATENT DOCUMENTS

WO    2004/018655 A2    3/2004
WO    2004/075897 A1    9/2004
(Continued)

OTHER PUBLICATIONS

Park et al., "Cellular mechanisms associated with spontaneous and ciliary neurotrophic factor-cAMP-induced survival and axonal regeneration of adult retinal ganglion cells." J Neurosci 24:10806-10815 (2004).

(Continued)

*Primary Examiner* — Terra C Gibbs
(74) *Attorney, Agent, or Firm* — Nixon Peabody LLP; David S. Resnick; Shayne Y. Huff

(57) ABSTRACT

Disclosed herein is a method of promoting sustained survival, sustained regeneration, in a lesioned mature neuron, sustained compensatory outgrowth in a neuron, or combinations thereof. The method comprises contacting the lesioned mature neuron with an effective amount of an inhibitor of PTEN and an effective amount of an inhibitor of SOCS3 to thereby promote survival and/or regeneration and/or compensatory outgrowth of the neuron. Therapeutic methods of treatment of a subject with a neuronal lesion by administration of a therapeutically effective amount of an inhibitor of PTEN and a therapeutically effective amount of an inhibitor of SOCS3, are also disclosed, as are pharmaceutical compositions and devices for use in the methods.

14 Claims, 70 Drawing Sheets

Related U.S. Application Data continuation of application No. 15/342,656, filed on Nov. 3, 2016, now abandoned, which is a continuation of application No. 14/354,694, filed as application No. PCT/US2012/062973 on Nov. 1, 2012, now Pat. No. 9,511,036.

(60) Provisional application No. 61/554,277, filed on Nov. 1, 2011.

(51) Int. Cl.
    | | |
    |---|---|
    | C07H 21/02 | (2006.01) |
    | C07H 21/04 | (2006.01) |
    | A61K 38/17 | (2006.01) |
    | A61K 45/06 | (2006.01) |
    | A61K 9/00 | (2006.01) |
    | A61K 31/4353 | (2006.01) |
    | A61K 31/708 | (2006.01) |
    | A61K 31/7088 | (2006.01) |
    | A61K 33/24 | (2019.01) |
    | A61K 31/444 | (2006.01) |
    | A01K 67/027 | (2006.01) |
    | A61K 31/713 | (2006.01) |
    | A61K 31/11 | (2006.01) |
    | A61K 31/196 | (2006.01) |
    | A61K 31/555 | (2006.01) |
    | A61K 39/395 | (2006.01) |
    | C07K 14/47 | (2006.01) |
    | C12N 9/16 | (2006.01) |

(52) U.S. Cl.
    CPC .......... *A61K 31/11* (2013.01); *A61K 31/196* (2013.01); *A61K 31/4353* (2013.01); *A61K 31/444* (2013.01); *A61K 31/555* (2013.01); *A61K 31/708* (2013.01); *A61K 31/7088* (2013.01); *A61K 31/713* (2013.01); *A61K 33/24* (2013.01); *A61K 39/39533* (2013.01); *A61K 45/06* (2013.01); *C12Y 301/03048* (2013.01); *A01K 2207/30* (2013.01); *A01K 2217/075* (2013.01); *A01K 2217/15* (2013.01); *A01K 2217/206* (2013.01); *A01K 2227/105* (2013.01); *A01K 2267/0356* (2013.01); *C07K 14/4703* (2013.01); *C12N 9/16* (2013.01)

(56) References Cited

U.S. PATENT DOCUMENTS

| | | |
|---|---|---|
| 2002/0142466 A1 | 10/2002 | Flier et al. |
| 2003/0049839 A1 | 3/2003 | Romero-Ortega et al. |
| 2003/0216747 A1 | 11/2003 | Kaplan |
| 2004/0192588 A1 | 9/2004 | Eisenbach-Schwartz et al. |
| 2005/0047996 A1 | 3/2005 | Vogelstein et al. |
| 2005/0118157 A1 | 6/2005 | McMahon et al. |
| 2006/0128014 A1 | 6/2006 | Haggblad et al. |
| 2006/0258994 A1 | 11/2006 | Avery |
| 2007/0292532 A1 | 12/2007 | Woscholski et al. |
| 2009/0148494 A1 | 6/2009 | He et al. |
| 2009/0305333 A1 | 12/2009 | He et al. |
| 2011/0124706 A1 | 5/2011 | He et al. |

FOREIGN PATENT DOCUMENTS

| | | |
|---|---|---|
| WO | 2005/054257 A1 | 6/2005 |
| WO | 2005/097119 A2 | 10/2005 |
| WO | 2007/094755 A2 | 8/2007 |

OTHER PUBLICATIONS

Park et al., "Cytokine-induced SOCS expression is inhibited by cAMP analogue: impact on regeneration in injured retina." Mol Cell Neurosci 41:313-324 (2009).
Park et al., "Promoting axon regeneration in the adult CNS by modulation of the PTEN/mTOR pathway." Science 322:963-966 (2008).
Park et al., "PTEN/mTOR and axon regeneration." Exp Neurol 223:45-50 (2010).
Qin et al., "PP2-048 Regulatory function of SOCS-3 in astrocytes". Abstracts / Cytokine 48:101 (2009).
Qiu et al., "Conditioning injury-induced spinal axon regeneration requires signal transducer and activator of transcription 3 activation." J Neurosci 25:1645-1653 (2005).
Rao et al, "MR imaging of the temporomandibular joint" J. of Neurpchemistry, 83 pp. 1072-1086 (2002).
Rickle et al., "PTEN, Akt, and GSK3 beta signaling in rat primary cortical neuronal cultures following tumor necrosis factor-alpha and trans-4-hydroxy-2-nonenal treatments." Journal of Neuroscience Research, 84(3):596-605 (2006).
Schmid et al., "Bisperoxovanadium compounds are potent PTEN inhibitors." FEBS Letters, 566:35-38 (2004).
Sengupta et al., Regulation of the mTOR complex 1 pathway by nutrients, growth factors, and stress. Mol Cell 40:310-322 (2010).
Smith et al."SOCS3 Deletion promotes optic nerve regeneration in vivo." , Neuron, 64:617-623 (2009).
Sun et al., "Sustained axon regeneratoin induced by a synergy between mTOR and STAT3 dependent pathways" The 13th Spinal Research Network Meeting, Sep. 3, 2011. Retrieved from the Internet: URL:http://www.spinal-research.org/wp-content/uploads/2012/08/Network-Abstract-Booklet-2011-final.pdf#page+16 (retreived Apr. 2, 2015).
Sun et al., "Sustained axon regeneration induced by co-deletion of PTEN and SOCS3." Nature 480:372-375 (2011).
Tripathi et al., "Chronically increased ciliary neurotrophic factor and fibroblast growth factor-2 expression after spinal contusion in rats." J Comp Neurol. 510: 129-144 (2008).
Van Den Brand et al., "Restoring voluntary control of locomotion after paralyzing spinal cord injury." Science 336:1182-1185.
Vemuganti et al., "Suppressor of Cytokine Signaling-3 (SOCS-3) is a neuroprotective gene upregulated after focal ischemia." Abstract from Database Biosis, 2002.
Weibel et al., "Brain-derived neurotrophic factor (BDNF) prevents lesion-induced axonal die-back in young rat optic nerve." Brain Research, 679:249-254 (1995).
Weidner et al., "Spontaneous corticospinal axonal plasticity and functional recovery after adult central nervous system injury", PNAS 98(6): 3513-3518 (2001).
Winzeler et al., "The lipid sulfatide is a novel myelin-associated inhibitor of CNS axon outgrowth." J Neurosci 31:6481-6492 (2011).
Woolf et al., "Peripheral nerve injury triggers central sprouting of myelinated afferents." Nature 355:75-78 (1992).
Yang Peng et al., "Protein tyrosine phosphatase inhibition reduces degeneration of dopaminergic substantia nigra neurons and projections in 6-OHDA treated adult rats." European Journal of Neuroscience, 25(5):1332-1340 (2007).
Zhang et al., "Critical role of PTEN in the coupling between PI3K/AKT and JNK1/2 signaling in ischemic brain injury". FESB Letters, vol. 581, pp. 495-505 (2007).
Zhu et al., "Implication of PTEN in production of reactive oxygen species and neuronal death in in vitro models of stroke and Parkinson's disease." Neurochemistry International, 150(2):507-516 (2007).
Aaronson et al., "A road map for those who don't know JAK-STAT." Science 296:1653-1655 (2002).
Abe et al., "Mammalian target of rapamycin (mTOR) activation increases axonal growth capacity of injured peripheral nerves." J Biol Chem 285: 28034-28043 (2010).
Aoki et al., "The possible role of collateral sprouting in the functional restitution of corticospinal connections after spinal hemisection." Neurosci. Res. 3:617-627 (1986).
Araki et al., Science, 305:1010-1013 (2004). "Increased nuclear NAD biosynthesis and SIRT1 activation prevent axonal degeneration."

(56) References Cited

OTHER PUBLICATIONS

Arevalo et al., "Activation of casein kinase II and inhibition of phosphatase and tensin homologue deleted on chromosome 10 phosphatase by nerve growth factor/p75NTR inhibit glycogen synthase kinase-3beta and stimulate axonal growth." Mol Biol Cell 17(8) 3369-3377 (2006).
Babon et al., "The SOCS box encodes a hierarchy of affinites for Cullin5: Implications for ubiquitin ligase formation and cytokine signalling suppression." J. Mol. Biol., 387:162-174 (2009).
Babon et al., "The Structure of SOCS3 reveals the basis of the extended SH2 domain function and identities an unstructured insertion that regulates stability." Molecular Cell, 22:205-216 (2006).
Baker et al., "SOCS1 and SOCS3 in the control of CNS immunity." Trends in Immunology, 30(8):392-400 (2009.).
Bareyre et al., "In vivo imaging reveals a phase-specific role of STAT3 during central and peripheral nervous system axon regeneration." Proc Natl Acad Sci USA. 108: 6282-6287 (2011).
Bareyre et al., "Long-lasting sprouting and gene expression changes induced by the monoclonal antibody IN-1 in the adult spinal cord" J. Neurosci. 22: 7097-7110 (2002).
Bareyre et al., "The injured spinal cord spontaneously forms a new intraspinal circuit in adult rats." Nat. Neurosci. 7:269-277 (2004).
Bei et al., "Restoration of Visual Function by Enhancing Conduction in Regenerated Axons", Cell, 164(1): 219-232 (2016).
Cafferty et al., "The Nogo-Nogo receptor pathway limits a spectrum of adult CNS axonal growth." J. Neurosci. 26:12242-12250 (2006).
Chang et al., "Phosphatase PTEN in neuronal injury and brain disorders." Trends in Neuroscience, 30(11):581-586 (2007).
Christie et al., "PTEN Inhibitors to Faciliate Intrinsic Regenerative Outgrowth of Afult Peripheral Axons". J of Neuroscience, 30(27):9306-9315 (2010).
Cohen-Cory et al., "Effects of brain-derived neurotrophic factor on optic axon branching and remodelling in vivo." Nature, 378:192-196 (1995).
Croker et al., "Socs3 maintains the specificity of biological responses to cytokine signals during granulocyte and macrophage differentiation." Exp Hematol 36:786-798 (2008).
Ernst et al.,"Acquiring signalling specificity from the cytokine receptor gp130." Trends Genet. 20:23-32 (2004).
Fasnacht et al., "Conditional gp130 deficient mouse mutants." Semin Cell Dev Biol 19:379-384 (2008).
Fawcett. J "Molecular control of brain plasticity and repair." Prog Brain Res 175:501-509 (2009).
Ferguson et al., "Extrinsic and intrinsic determinants of nerve regeneration", Journal of Tissue Engineering, 2(1):1-12 (2013).
Filbin, M. T. "Recapitulate development to promote axonal regeneration: good or bad approach?" Philos Trans R Soc Lond B Biol Sci 361:1565-1574 (2006).
Fitch et al., "CNS injury, glial scars, and inflammation: Inhibitory extracellular matrices and regeneration failure." Exp Neurol 209:294-301 (2008).
Goldstein et al., "Axonal sprouting following incomplete spinal cord injury: an experimental model." J. Spinal Cord Med. 20:200-206 (1997).
Groszer et al., "Negative regulation of neural stem/progenitor cell proliferation by the Pten tumor suppressor gene in vivo." Science 294: 2186-2189 (2001).
Hannila et al., "The role of cyclic AMP signaling in promoting axonal regeneration after spinal cord injury." Exp Neurol 209:321-332 (2008).
Hellal et al., "Microtubule stabilization reduces scarring and causes axon regeneration after spinal cord injury." Science 331: 928-931 (2011).
Hossain-Ibrahim et al., "Analysis of axonal regeneration in the central and peripheral nervous systems of the NG2-deficient mouse", BMC Neuroscience 8(1):1 (2007).

Jin et al., "Restoration of skilled locomotion by sprouting corticospinal axons induced by co-deletion of PTEN and SOCS3", Nature Communications, 6(8074): 1-12 (2015).
Joset et al., "Rostral growth of commissural axons requires the cell adhesion molecule MDGA2." Neural Dev 6, 22 (2011).
Junghans et al.,"Mammalian cadherins and protocadherins: about cell death, synapses and processing." Curr Opin Cell Biol 17: 446-452 (2005).
Koprivica et al.,"EGFR activation mediates inhibition of axon regeneration by myelin and chondroitin sulfate proteoglycans." Science, 310:106-110 (2005).
Lai et al., "Phosphatase and Tensin Homologue Deleted on Choromosome Ten (PTEN) as a Molecular Target in Lung Epithelial Wound Repair", British J Pharmacol, 152: 1172-1184 (2007).
Leibinger et al., "Neuroprotective and axon growth-promoting effects following inflammatory stimulation on mature retinal ganglion cells in mice depend on ciliary neurotrophic factor and leukemia inhibitory factor." J Neurosci 29:14334-14341 (2009).
Leon et al., "Lens injury stimulate axon regeneration in the mature rat optic nerve." The Journal of Neuroscience, 29(12):4615-4626 (2000).
Li et al., "Injured adult retinal axons with Pten and Socs3 co-deletion reform active synapses with suprachiasmatic neurons", Neurobiology of Disease, 73(16): 366-376 (2015).
Li et al., "Regeneration of nigrostriatal dopaminergic axons by degradation of chondroitin sulfate is accompanied by elimination of the fibrotic scar and glia limitans in the lesion site", J Neurosci Res 85(3) 536-547 (2007).
Liu et al., "PTEN deletion enhances the regenerative ability of adult corticospinal neurons." Nature Neurosci. 13:1075-1081 (2010).
Liu et al., "Neuronal intrinsic mechanisms of axon regeneration." Annu Rev Neurosci. 34:131-52 (2011).
Low et al., "Netrin-1 is a novel myelin-associated inhibitor to axon growth." J Neurosci 28:1099-1108 (2008).
Lu et al., "Tyrosine Phosphatase Inhibition Enhances Neurotrophin Potency and Rescues Nigrostraital Neurons in Adult Rats", Experimental Neurology, 178: 259-267 (2002).
Maier et al., "Sprouting, regeneration and circuit formation in the injured spinal cord: factors and activity." Philos Trans R Soc Lond B Biol Sci. 361:1611-1634 (2006).
Miao et al., "Suppressor of Cytokine Signaling-3 suppresses the ability of activated signal transducer and activator of Transcription-3 to stimulate neurite growth in rat primary sensory neurons." The Journal of Neuroscience, 26(3):9512-9519 (2006).
Moore et al., "KLF family members regulate intrinsic axon regeneration ability." Science 326:298-301 (2009).
Mori et al., "CNTF: a putative link between dopamine D2 receptors and neurogenesis." J. Neurosci., 28(23), 5867-5869 (2008).
Mori et al., "Socs3 deficiency in the brain elevates leptin sensitivity and confers resistance to diet-induced obesity." Nat Med 10: 739-743 (2004).
Muller et al., "Exogenous CNTF stimulates axon regeneration of retinal ganglion cells partially via endogenous CNTF" Molecular and Cellular Neuroscience, 41:233-246 (2009).
Nicholson et al., "Suppressor of cytokine signaling-3 preferentially binds to the SHP-2-binding site on the shared cytokine receptor subunit gp130." Proc Natl Acad Sci USA. 97:6493-6498 (2000).
Nix et al., "Axon regeneration requires coordinate activation of p38 and JNK MAPK pathways." Proc Natl Acad Sci USA 108:10738-10743 (2011).
Okada et al., "Conditional ablation of Stat3 or Socs3 discloses a dual role for reactive astrocytes after spinal cord injury." Nature Medicine, 12(7):829-834 (2006).
Missale et al. "Nerve Growth factor abrogates the tumorigenicity of human small cell lung cancer cell lines." Proc. Natl. Sci, 95: 5366-5371 (1998).

* cited by examiner

[PSC vs.PC] AND [PSC vs.SC] AND [PSC vs.WTC]

| Gene ID | PSC/WTC | PC/WTC | SC/WTC |
|---|---|---|---|
| Mdga2: MAM domain containing glycosylphosphatidylinositol anchor 2 | 3.35 | 1.52 | 1.84 |
| Unc5d: unc-5 homolog D (C. elegans) | 3.19 | 1.88 | 1.73 |
| Elavl4: ELAV-like 4 (Hu antigen D) | 2.37 | 1.45 | 1.20 |
| Car3: carbonic anhydrase 3 | 1.99 | 1.13 | 1.22 |
| Zfp40: zinc finger protein 40 | 1.91 | 1.00 | 1.13 |
| Dennd4a: DENN/MADD domain containing 4A | 1.80 | 1.18 | 1.15 |
| Pde7b: phosphodiesterase 7B | 1.80 | 1.13 | 1.13 |
| Slc6a15: solute carrier family 6 (neurotransmitter transporter), member 15 | 1.78 | 1.26 | 1.15 |
| Pcdhb9: protocadherin beta 9 | 1.73 | 1.14 | -1.14 |
| Rheb: RAS-homolog enriched in brain | 1.71 | 1.19 | 1.17 |
| Aga: aspartylglucosaminidase | 1.66 | -1.19 | 1.09 |
| Ranbp9: RAN binding protein 9 | 1.65 | 1.15 | -1.08 |
| Zbtb38: zinc finger and BTB domain containing 38 | 1.65 | 1.16 | 1.12 |
| Tmem106b: transmembrane protein 106B | 1.64 | 1.14 | -1.27 |
| Igf1: insulin-like growth factor 1 | 1.49 | -1.17 | -1.40 |

FIG. 13B

[PSC vs. mC] NOT [PC vs. WTC] NOT [SC vs. WTC]

| GeneID | PSC/WTC | PC/WTC | SC/WTC |
|---|---|---|---|
| Elavl4: ELAV (embryonic lethal, abnormal vision, Drosophila)-like 4 (Hu antigen D) | 2.37 | 1.46 | 1.22 |
| Ubxn2a: UBX domain protein 2A | 2.36 | 1.36 | 1.30 |
| Kcnb2: potassium voltage gated channel, Shab-related subfamily, member 2 | 2.20 | 1.47 | 1.42 |
| Fzd3: frizzled homolog 3 (Drosophila) | 2.09 | 1.31 | 1.25 |
| Odz1: odd Oz/ten-m homolog 1 (Drosophila) | 2.08 | 1.31 | 1.45 |
| Slc2a13: solute carrier family 2 (facilitated glucose transporter), member 13 | 2.04 | 1.34 | 1.37 |
| Esf1: ESF1 nucleolar pre-rRNA processing protein, homolog (S. cerevisiae) | 2.02 | 1.02 | 1.38 |
| Car3: carbonic anhydrase 3 | 1.99 | 1.13 | 1.22 |
| Vstm2a: V-set and transmembrane domain containing 2A | 1.98 | 1.45 | 1.13 |
| Rad50: RAD50 homlog (S. cerevisiae) | 1.97 | 1.14 | 1.37 |
| Dnm1l: dynamin 1-like | 1.97 | 1.47 | 1.28 |
| Serpine2: serine (or cysteine) peptidase inhibitor, clade E, member 2 | 1.96 | 1.45 | 1.43 |
| Lysmd2: LysM, putative peptidoglycan-binding, domain containing 2 | 1.94 | 1.32 | 1.33 |
| Fut8: fucosyltransferase 8 | 1.93 | 1.49 | 1.11 |
| Idi1: isopentenyl-diphosphate delta isomerase | 1.92 | 1.24 | -1.28 |
| Zfp40: zinc finger protein 40 | 1.91 | 1.00 | 1.13 |
| Napb: N-ethylmaleimide sensitive fusion protein attachment protein beta | 1.91 | 1.42 | 1.25 |
| Man2a1: mannosidase 2, alpha 1 | 1.89 | 1.19 | 1.45 |
| Ogfod1: 2-oxoglutarate and iron-dependent oxygenase domain containing 1 | 1.89 | 1.43 | 1.34 |
| Plcb4: phospholipase C, beta 4 | 1.88 | 1.47 | 1.12 |
| Usp46: ubiquitin specific peptidase 46 | 1.88 | 1.31 | 1.29 |
| Gsta4: glutathione S-transferase, alpha 4 | 1.87 | 1.39 | 1.05 |

FIG. 14A

[PSC vs. mC] NOT [PC vs. WTC] NOT [SC vs. WTC]

| GeneID | PSC/WTC | PC/WTC | SC/WTC |
|---|---|---|---|
| Acsl4: acyl-CoA synthetase long-chain family member 4 | 1.87 | 1.40 | 1.36 |
| Rasgef1b: RasGEF domain family, member 1B | 1.86 | 1.46 | 1.36 |
| Unc5c: unc-5 homolog C (C. elegans) | 1.86 | 1.46 | 1.40 |
| Adcy2: adenylate cyclase 2 | 1.84 | 1.31 | 1.45 |
| Lmbrd2: LMBR1 domain containing 2 | 1.84 | 1.28 | 1.24 |
| Tceal8: transcription elongation factor A (SII)-like 8 | 1.84 | 1.39 | -1.19 |
| Lphn2: latrophilin 2 | 1.83 | 1.45 | 1.26 |
| Tmem14a: transmembrane protein 14A | 1.83 | 1.27 | 1.21 |
| Glg1: golgi apparatus protein 1 | 1.83 | 1.49 | 1.32 |
| Gpd2: glycerol phosphate dehydrogenase 2, mitochondrial | 1.82 | 1.29 | 1.41 |
| D1Ertd53e: DNA segment, Chr 1, ERATO Doi 53, expressed | 1.82 | 1.29 | 1.16 |
| B3galnt1: UDP-GalNAc:betaGlcNAc beta 1,3-galactosaminyltransferase, polypeptide 1 | 1.82 | 1.46 | 1.23 |
| Rb1cc1: RB1-inducible coiled-coil 1 | 1.82 | 1.20 | 1.39 |
| Uba6: ubiquitin-like modifier activating enzyme 6 | 1.81 | 1.26 | 1.22 |
| Sp140: Sp140 nuclear body protein | 1.81 | 1.35 | 1.17 |
| Arhgap21: Rho GTPase activating protein 21 | 1.81 | 1.42 | 1.22 |
| Rsf1: remodeling and spacing factor 1 | 1.81 | 1.40 | 1.20 |
| Dennd4a: DENN/MADD domain containing 4A | 1.80 | 1.18 | 1.15 |
| Pde7b: phosphodiesterase 7B | 1.80 | 1.13 | 1.13 |
| Dync1li2: dynein, cytoplasmic 1 light intermediate chain 2 | 1.80 | 1.49 | 1.19 |
| Acp1: acid phosphatase 1, soluble | 1.80 | 1.45 | 1.27 |
| AI851790: expressed sequence AI851790 | 1.80 | 1.49 | 1.47 |

FIG. 14A (cont.)

[PSC vs. mC] NOT [PC vs. WTC] NOT [SC vs. WTC]

| GeneID | PSC/WTC | PC/WTC | SC/WTC |
|---|---|---|---|
| Ube2r2: ubiquitin-conjugating enzyme E2R 2 | 1.80 | 1.41 | 1.47 |
| Grm1: glutamate receptor, metabotropic 1 | 1.80 | 1.48 | 1.37 |
| Vps13a: vacuolar protein sorting 13A (yeast) | 1.80 | 1.47 | 1.11 |
| Gabrb3: gamma-aminobutyric acid (GABA-A) receptor, subunit beta 3 | 1.79 | 1.35 | 1.16 |
| Slc6a15: solute carrier family 6 (neurotransmitter transporter), member 15 | 1.78 | 1.20 | 1.15 |
| Aida: axin interactor, dorsalization associated | 1.77 | 1.44 | 1.49 |
| Slitrk2: SLIT and NTR K-like family, member 2 | 1.77 | 1.49 | 1.19 |
| Sept7: septin 7 | 1.77 | 1.39 | -1.05 |
| Armcx1: armadillo repeat containing, X-linked 1 | 1.77 | 1.41 | 1.30 |
| Slc18a3: solute carrier family 18 (vesicular monoamine), member 3 | 1.76 | 1.33 | 1.15 |
| Trim9: tripartite motif-containing 9 | 1.76 | 1.42 | 1.28 |
| Rabgap1l: RAB GTPase activating protein 1-like | 1.76 | 1.42 | 1.25 |
| Bphl: biphenyl hydrolase-like (serine hydrolase, breast epithelial mucin-associated antigen) | 1.76 | 1.32 | 1.31 |
| Chchd3: coiled-coil-helix-coiled-coil-helix domain containing 3 | 1.75 | 1.46 | 1.11 |
| Nebl: nebulette | 1.75 | 1.46 | 1.26 |
| Usp14: ubiquitin specific peptidase 14 | 1.75 | 1.41 | 1.14 |
| Tspan6: tetraspanin 6 | 1.75 | 1.30 | 1.24 |
| Scn2a1: sodium channel, voltage-gated, type II, alpha 1 | 1.74 | 1.43 | 1.29 |
| Brwd2: bromodomain and WD repeat domain containing 2 | 1.74 | 1.26 | 1.12 |
| Acp1: acid phosphatase 1, soluble | 1.74 | 1.37 | 1.18 |
| Dpp6: dipeptidylpeptidase 6 | 1.74 | 1.41 | 1.18 |
| Zfp9: zinc finger protein 9 | 1.74 | 1.39 | 1.14 |

FIG. 14A (cont.)

[PSC vs. mC] NOT [PC vs. WTC] NOT [SC vs. WTC]

| GeneID | PSC/WTC | PC/WTC | SC/WTC |
|---|---|---|---|
| Sacs: sacsin | 1.73 | 1.48 | 1.20 |
| Sfxn1: sideroflexin 1 | 1.73 | 1.41 | 1.38 |
| Pcdhb9: protocadherin beta 9 | 1.73 | 1.14 | -1.14 |
| Csnk1g3: casein kinase 1, gamma 3 | 1.73 | 1.42 | -1.07 |
| Atxn7l1: ataxin 7-like 1 | 1.72 | 1.20 | 1.40 |
| Asxl3: additional sex combs like 3 (Drosophila) | 1.72 | 1.33 | 1.38 |
| Cugbp2: CUG triplet repeat, RNA binding protein 2 | 1.71 | 1.00 | 1.32 |
| Camk2n2: calcium/calmodulin-dependent protein kinase II inhibitor 2 | 1.71 | 1.45 | 1.46 |
| Pcm1: pericentriolar material 1 | 1.71 | 1.39 | 1.22 |
| Zfp248: zinc finger protein 248 | 1.71 | 1.40 | 1.09 |
| Oxr1: oxidation resistance 1 | 1.71 | 1.39 | 1.11 |
| Eng: endoglin | 1.71 | 1.40 | 1.16 |
| Myo5a: myosin Va | 1.71 | 1.34 | 1.40 |
| Sdad1: SDA1 domain containing 1 | 1.71 | 1.38 | 1.39 |
| Tesk1: testis specific protein kinase 1 | 1.71 | 1.3B | 1.35 |
| Rheb: RAS-homolog enriched in brain | 1.71 | 1.19 | 1.17 |
| Dkk3: dickkopf homolog 3 (Xenopus laevis) | 1.71 | 1.46 | 1.19 |
| Rps6ka5: ribosomal protein S6 kinase, polypeptide 5 | 1.70 | 1.43 | 1.08 |
| Ythdc2: YTH domain containing 2 | 1.70 | 1.29 | 1.15 |
| Acp1: acid phosphatase 1, soluble | 1.70 | 1.31 | 1.14 |
| Acadsb: acyl-Coenzyme A dehydrogenase, short/branched chain | 1.70 | 1.32 | 1.36 |
| Epb4.1l4b: erythrocyte protein band 4.1-like 4b | 1.70 | 1.41 | 1.36 |

*FIG. 14A (cont.)*

[PSC vs. mC] NOT [PC vs. WTC] NOT [SC vs. WTC]

| GeneID | PSC/WTC | PC/WTC | SC/WTC |
|---|---|---|---|
| Acp1: acid phosphatase 1, soluble | 1.70 | 1.30 | 1.19 |
| Nrcam: neuron-glia-CAM-related cell adhesion molecule | 1.70 | 1.38 | 1.21 |
| Ldb2: LIM domain binding 2 | 1.70 | 1.43 | 1.04 |
| Uchl5: ubiquitin carboxyl-terminal esterase L5 | 1.70 | 1.20 | 1.18 |
| Sos1: Son of sevenless homolog 1 (Drosophila) | 1.70 | 1.31 | 1.22 |
| Ppp1r12a: protein phosphatase 1, regulatory (inhibitor) subunit 12A | 1.69 | 1.44 | 1.29 |
| Zfp105: zinc finger protein 105 | 1.69 | 1.49 | 1.29 |
| Pja1: praja1, RING-H2 motif containing | 1.69 | 1.49 | 1.24 |
| Txndc13: thioredoxin domain containing 13 | 1.69 | 1.44 | 1.18 |
| Gdap1: ganglioside-induced differentiation-associated-protein 1 | 1.68 | 1.34 | 1.31 |
| Tbl1xr1: transducin (beta)-like 1X-linked receptor 1 | 1.68 | 1.36 | 1.15 |
| Zc3h12b: zinc finger CCCH-type containing 12B | 1.68 | 1.37 | -1.20 |
| Nkrf: NF-kappaB repressing factor | 1.68 | 1.26 | 1.20 |
| Golga4: golgi autoantigen, golgin subfamily a, 4 | 1.67 | 1.49 | 1.47 |
| Gabrb2: gamma-aminobutyric acid (GABA-A) receptor, subunit beta 2 | 1.67 | 1.42 | 1.18 |
| Wee1: WEE 1 homolog (S. pombe) | 1.67 | 1.35 | 1.10 |
| Xkrx: X Kell blood group precursor related X linked | 1.67 | 1.18 | 1.45 |
| Rnf146: ring finger protein 146 | 1.67 | 1.23 | 1.09 |
| Bex2: brain expressed X-linked 2 | 1.66 | 1.45 | 1.41 |
| Sema3e: sema domain, immunoglobulin domain (Ig), short basic domain, secreted, (semaphorin) 3E | 1.66 | 1.38 | 1.45 |
| Dner: delta/notch-like EGF-related receptor | 1.66 | 1.48 | 1.21 |
| Aga: aspartylglucosaminidase | 1.66 | -1.19 | 1.09 |

*FIG. 14A (cont.)*

[PSC vs. mC] NOT [PC vs. WTC] NOT [SC vs. WTC]

| GeneID | PSC/WTC | PC/WTC | SC/WTC |
|---|---|---|---|
| Atxn7l3: ataxin 7-like 3 | 1.66 | 1.38 | 1.43 |
| Trim37: tripartite motif-containing 37 | 1.66 | 1.39 | -1.12 |
| Gpm6a: glycoprotein m6a | 1.66 | 1.38 | 1.03 |
| Kif21a: kinesin family member 21A | 1.66 | 1.38 | 1.12 |
| Dpysl2: dihydropyrimidinase-like 2 | 1.66 | 1.43 | 1.24 |
| Csnk1e: casein kinase 1, epsilon | 1.66 | 1.35 | 1.18 |
| Ank2: ankyrin 2, brain | 1.66 | 1.39 | 1.45 |
| Sulf2: sulfatase 2 | 1.66 | 1.29 | 1.38 |
| Lphn1: latrophilin 1 | 1.65 | 1.00 | 1.14 |
| Eif2c1: eukaryotic translation initiation factor 2C, 1 | 1.65 | 1.44 | 1.32 |
| Zbtb38: zinc finger and BTB domain containing 38 | 1.65 | 1.16 | 1.12 |
| Ergic2: ERGIC and golgi 2 | 1.66 | 1.25 | -1.11 |
| Frmd3: FERM domain containing 3 | 1.65 | 1.14 | 1.05 |
| P2ry1: purinergic receptor P2Y, G-protein coupled 1 | 1.65 | 1.23 | 1.28 |
| Syt2: synaptotagmin-like 2 | 1.65 | 1.43 | 1.31 |
| Hivep2: human immunodeficiency virus type I enhancer binding protein 2 | 1.66 | 1.46 | 1.45 |
| Ranbp9: RAN binding protein 9 | 1.65 | 1.15 | -1.08 |
| Nrsn1: neurensin 1 | 1.84 | 1.44 | 1.16 |
| Zrsr1: zinc finger (CCCH type), RNA binding motif and serine/arginine rich 1 | 1.64 | 1.30 | -1.10 |
| Ppid: peptidylprolyl isomerase D (cyclophilin D) | 1.64 | 1.44 | -1.16 |
| Nalcn: sodium leak channel, non-selective | 1.64 | 1.45 | 1.11 |
| Tmem106b: transmembrane protein 106B | 1.64 | 1.14 | -1.27 |

*FIG. 14A (cont.)*

[PSC vs. mC] NOT [PC vs. WTC] NOT [SC vs. WTC]

| GeneID | PSC/WTC | PC/WTC | SC/WTC |
|---|---|---|---|
| Slc17a5: solute carrier family 17 (anion/sugar transporter), member 5 | 1.64 | 1.45 | 1.29 |
| Ttc3: tetratricopeptide repeat domain 3 | 1.63 | 1.38 | 1.12 |
| Tspyl2: TSPY-like 2 | 1.63 | 1.49 | 1.05 |
| Scg2: secretogranin II | 1.63 | 1.37 | 1.18 |
| Spin1: spindlin 1 | 1.63 | 1.44 | 1.25 |
| Rap1gds1: RAP1, GTP-GDP dissociation stimulator 1 | 1.63 | 1.39 | 1.46 |
| Arsb: arylsulfatase B | 1.63 | 1.48 | 1.23 |
| Ube2v2: ubiquitin-conjugating enzyme E2 variant 2 | 1.63 | 1.43 | 1.16 |
| Rnf20: ring finger protein 20 | 1.62 | 1.11 | 1.28 |
| Epha7: Eph receptor A7 | 1.62 | 1.35 | 1.16 |
| Ppm2c: protein phosphatase 2C, magnesium dependent, catalytic subunit | 1.62 | 1.30 | -1.08 |
| Ube2v2: ubiquitin-conjugating enzyme E2 variant 2 | 1.62 | 1.40 | 1.16 |
| Nlgn3: neuroligin 3 | 1.62 | 1.46 | 1.03 |
| Ankrd32: ankyrin repeat domain 32 | 1.62 | 1.12 | 1.25 |
| Tceal1: transcription elongation factor A (SII)-like 1 | 1.62 | 1.33 | -1.21 |
| Uaca: uveal autoantigen with coiled-coil domains and ankyrin repeats | 1.62 | 1.41 | 1.31 |
| Setx: senataxin | 1.62 | 1.33 | 1.19 |
| Ldhb: lactate dehydrogenase B | 1.62 | 1.36 | 1.42 |
| Map2k4: mitogen-activated protein kinase kinase 4 | 1.62 | 1.39 | 1.30 |
| Trim32: tripartite motif-containing 32 | 1.62 | 1.30 | 1.08 |
| Usp25: ubiquitin specific peptidase 25 | 1.61 | 1.09 | 1.19 |
| Pts: 6-pyruvoyl-tetrahydropterin synthase | 1.61 | 1.14 | 1.24 |

*FIG. 14A (cont.)*

[PSC vs. mC] NOT [PC vs. WTC] NOT [SC vs. WTC]

| GeneID | PSC/WTC | PC/WTC | SC/WTC |
|---|---|---|---|
| Zhx1: zinc fingers and homeoboxes 1 | 1.61 | 1.27 | 1.06 |
| Usp9x: ubiquitin specific peptidase 9, X chromosome | 1.61 | 1.28 | -1.20 |
| Ppp1r7: protein phosphatase 1, regulatory (inhibitor) subunit 7 | 1.61 | 1.36 | -1.10 |
| Zmynd11: zinc finger, MYND domain containing 11 | 1.60 | 1.33 | 1.06 |
| Spred1: sprouty protein with EVH-1 domain 1, related sequence | 1.60 | 1.36 | 1.37 |
| Fhl1: four and a half LIM domains 1 | 1.60 | 1.40 | 1.33 |
| Foxj3: forkhead box J3 | 1.60 | 1.3B | 1.25 |
| Pggt1b: protein geranylgeranyltransferase type 1, beta subunit | 1.60 | 1.23 | 1.23 |
| Pja2: praja 2, RING-H2 motif containing | 1.60 | 1.39 | -1.09 |
| Exoc2: exocyst complex component 2 | 1.80 | 1.21 | -1.17 |
| Grid2: glutamate receptor, ionotropic, delta 2 | 1.60 | 1.42 | 1.36 |
| Pcyox1: prenylcysteine oxidase 1 | 1.60 | 1.20 | 1.18 |
| Dnanc3: dynein, axonemal, heavy chain 3 | 1.60 | 1.13 | 1.46 |
| Kifap3: kinesin-associated protein 3 | 1.60 | 1.25 | 1.00 |
| Spire1: spire homolog 1 (Drosophila) | 1.60 | 1.22 | 1.22 |
| Ppt1: palmitoyl-protein thioesterase 1 | 1.60 | 1.25 | 1.20 |
| Mapt: microtubule-associated protein tau | 1.60 | 1.32 | 1.16 |
| Phc3: polyhomeotic-like 3 (Drosophila) | 1.60 | 1.24 | -1.27 |
| Ccno: cyclin O | -1.60 | -1.41 | -1.23 |
| Olfr148: olfactory receptor 148 | -1.66 | -1.33 | -1.26 |
| Atad4: ATPase family, AAA domain containing 4 | -1.68 | -1.30 | -1.21 |
| Cldn13: claudin 13 | -1.69 | -1.46 | -1.24 |

FIG. 14A (cont.)

[PSC vs. mC] NOT [PC vs. WTC] NOT [SC vs. WTC]

| GeneID | PSC/WTC | PC/WTC | SC/WTC |
|---|---|---|---|
| Ptges2: prostaglandin E synthase 2 | -1.70 | -1.43 | -1.49 |
| Tbc1d24: TBC1 domain family, member 24 | -1.71 | -1.36 | -1.24 |
| Olfr313: olfactory receptor 313 | -1.72 | -1.27 | 1.17 |
| Jam2: junction adhesion molecule 2 | -1.79 | -1.47 | -1.29 |
| Pepd: peptidase D | -1.79 | -1.30 | -1.28 |
| Mrps10: mitochondrial ribosomal protein S10 | -1.85 | -1.44 | -1.46 |

FIG. 14A (cont.)

[PSC vs.WTC] NOT [PC vs.WTC] NOT [SC vs.WTC] Top Function Clusters

| Annotation Cluster 1: Enrichment Score: 3.08 | Count | % | P Value |
|---|---|---|---|
| neuron projection | 12 | 6.7 | 0.000 |
| axon | 7 | 3.9 | 0.000 |
| dendrite | 6 | 3.4 | 0.003 |
| cell soma | 6 | 3.4 | 0.004 |
| cell projection | 13 | 7.3 | 0.006 |

| Annotation Cluster 2: Enrichment Score: 1.94 | Count | % | P Value |
|---|---|---|---|
| ion binding | 54 | 30.3 | 0.002 |
| metal ion binding | 52 | 29.2 | 0.004 |
| cation binding | 52 | 29.2 | 0.004 |
| metal-binding | 39 | 21.9 | 0.005 |
| zinc | 28 | 15.7 | 0.015 |
| zinc ion binding | 30 | 16.9 | 0.022 |
| transition metal ion binding | 34 | 19.1 | 0.043 |
| zinc-finger | 16 | 9.0 | 0.152 |

| Annotation Cluster 3: Enrichment Score: 1.90 | Count | % | P Value |
|---|---|---|---|
| cytoskeleton | 21 | 11.8 | 0.002 |

FIG. 14B

[PSC vs.WTC] NOT [PC vs.WTC] NOT [SC vs.WTC] Top Function Clusters

| | Count | % | P Value |
|---|---|---|---|
| intracellular non-membrane-bounded organelle | 29 | 16.3 | 0.006 |
| non-membrane-bounded organelle | 29 | 16.3 | 0.006 |
| cytoskeletal part | 15 | 8.4 | 0.010 |
| microtubule cytoskeleton | 9 | 5.1 | 0.051 |
| cytoskeleton | 10 | 5.6 | 0.095 |

Annotation Cluster 4: Enrichment Score: 1.77

| | Count | % | P Value |
|---|---|---|---|
| ubl conjugation pathway | 13 | 7.3 | 0.002 |
| cellular macromolecule catabolic process | 14 | 7.9 | 0.003 |
| cellular protein catabolic process | 13 | 7.3 | 0.003 |
| protein catabolic process | 13 | 7.3 | 0.003 |
| thiolester hydrolase activity | 6 | 3.4 | 0.004 |
| ubiquitin thiolesterase activity | 5 | 2.8 | 0.005 |
| macromolecule catabolic process | 14 | 7.9 | 0.005 |
| modification-dependent macromolecule catabolic process | 12 | 6.7 | 0.005 |
| modification-dependent protein catabolic process | 12 | 6.7 | 0.005 |
| proteolysis involved in cellular protein catabolic process | 12 | 6.7 | 0.007 |
| Peptidase C19, ubiquitin carboxyl-terminal hydrolase 2, conserved site | 4 | 2.2 | 0.013 |
| Peptidase C19, ubiquitin carboxyl-terminal hydrolase 2 | 4 | 2.2 | 0.015 |

*FIG. 14B (cont.)*

| [PSC vs.WTC] NOT [PC vs.WTC] NOT [SC vs.WTC] Top Function Clusters | | | |
|---|---|---|---|
| ligase | 8 | 4.5 | 0.019 |
| thiol protease | 5 | 2.8 | 0.026 |
| ubiquitin-dependent protein catabolic process | 5 | 2.8 | 0.035 |
| cysteine-type peptidase activity | 5 | 2.8 | 0.050 |
| proteolysis | 14 | 7.9 | 0.119 |
| Protease | 6 | 3.4 | 0.514 |
| peptidase activity, acting on L-amino acid peptides | 6 | 3.4 | 0.682 |
| peptidase activity | 6 | 3.4 | 0.718 |
| Annotation Cluster 5: Enrichment Score: 17.1 | Count | % | P Value |
| membrane fraction | 11 | 6.2 | 0.017 |
| cell fraction | 12 | 6.7 | 0.019 |
| insoluble fraction | 11 | 6.2 | 0.021 |
| synaptosome | 4 | 2.2 | 0.022 |

*FIG. 14B (cont.)*

[PSC vs. PC] AND [PSC vs. WTC] NOT [PSC vs. SC]

| Gene ID | PSC/WTC | PC/WTC | SC/WTC |
|---|---|---|---|
| Sprr1a: small proline-rich protein 1A | 2.42 | -1.64 | 4.38 |
| Emr1: EGF-like module containing mucin-like, hormone receptor-like sequence 1 | 2.22 | -1.48 | 3.37 |
| Ms4a7: membrane-spanning 4-domains, subfamily A, member 7 | 3.09 | -1.03 | 4.18 |
| Sfrp1: secreted frizzled-related protein 1 | 9.19 | 3.41 | 20.66 |
| Gnal: guanine nucleotide binding protein, alpha stimulating, olfactory type | 3.80 | 1.39 | 3.08 |
| Vwa5a: von Willebrand factor A domain containing 5A | 2.44 | 1.05 | 2.43 |
| Ifnar2: interferon (alpha and beta) receptor 2 | 1.79 | -1.28 | 2.09 |
| Zfp697: zinc finger protein 697 | 3.76 | 1.77 | 4.01 |
| Rian: RNA imprinted and accumulated in nucleus | 3.14 | 1.51 | 2.50 |
| Anxa5: annexin A5 | 2.04 | -1.02 | 2.39 |
| Dusp6: dual specificity phosphatase 6 | 1.65 | -1.25 | 1.81 |
| S100a10: S100 calcium binding protein A10 (calpactin) | 2.17 | 1.07 | 3.37 |
| Tmem47: transmembrane protein 47 | 3.18 | 1.58 | 2.40 |
| Esf1: ESF1, nucleolar pre-rRNA processing protein, homolog (S. cerevisiae) | 2.02 | 1.02 | 1.36 |
| Mgat4c: mannosyl (alpha-1,3-)-glycoprotein beta-1,4-N-acetylglucosaminyltransferase, isozyme C (putative) | 3.75 | 1.92 | 2.60 |
| Chl1: cell adhesion molecule with homology to L1CAM | 2.09 | 1.08 | 2.48 |
| Tmem176a: transmembrane protein 176A | 1.85 | -1.01 | 2.72 |
| Ccdc88a: coiled coil domain containing 88A | 3.18 | 1.73 | 2.67 |
| Antxr1: anthrax toxin receptor 1 | 1.94 | 1.07 | 1.66 |
| Slc17a6: solute carrier family 17 (sodium-dependent inorganic phosphate cotransporter), member 8 | 6.54 | 3.82 | 8.73 |
| Stmn2: stathmin-like 2 | 3.86 | 2.16 | 4.47 |

*FIG. 15B*

[PSC vs. PC] AND [PSC vs. WTC] NOT [PSC vs. SC]

| Gene ID | PSC/WTC | PC/WTC | SC/WTC |
|---|---|---|---|
| Klf6: Kruppel-like factor 6 | 2.16 | 1.22 | 2.08 |
| Penk1: preproenkephalin 1 | 2.41 | 1.38 | 2.99 |
| Lix1: limb expression 1 homolog (chicken) | 2.04 | 1.17 | 2.40 |
| Rad50: RAD50 homolog (S. cerevisiae) | 1.17 | 1.14 | 1.37 |
| Myadm: myeloid-associated differentiation marker | 1.82 | 1.12 | 2.68 |
| Iqgap2: IQ motif containing GTPase activating protein 2 | 2.34 | 1.37 | 1.54 |
| Fut9: fucosyltransferase 9 | 2.35 | 1.42 | 2.05 |
| Rock2: Rho-associated coiled-coil containing protein kinase 2 | 2.38 | 1.42 | 1.67 |

FIG. 15B (cont.)

[PSC vs.SC] AND [PSC vs. WTC] NOT [PSC vs.PC]

| Gene ID | PSC/WTC | PC/WTC | SC/WTC |
|---|---|---|---|
| Nlrp4f: NLR family, pyrin domain containing 4F | 2.47 | 1.62 | -1.44 |
| Vmn2r122: vomeronasal 2, receptor, 122 | 2.43 | 1.53 | -1.26 |
| Psg17: pregnancy specific glycoprotein 17 | 2.37 | 3.80 | -1.27 |
| Casd1: CAS1 domain containing 1 | 2.00 | 1.54 | -1.49 |
| Pcdhb19: protocadherin beta 19 | 2.03 | 1.87 | -1.40 |
| Unc13c: unc-13 homolog C (C. elegans) | 3.02 | 4.10 | 1.10 |
| Hmgcs1: 3-hydroxy-3-methylglutaryl-Coenzyme A synthase 1 | 2.36 | 1.87 | -1.09 |
| Gabrb2: gamma-aminobutyric acid (GABA-A) receptor, subunit beta 2 | 2.73 | 1.88 | 1.07 |
| Fat3: FAT tumor suppressor homolog 3 (Drosophila) | 3.60 | 2.83 | 1.42 |
| Idi1: isopentenyl-diphosphate delta isomerase | 1.92 | 1.24 | -1.28 |
| Smarca1: SWI/SNF related, matrix associated, actin dependent regulator of chromatin, subfamily a, member 1 | 2.37 | 1.78 | -1.01 |
| Slitrk6: SLIT and NTRK-like family, member 6 | 2.48 | 2.22 | 1.06 |
| Flrt3: fibronectin leucine rich transmembrane protein 3 | 3.06 | 1.94 | 1.39 |
| Tcea8: transcription elongation factor A (SII)-like 8 | 1.84 | 1.39 | -1.19 |
| Ugcg: UDP-glucose ceramide glucosyltransferase | 2.43 | 1.88 | 1.13 |
| Kcnab1: potassium voltage-gated channel, shaker-related subfamily, beta member 1 | 2.23 | 1.88 | 1.05 |
| Plch1: phospholipase C, eta 1 | 1.88 | 1.63 | -1.13 |
| Gad2: glutamic acid decarboxylase 2 | 4.20 | 3.21 | 2.01 |
| Zc3h6: zinc finger CCCH type containing 6 | 2.01 | 2.19 | -1.02 |
| Lrrn3: leucine rich repeat protein 3, neuronal | 2.63 | 1.83 | 1.28 |
| Hpgd: hydroxyprostaglandin dehydrogenase 15 (NAD) | 3.73 | 3.57 | 1.83 |
| Psd3: pleckstrin and Sec7 domain containing 3 | 2.50 | 2.32 | 1.23 |

FIG. 15D

[PSC vs.SC] AND [PSC vs. WTC] NOT [PSC vs.PC]

| Gene ID | PSC/WTC | PC/WTC | SC/WTC |
|---|---|---|---|
| Phc3: polyhomeotic-like 3 (Drosophila) | 1.60 | 1.24 | -1.27 |
| Tm6sf1: transmembrane 6 superfamily member 1 | 1.83 | 1.55 | -1.11 |
| Elovl6: ELOVL family member 6, elongation of long chain fatty acids (yeast) | 2.08 | 1.68 | 1.03 |
| Zc3h12b: zinc finger CCCH-type containing 12B | 1.68 | 1.37 | -1.20 |
| Pcsk1: proprotein convertase subtilisin/kexin type 1 | 2.78 | 2.28 | 1.38 |
| Ccnb1: cyclin B1 | 2.67 | 2.06 | 1.33 |
| Npnt: nephronectin | 2.55 | 2.02 | 1.28 |
| Fbxw7: F-box and WD-40 domain protein 7, archipelago homolog (Drosophila) | 1.79 | 1.53 | -1.12 |
| Cacna2d1: calcium channel, voltage-dependent, alpha2/delta subunit 1 | 3.14 | 2.68 | 1.58 |
| Zmat4: zinc finger, matrin type 4 | 2.52 | 2.00 | 1.27 |
| Macrod2: MACRO domain containing 2 | 2.39 | 2.12 | 1.21 |
| Tceal1: transcription elongation factor A (SII)-like 1 | 1.62 | 1.33 | -1.21 |
| Pcdhb9: protocadherin beta 9 | 1.73 | 1.14 | -1.14 |
| Usp24: ubiquitin specific peptidase 24 | 2.96 | 2.48 | 1.51 |
| Scoc: short coiled-coil protein | 2.71 | 2.20 | 1.39 |
| Cbln2: cerebellin 2 precursor protein | 3.56 | 3.59 | 1.83 |
| Rnmt: RNA (guanine-7-) methyltransferase | 1.82 | 1.59 | -1.06 |
| Usp9x: ubiquitin specific peptidase 9, X chromosome | 1.61 | 1.28 | -1.20 |
| Cacng2: calcium channel, voltage-dependent, gamma subunit 2 | 4.49 | 3.61 | 2.34 |
| Impad1: inositol monophosphatase domain containing 1 | 1.96 | 1.80 | 1.03 |
| Rif1: Rap1 interacting factor 1 homolog (yeast) | 1.82 | 1.36 | -1.05 |
| Fgf14: fibroblast growth factor 14 | 3.77 | 2.88 | 1.98 |

*FIG. 15D (cont.)*

[PSC vs.SC] AND [PSC vs. WTC] NOT [PSC vs.PC]

| Gene ID | PSC/WTC | PC/WTC | SC/WTC |
|---|---|---|---|
| Nap1l2: nucleosome assembly protein 1-like 2 | 2.84 | 2.28 | 1.49 |
| Prkar2b: protein kinase, cAMP dependent regulatory, type II beta | 2.32 | 2.12 | 1.22 |
| Nxf2: nuclear transport factor 2-like export factor 2 | 2.04 | 1.81 | 1.07 |
| Vps41: vacuolar protein sorting 41 (yeast) | 1.69 | 1.50 | -1.13 |
| Armcx5: armadillo repeat containing, X-linked 5 | 2.18 | 1.81 | 1.15 |
| Hlf: hepatic leukemia factor | 1.98 | 1.56 | 1.04 |
| Gabra3: gamma-aminobutyric acid (GABA-A) receptor, subunit alpha 3 | 2.35 | 1.80 | 1.25 |
| Galnt13: UDP-N-acetyl-alpha-D-galactosamine:polypeptide N-acetylgalactosaminyltransferase 13 | 2.30 | 1.63 | 1.22 |
| Exoc2: exocyst complex component 2 | 1.60 | 1.27 | -1.17 |
| Mgat4a: mannoside acetylglucosaminyltransferase 4, isoenzyme A | 2.89 | 1.92 | 1.54 |
| Zkscan16: zinc finger with KRAB and SCAN domains 16 | 2.46 | 1.98 | 1.31 |
| Nap1l3: nucleosome assembly protein 1-like 3 | 2.41 | 1.77 | 1.29 |
| Ttc26: tetratricopeptide repeat domain 28 | 1.99 | 1.51 | 1.07 |
| Trim37: tripartite motif-containing 37 | 1.66 | 1.39 | -1.12 |
| Csnk1g3: casein kinase 1, gamma 3 | 1.73 | 1.42 | -1.07 |
| Pax6: paired box gene 6 | 2.70 | 1.67 | 1.46 |
| Maoa: monoamine oxidase A | 2.25 | 2.78 | 1.22 |
| Tet1: tet oncogene 1 | 1.68 | 1.51 | -1.11 |
| Ergic2: ERGIC and golgi 2 | 1.86 | 1.25 | -1.11 |
| Gabra1: gamma-aminobutyric acid (GABA-A) receptor, subunit alpha 1 | 1.80 | 1.50 | -1.02 |
| Pcdhb20: protocadherin beta 20 | 2.22 | 1.52 | 1.22 |
| Gucy1b3: guanylate cyclase 1, soluble, beta 3 | 1.67 | 1.43 | -1.09 |

FIG. 15D (cont.)

[PSC vs.SC] AND [PSC vs. WTC] NOT [PSC vs.PC]

| Gene ID | PSC/WTC | PC/WTC | SC/WTC |
|---|---|---|---|
| Scd1: stearoyl-Coenzyme A desaturase 1 | 1.73 | 1.53 | -1.05 |
| Inpp5f: inositol polyphosphate-5-phosphatase F | 3.00 | 2.03 | 1.65 |
| Cdc42bpa: CDC42 binding protein kinase alpha | 1.84 | 1.63 | 1.07 |
| Zdbf2: zinc finger, DBF-type containing 2 | 2.08 | 1.97 | 1.15 |
| Fstl5: follistatin-like 5 | 1.99 | 1.57 | 1.10 |
| Rcn2: reticulocalbin 2 | 1.82 | 1.57 | 1.01 |
| Sobp: sine oculis-binding protein homolog (Drosophila) | 3.37 | 2.92 | 1.87 |
| Slit2: slit homolog 2 (Drosophila) | 2.22 | 1.96 | 1.23 |
| Gsta4: glutathione S-transferase, alpha 4 | 1.87 | 1.39 | 1.05 |
| Ttll7: tubulin tyrosine ligase-like family, member 7 | 2.22 | 1.96 | 1.24 |
| Gpr85: G protein-coupled receptor 85 | 1.77 | 1.29 | -1.01 |
| Stard4: StAR-related lipid transfer (START) domain containing 4 | 1.82 | 1.70 | 1.02 |
| Dnajc13: DnaJ (Hsp40) homolog, subfamily C, member 13 | 1.75 | 1.65 | -1.02 |
| Txndc10: thioredoxin domain containing 10 | 2.17 | 1.74 | 1.22 |
| Cpeb2: cytoplasmic polyadenylation element binding protein 2 | 1.89 | 1.70 | 1.07 |
| Spock3: sparc/osteonectin, cwcv and kazal-like domains proteoglycan 3 | 2.80 | 2.47 | 1.50 |
| Ppp1r7: protein phosphatase 1, regulatory (inhibitor) subunit 7 | 1.61 | 1.36 | -1.10 |
| Hecw1: HECT, C2 and WW domain containing E3 ubiquitin protein ligase 1 | 2.37 | 2.17 | 1.35 |
| Rfesd: Rieske (Fe-S) domain containing | 1.88 | 1.63 | 1.07 |
| Slc4a3: solute carrier family 4 (anion exchanger), member 3 | 1.71 | 2.61 | -1.03 |
| Ppm2c: protein phosphatase 2C, magnesium dependent, catalytic subunit | 1.82 | 1.30 | -1.08 |
| Pja2: praja 2, RING-H2 motif containing | 1.80 | 1.38 | -1.09 |

FIG. 15D (cont.)

[PSC vs SC] AND [PSC vs. WTC] NOT [PSC vs.PC]

| Gene ID | PSC/WTC | PC/WTC | SC/WTC |
|---|---|---|---|
| Vstm2a: V-set and transmembrane domain containing 2A | 1.98 | 1.45 | 1.13 |
| Gria3: glutamate receptor, ionotropic, AMPA3 (alpha 3) | 2.52 | 2.18 | 1.44 |
| Cep170: centrosomal protein 170 | 2.71 | 1.93 | 1.55 |
| Dnm3: dynamin 3 | 2.38 | 1.65 | 1.36 |
| Fut8: fucosyltransferase 8 | 1.93 | 1.49 | 1.11 |
| Synpr: synaptoporin | 1.94 | 1.69 | 1.11 |
| Pde4d: phosphodiesterase 4D, cAMP specific | 2.51 | 2.16 | 1.44 |
| Tmeff1: transmembrane protein with EGF-like and two follistatin-like domains 1 | 2.28 | 2.01 | 1.31 |
| Utrn: utrophin | 2.68 | 2.41 | 1.55 |
| Cask: calcium/calmodulin-dependent serine protein kinase (MAGUK family) | 1.84 | 1.40 | 1.06 |
| Jarid1d: jumonji, AT rich interactive domain 1D (Rbp2 like) | 1.87 | 1.88 | 1.09 |
| Ddef1: development and differentiation enhancing | 1.93 | 1.62 | 1.12 |
| Sv2a: synaptic vesicle glycoprotein 2 a | 2.01 | 1.76 | 1.17 |
| Cacng3: calcium channel, voltage-dependent, gamma subunit 3 | 1.87 | 2.02 | 1.14 |
| Glrb: glycine receptor, beta subunit | 1.96 | 1.55 | 1.14 |
| Cux2: cut-like homeobox 2 | 2.15 | 1.58 | 1.26 |
| Slc4a10: solute carrier family 4, sodium bicarbonate cotransporter-like, member 10 | 1.61 | 1.29 | -1.07 |
| Grin2a: glutamate receptor, ionotropic, NMDA2A (epsilon 1) | 3.19 | 2.93 | 1.87 |
| Fgf13: fibroblast growth factor 13 | 1.81 | 1.59 | 1.06 |
| Magi2: membrane associated guanylate kinase, WW and PDZ domain containing 2 | 2.08 | 1.83 | 1.23 |
| Kifap3: kinesin-associated protein 3 | 1.60 | 1.25 | -1.06 |
| Fnbp1l: formin binding protein 1-like | 2.78 | 2.64 | 1.64 |

*FIG. 15D (cont.)*

[PSC vs.SC] AND [PSC vs. WTC] NOT [PSC vs.PC]

| Gene ID | PSC/WTC | PC/WTC | SC/WTC |
|---|---|---|---|
| Six6: sine oculis-related homeobox 6 homolog (Drosophila) | 1.70 | 1.27 | 1.00 |
| Fgd6: FYVE, RhoGEF and PH domain containing 6 | 2.00 | 1.74 | 1.18 |
| Gpr165: G protein-coupled receptor 165 | 1.89 | 1.98 | 1.12 |
| Wnk3: WNK lysine deficient protein kinase 3 | 2.40 | 1.95 | 1.42 |
| Nccab1: N-terminal EF-hand calcium binding protein 1 | 3.05 | 2.18 | 1.81 |
| Plcb4: phospholipase C, beta 4 | 1.88 | 1.47 | 1.12 |
| Anubl1: AN1, ubiquitin-like, homolog (Xenopus laevis) | 2.06 | 2.01 | 1.23 |
| Tcfap2b: transcription factor AP-2 beta | 2.67 | 2.21 | 1.60 |
| Reps1: RalBP1 associated Eps domain containing protein | 1.60 | 1.44 | -1.04 |
| Chn1: chimerin (chimaerin) 1 | 2.09 | 1.76 | 1.25 |
| Ppfia2: protein tyrosine phosphatase, receptor type, f polypeptide (PTPRF), interacting protein (liprin), alpha 2 | 1.68 | 1.38 | 1.00 |
| Irs1: insulin receptor substrate 1 | 2.00 | 1.76 | 1.20 |
| Gprc5b: G protein-coupled receptor, family C, group 5, member B | 2.08 | 1.82 | 1.25 |
| Meis2: Meis homeobox 2 | 2.16 | 1.91 | 1.30 |
| Kcnip1: Kv channel-interacting protein 1 | 3.63 | 3.05 | 2.19 |
| Ptx3: pentraxin related gene | 2.26 | 1.94 | 1.37 |
| Gad1: glutamic acid decarboxylase 1 | 2.05 | 1.82 | 1.24 |
| Lu7p2: leucine zipper protein 2 | 1.99 | 2.15 | 1.21 |
| Tspan12: tetraspanin 12 | 2.11 | 2.25 | 1.28 |
| Reps2: RALBP1 associated Eps domain containing protein 2 | 2.39 | 1.92 | 1.45 |
| Pkia: protein kinase inhibitor, alpha | 1.93 | 1.61 | 1.17 |
| Cdh8: cadherin 8 | 1.70 | 1.56 | 1.03 |

*FIG. 15D (cont.)*

[PSC vs. SC] AND [PSC vs. WTC] NOT [PSC vs. PC]

| Gene ID | PSC/WTC | PC/WTC | SC/WTC |
|---|---|---|---|
| Pde4b: phosphodiesterase 4B, cAMP specific | 2.80 | 2.19 | 1.70 |
| Ppm1k: protein phosphatase 1K (PP2C domain containing) | 2.21 | 1.74 | 1.35 |
| Itfg1: integrin alpha FG-GAP repeat containing 1 | 1.63 | 1.47 | 1.00 |
| Edil3: EGF-like repeats and discoidin 1-like domains 3 | 1.95 | 1.74 | 1.20 |
| Ppm1l: protein phosphatase 1 (formerly 2C)-like | 1.62 | 1.26 | -1.01 |
| Ldb2: LIM domain binding 2 | 1.70 | 1.43 | 1.04 |
| Chst9: carbohydrate (N-acetylgalactosamine 4-0) sulfotransferase 9 | 1.97 | 1.85 | 1.21 |
| Slc5a3: solute carrier family 5 (inositol transporters), member 3 | 1.66 | 1.45 | 1.02 |
| Vps13a: vacuolar protein sorting 13A (yeast) | 1.80 | 1.47 | 1.11 |
| Zfhx4: zinc finger homeodomain 4 | 2.37 | 2.23 | 1.46 |
| Hnt: neurotrimin | 1.64 | 1.26 | 1.01 |
| Pcdh10: protocadherin 10 | 2.88 | 2.66 | 1.79 |
| Magee1: melanoma antigen, family E, 1 | 1.68 | 1.59 | 1.05 |
| Robo2: roundabout homolog 2 (Drosophila) | 2.62 | 2.31 | 1.62 |
| Gpm6a: glycoprotein m6a | 1.66 | 1.38 | 1.03 |
| Dock3: dedicator of cyto-kinesis 3 | 2.62 | 2.10 | 1.64 |
| Atp6ap2: ATPase, H+ transporting, lysosomal accessory protein 2 | 1.60 | 1.37 | 1.00 |

FIG. 15D (cont.)

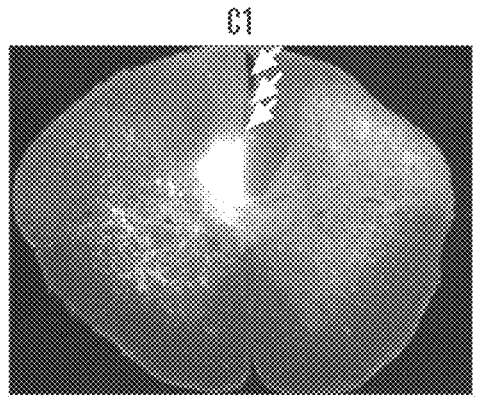
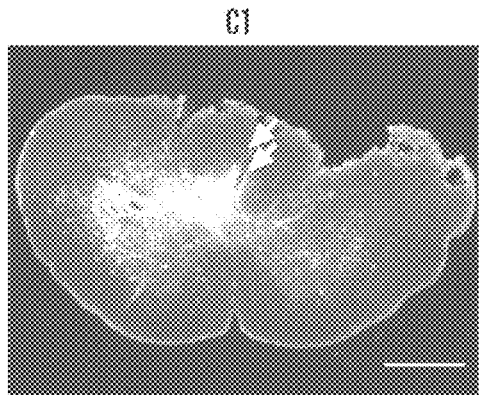
FIG. 25A          FIG. 25B
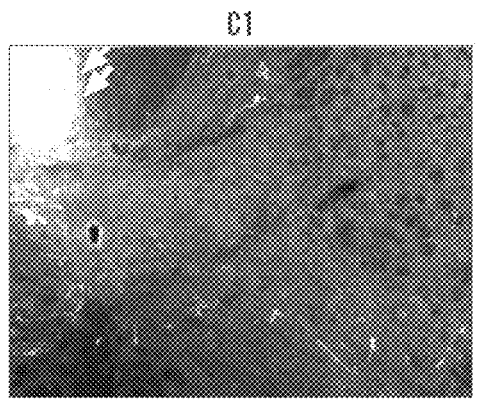
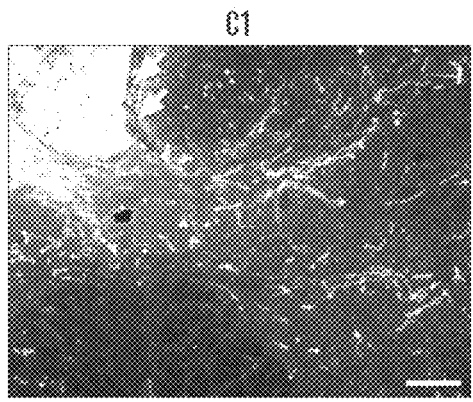
FIG. 25C          FIG. 25D
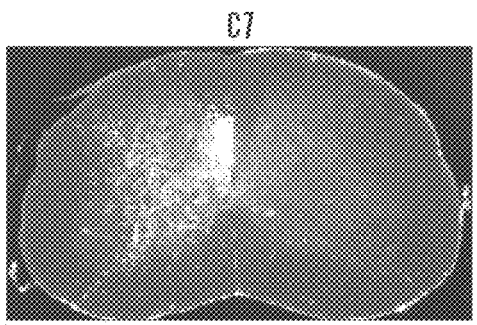
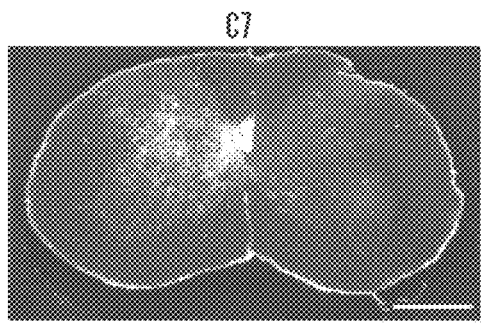
FIG. 25E          FIG. 25F

CO-ACTIVATION OF MTOR AND STAT3 PATHWAYS TO PROMOTE NEURONAL SURVIVAL AND REGENERATION

CROSS REFERENCE TO RELATED APPLICATIONS

This Application is a Continuation of U.S. application Ser. No. 15/696,993, filed on Sep. 6, 2017, now U.S. Pat. No. 10,195,247 issued Feb. 5, 2019, which is a Continuation of U.S. application Ser. No. 15/342,656, filed on Nov. 3, 2016, now abandoned, which is a Continuation of U.S. application Ser. No. 14/354,694, filed on Apr. 28, 2014, now a U.S. Pat. No. 9,511,036 issued on Dec. 6, 2016, which is a 35 U.S.C. § 371 National Phase Entry Application of International Application No. PCT/US12/062973, filed on Nov. 1, 2012, which claims benefit under 35 U.S.C. § 119(e) of U.S. Provisional Application No. 61/554,277, filed on Nov. 1, 2011, the contents of each of which are incorporated herein by reference in their entireties.

GOVERNMENTAL SUPPORT

This invention was made with government support under Grant nos. EY021342 and EY021526 awarded by The National Institutes of Health. The government has certain rights in the invention.

FIELD OF THE INVENTION

The present invention relates to the field of neural regeneration.

BACKGROUND OF THE INVENTION

Axon regeneration failure accounts for permanent functional deficits following neuronal injury in adult mammals. However, the underlying mechanisms that control axon regeneration in the adult CNS and PNS remain elusive. A formidable challenge in neural repair in the adult nervous system is the long distances that regenerating axons often need to travel in order to reconnect with their targets. Thus, a sustained capacity for axon regeneration is critical for achieving functional restoration. Although deletion of either Phosphatase and tensin homolog (PTEN), a negative regulator of mammalian target of rapamycin (mTOR), or suppressor of cytokine signaling 3 (SOCS3), a negative regulator of Janus kinase/signal transducers and activators of transcription (JAK/STAT) pathway, in adult retinal ganglion cells (RGCs) individually promoted significant optic nerve regeneration, such re-growth tapered off around two weeks after the crush injury[1,2]. The identification of factors and techniques that promote sustained regeneration to damaged neurons is critical for the development of successful therapeutics.

SUMMARY

One aspect of the invention relates to a method of promoting sustained survival in a lesioned mature neuron, sustained regeneration in a lesioned mature neuron, sustained compensatory outgrowth in a mature neuron, or a combination thereof. The method comprises, contacting the neuron with an effective amount of an inhibitor of PTEN and an effective amount of an inhibitor of SOCS3 to thereby promote sustained survival, sustained regeneration, and/or sustained compensatory outgrowth of the neuron. In one embodiment, the lesioned mature neuron is the result of an acute injury. In one embodiment, the acute injury is selected from the group consisting of crush, severing, and acute ischemia. In one embodiment, the lesioned mature neuron is the result of chronic neurodegeneration. In one embodiment of the aforementioned inventions, contacting first occurs within 24 hours of the injury. In one embodiment of the aforementioned inventions, contacting first occurs within 3 days of the injury. In one embodiment of the aforementioned inventions, contacting first occurs within 6 days of the injury. In one embodiment of the aforementioned inventions, contacting is continued for a period of time selected from the group consisting of 1 week after initiation, 2 weeks after initiation 3 weeks after initiation, 4 weeks after initiation, 5 weeks after initiation, 6 weeks after initiation, 7 weeks after initiation, and 8 weeks after initiation. In one embodiment of the aforementioned inventions, contacting occurs in vivo. In one embodiment of the aforementioned inventions, contacting occurs in vitro. In one embodiment of the aforementioned inventions, the neuron is human.

Another aspect of the invention relates to a method of treating a subject for a CNS lesion. The method comprises administering to the subject a therapeutically effective amount of an inhibitor of PTEN and a therapeutically effective amount of an inhibitor of SOCS3, wherein administering results in contacting one or more target CNS neurons of the subject with the inhibitor of PTEN and the inhibitor of SOCS3, to thereby promote sustained survival, sustained regeneration, sustained compensatory outgrowth, or a combination thereof in the CNS neurons. In one embodiment, the subject is a human.

In one embodiment of the aforementioned inventions, the inhibitor of PTEN 15 selected from the group consisting of (a) potassium bisperoxo(bipyridine)oxovanadate (V) (bpV (bipy)); (b) dipotassium bisperoxo(5-hydroxypyridine-2-carboxyl)oxovanadate (V) (bpV(HOpic)) (c) potassium bisperoxo(1,10-phenanthroline)oxovanadate (V), (bpV(phen)); (d) dipotassium bisperoxo(picolinato)oxovanadate (V), (bpV(pic)); and (e) combinations thereof. In one embodiment of the aforementioned inventions, the inhibitor of SOCS3 is selected from the group consisting of SOCS3-specific hpRNA, siRNA, antisense SOCS3, dominant negative SOCS3, and combinations thereof. In one embodiment of the aforementioned inventions, the CNS lesion results from an acute injury. In one embodiment, the acute injury is selected from the group consisting of crush, severing, and acute ischemia. In one embodiment of the aforementioned inventions, administration first occurs within 24 hours of the injury. In one embodiment of the aforementioned inventions, administration first occurs within 3 days of the injury. In one embodiment of the aforementioned inventions, administration first occurs within 6 days of the injury. In one embodiment, the CNS lesion results from chronic neurodegeneration. In one embodiment, the CNS lesion results from a traumatic injury. In one embodiment, the CNS lesion results from a traumatic brain injury. In one embodiment, the CNS lesion results from a stroke. In one embodiment, the lesioned CNS neuron is in the optic nerve. In one embodiment, the CNS lesion results from an acute spinal cord injury. In one embodiment, the lesioned CNS neuron is in the spinal cord of a patient, and the inhibitor is intrathecally administered to the patient. In one embodiment, lesioned CNS neuron is a sensory neuron.

In one embodiment of the aforementioned inventions, the inhibitor is administered intravenously. In one embodiment of the aforementioned inventions, the inhibitor is administered intrathecally. In one embodiment of the aforementioned inventions, the inhibitor is administered ocularly. In one embodiment of the aforementioned inventions, the inhibitor is administered locally at the neuron. In one embodiment of the aforementioned inventions, an additional agent is administered to the subject. In one embodiment the additional agent is selected from the group consisting of inosine, oncomodulin, BNDF, NGF, CNTF, and combinations thereof.

Another aspect of the invention related to a device for promoting sustained survival of a lesioned mature neuron, sustained regeneration of a lesioned mature neuron, compensatory outgrowth of a neuron, or a combination thereof, comprising a reservoir loaded with a premeasured and contained amount of a therapeutically effective amount of an inhibitor of PTEN and an inhibitor of SOCS3. In one embodiment, the device is specifically adapted for implementing the method described herein.

Another aspect of the invention related to a pharmaceutical composition comprising a therapeutically effective amount of an inhibitor of SOCS3 and a therapeutically effective amount of an inhibitor of PTEN.

Cre-dependent reporter Tomato expression in RGCs after intravitreal AAV-Cre injection to Rosa tdTomato mice. (B) Representative retinal whole-mount images with TUJ1 staining at 3 weeks post-injury. (C) Quantification of RGC survival as measured by TUJ1 staining. The number from each injured group was compared with that of intact wild type mice. Between all animal groups subjected to injury, there was no statistically significant difference in the percentage of RGC survival. N=5-6. Error bars, s.d. Scale bars: 20 urn. GCL, ganglion cell layer.

Figure 9A:
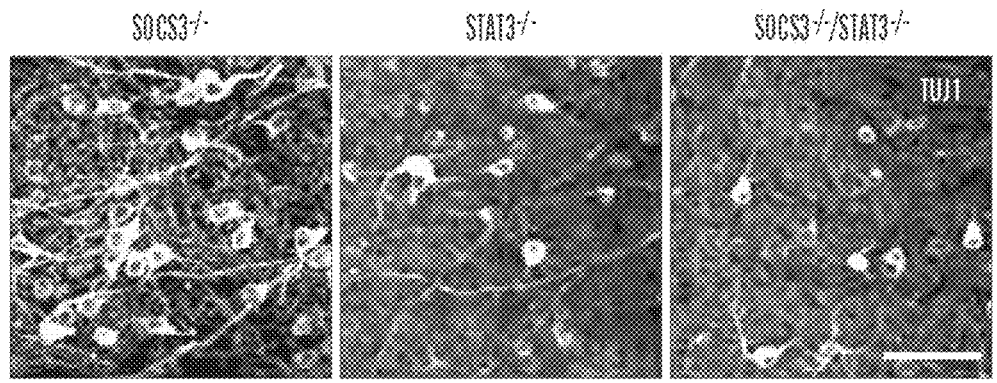
Figure 9B:
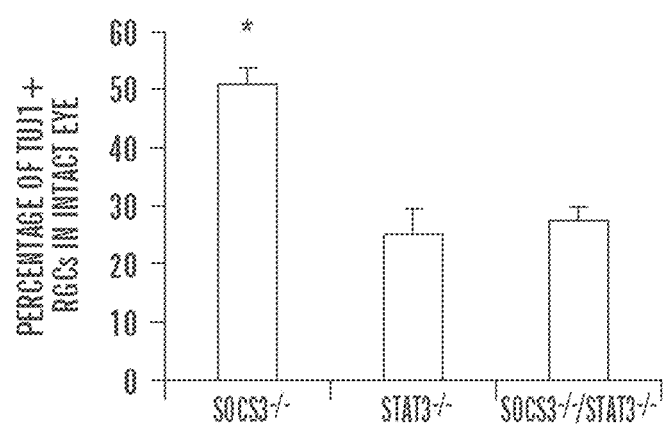

FIG. 9A-FIG. 9B are experimental results that show RGC survival at 2 weeks post-injury in SOCS3 and STAT3 mutant groups. (A) Representative retinal whole-mount images with TUJ1 staining at 2 weeks post-injury in AAV-Cre injected mice of SOCS3$^{f/f}$ (SOCS3$^{-/-}$), STAT3$^{f/f}$ (STAT3$^{-/-}$) or SOCS3$^{f/f}$/STAT3$^{f/f}$ (SOCS3$^{-/-}$/STAT3$^{-/-}$). Scale bar: 50 urn. (B) Quantification of RGC survival. The numbers of TUJ1+ RGCs were significantly higher in SOCS3$^{-/-}$ group than STAT3$^{-/-}$ and SOCS3$^{-/-}$/STAT3$^{-/-}$ groups. There was no significant difference between STAT3$^{-/-}$ and SOCS3$^{-/-}$/STAT3$^{-/-}$ groups. *: $p<0.001$, ANOVA, Tukey's post hoc test. Error bars, s.d. N=5 per group.

Figure 10A:
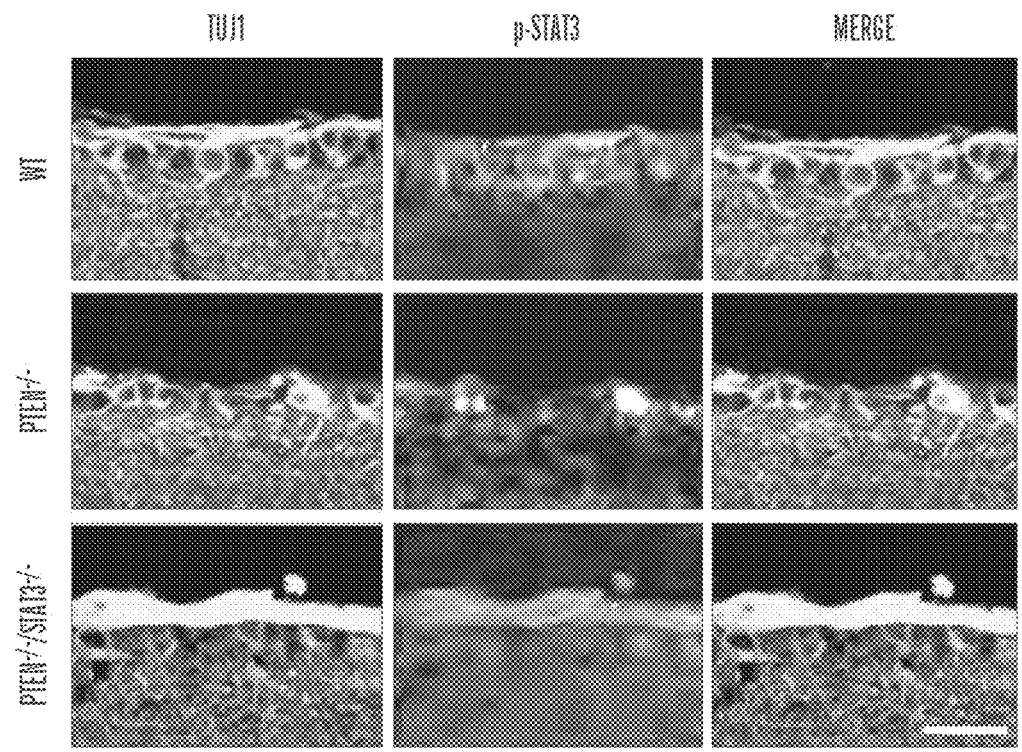
Figure 10B:
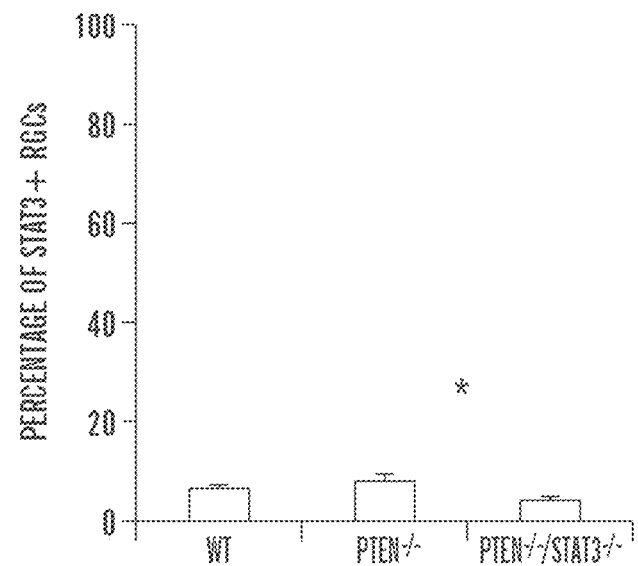
Figure 11B:
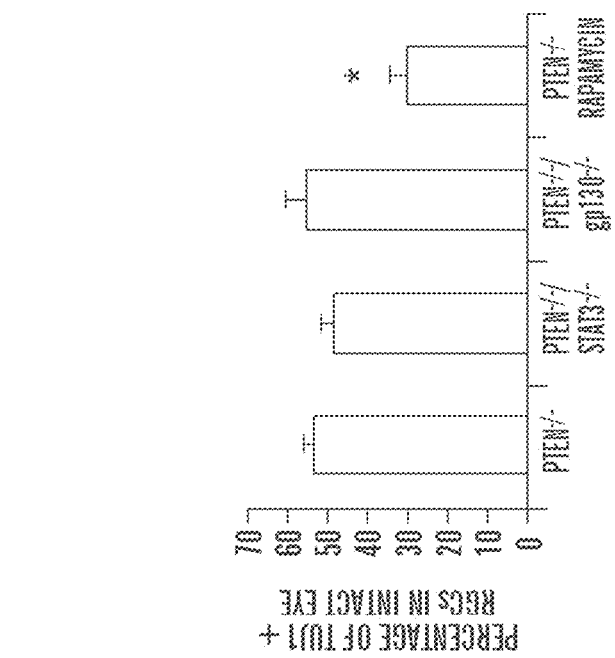
Figure 11A:
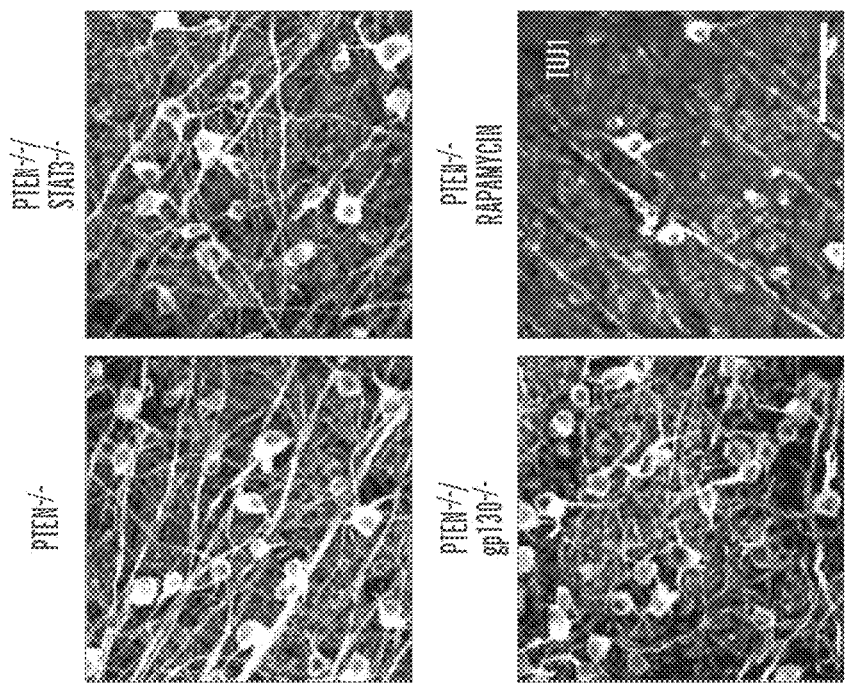
Figure 11D:
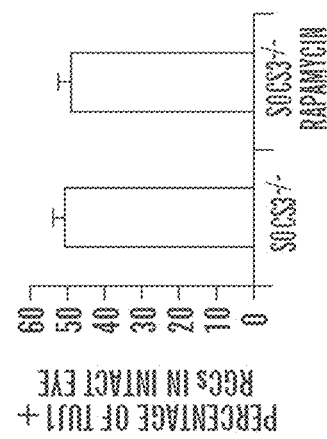
Figure 11C:
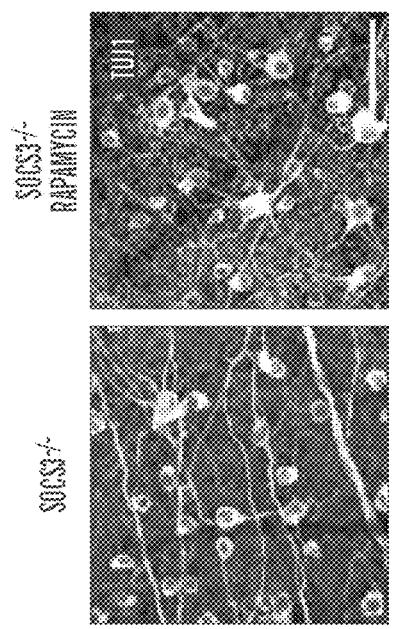
Figure 12A:
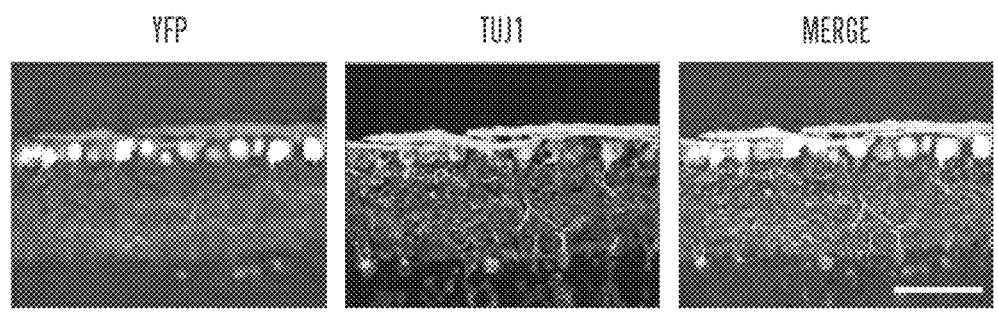
Figure 12B:
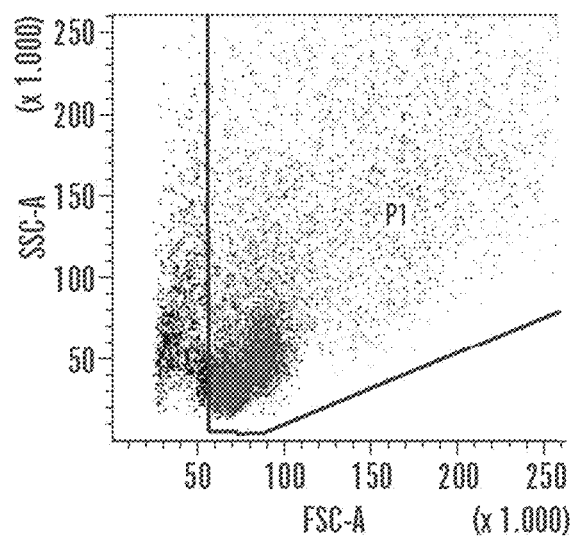
Figure 12C:
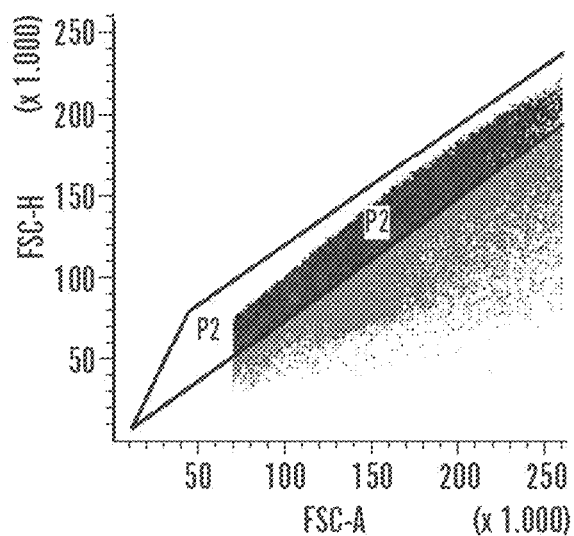
Figure 12D:
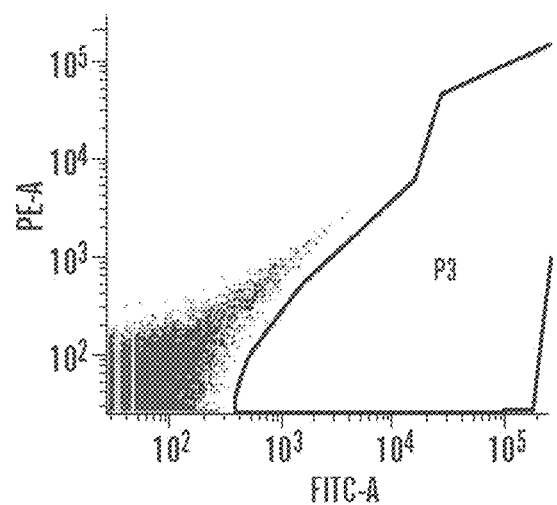
Figure 12E:
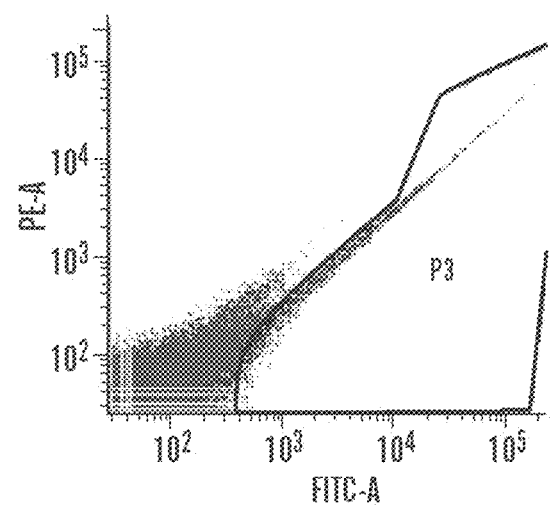

FIG. 10A-FIG. 10B are experimental results that indicate the effects of PTEN deletion on phospho-STAT3 levels in RGCs at 2 weeks post-injury. (A) Representative images of retinal sections showing the immunoreactivity with Phospho-STAT3 (originally visualized in red, reproduced here in black and white) or TUJ1 (originally visualized in green, reproduced here in black and white) in AAV-Cre injected mice of wild type (WT), PTEN$^{f/f}$ or PTEN$^{f/f}$/STAT3$^{f/f}$. Scale bar: 50 urn. (B) Quantification of p-STAT3 immunoreactive RGCs. When compared to the PTEN$^{-/-}$ group, the percentages of TUJ1+RGCs with nuclear p-STAT3 signals was similar in the WT group, but was significantly reduced in the PTEN$^{-/-}$/STAT3$^{-/-}$ group. *, $p<0.01$, Student's t test. Error bars, s.d. N=3 per group.

FIG. 11A-FIG. 11D are experimental results that indicate RGC survival in various animal groups. (A) Representative images of TUJ1-stained retinal whole mount at 2 weeks post-injury in AAV-Cre injected mice of PTEN$^{f/f}$ (PTEN$^{-/-}$), PTEN$^{f/f}$/STAT3$^{f/f}$ (PTEN$^{-/-}$/STAT3$^{-/-}$), PTEN$^{f/f}$/gp130$^{f/f}$ (PTEN$^{-/-}$/gp130$^{-/-}$), or PTEN$^{f/f}$ with rapamycin treatment. (B) Quantification of RGC survival as shown in (A). When compared to the PTEN$^{-/-}$ group, only PTEN$^{-/-}$ treated with rapamycin had significantly less survived RGCs. *: $p<0.001$, ANOVA, Dunnett's post hoc test. Error bars, s.d. N=4 per group. (C) Representative images of TUJ1-stained retinal whole mount at 2 weeks post-injury in AAV-Cre injected mice of SOCS3$^{f/f}$(SOCS3$^{-/-}$) with or without rapamycin. (D) Quantification of RGC survival as shown in (C). There was no significant difference between these two groups. Student's t test. Error bars, s.d. N=4 per group. Scale bars: 50 um.

FIG. 12A-FIG. 12E are experimental results that show isolation of YFP+ RGCs for RNA extraction and microarray analysis. (A) Representative images of retinal sections from YFP-17 mice detected for fluorescence or TUJ1+ signal showing that most of RGCs are YFP+. Only few non-RGCs were weakly labeled with YFP in the inner retinal layer. (B-E) Representative FACS plots illustrating the process of isolating YFP+ retinal cell population. (B) Dissociated retinal cells were gated based on both size (forward scatter, FSC, x axis) and surface characteristics (side scatter, SSC, y axis) to select the RGC neurons (P1). (C) Subsequently, aggregated cells were excluded based on FSC-H vs. FSC-A ratio, and single cells were selected (P2). (D) Retinal cells without YFP expression were used as control to set up the threshold for YFP positive cells in FL1 (FITC, x-axis) and FL2 (PE, y-axis) channels (P3). (E) YFP expressing cells within the gate (P3) were collected, which showed typical distribution of fluorescent signal.

Figure 13A:
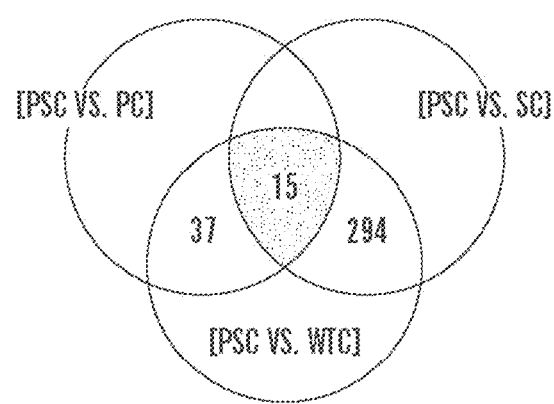
Figure 13C:
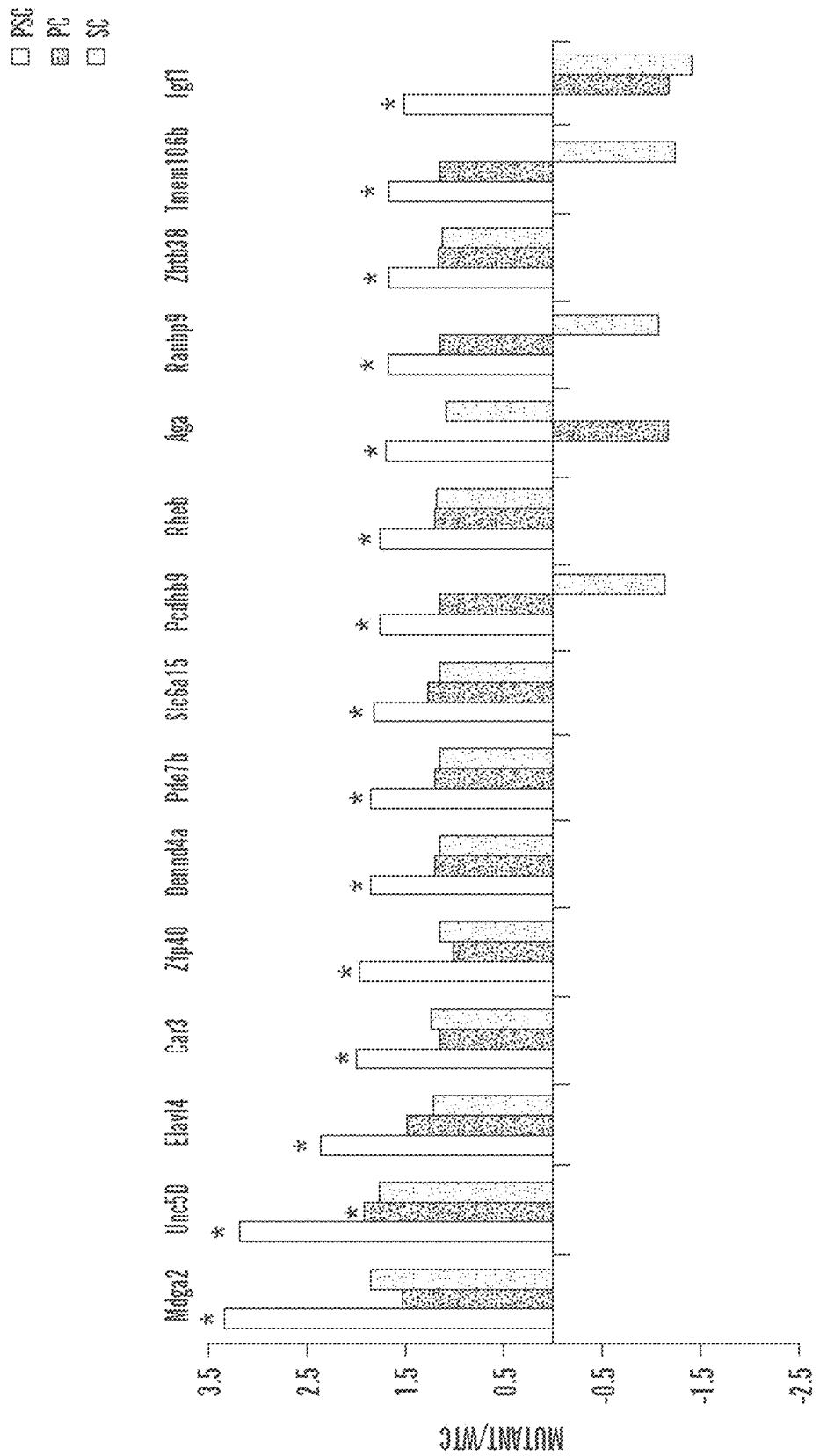
Figure 15A:
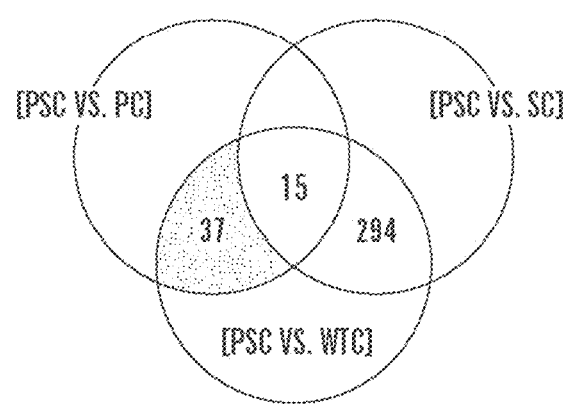
Figure 15C:
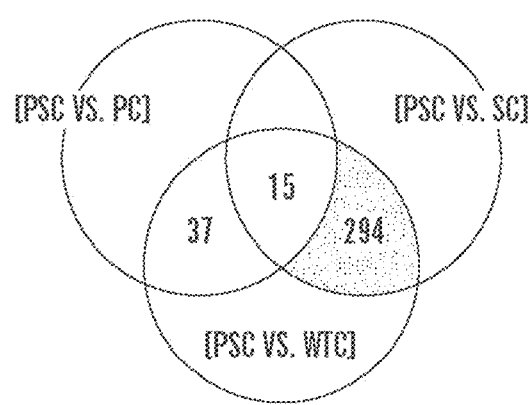

FIG. 13A-FIG. 13C are experimental results that show genes significantly different between the double mutant and both of the single mutants and the wild type controls. Gene expression levels of the sorted RGCs from the wild type, single or double mutants at 3 days post-injury were subjected to microarray analysis. Using $q<0.05$ as the cutoff criteria (FDR q value, SAM analysis), three lists of genes were obtained: 1. Genes whose expression levels are significantly different between PSC (PTEN/SOCS3 double mutant with crush) and PC (PTEN single mutant with crush), defined as [PSC vs. PC]; 2. Genes whose expression levels are significantly different between PSC and SC (SOCS3 single with crush), defined as [PSC vs. SC]; and 3. Genes whose expression levels are significantly different between PSC and wild type crush control (WTC), defined as [PSC vs. WTC]. (A) Highlighted area in the Venn diagram showing the genes that appear in ALL three lists, defined as [PSC vs. PC] AND [PSC vs. SC] AND [PSC vs. WTC]. The expression levels of individual genes in each mutant were shown in the list (B) and the bar graph (C), expressed as the ratios of their expression over that in wild type crush control (WTC). Value in bold (B) or asterisk (C) indicates a significant difference from WTC.

FIG. 14A-FIG. 14B show experimental results that indicate genes significantly altered in the double mutant but NOT in the single mutants when compared to the wild type controls. Using the cut-off criteria of fold change >1.6 and FDR<0.05 (SAM), three lists were obtained: (1). Genes whose expression levels are significantly different between PSC and WTC, defined as [PSC vs. WTC]; (2). Genes whose expression levels are significantly different between PC and WTC, defined as [PSC vs. WTC]; (3). Genes whose expression levels are significantly different between SC and WTC, defined as [SC vs. WTC]. Thereafter, Genes in either [PC vs. WTC], or [SC vs. WTC] were EXCLUDED from the list of [PSC vs. WTC], and the remaining genes in [PSC vs. WTC] were defined as [PSC vs. WTC] NOT [PC vs. WTC] NOT [SC vs. WTC]. (A). The expression levels of individual genes in each mutant, are shown as the ratios of their expression over that in wild type crush control (WTC). Value in bold indicates a significant difference from WTC (FDR<0.05, SAM). Some regeneration-associated genes are highlighted and are also listed in FIG. 16. (B). For this gene set, functional annotation clustering analysis was performed using DAVID. The functional annotation groups with similar EASE score, the Fish Exact Probability Value, were clustered and grouped under the same overall enrichment score. The five top-scored clusters with their counts of genes and their percentages to corresponding categories in the database are given.

FIG. 15A-FIG. 15D show experimental results that indicate genes significantly different between the double mutant and one of the single mutants and the wild type control. (A, B) Genes whose expression levels are significantly different between PSC and PC, PSC and WTC, but NOT between PSC and SC, are indicated by the highlighted area in the Venn diagram (A), and defined as [PSC vs. PC] AND [PSC vs. WTC] NOT [PSC vs. SC]. (B) Gene expression levels in each mutant are shown as the ratios of their expression over that in wild type crush control (WTC). Value in bold indicates a significant difference from WTC (FDR<0.05, SAM). Listed are genes with fold change >1.6 in both [PSC vs. PC] and [PSC vs. WTC]. (C, D) Genes whose expression levels are significantly different between PSC and SC, PSC and WTC, but NOT between PSC and PC, are indicated by the highlighted area in the Venn diagram (C), and defined as [PSC vs. SC] AND [PSC vs. WTC] NOT [PSC vs. PC]. (D) Gene expression levels in each mutant are shown as the ratios of their expression over that in wild type crush control (WTC). Value in bold indicates significant difference than WTC (FDR<0.05, SAM). Listed are genes with fold change >1.6 in both [PSC vs. SC] and [PSC vs. WTC]. For both (B) and (D), some regeneration-associated genes were highlighted and are also listed in FIG. 16.

Figure 16:
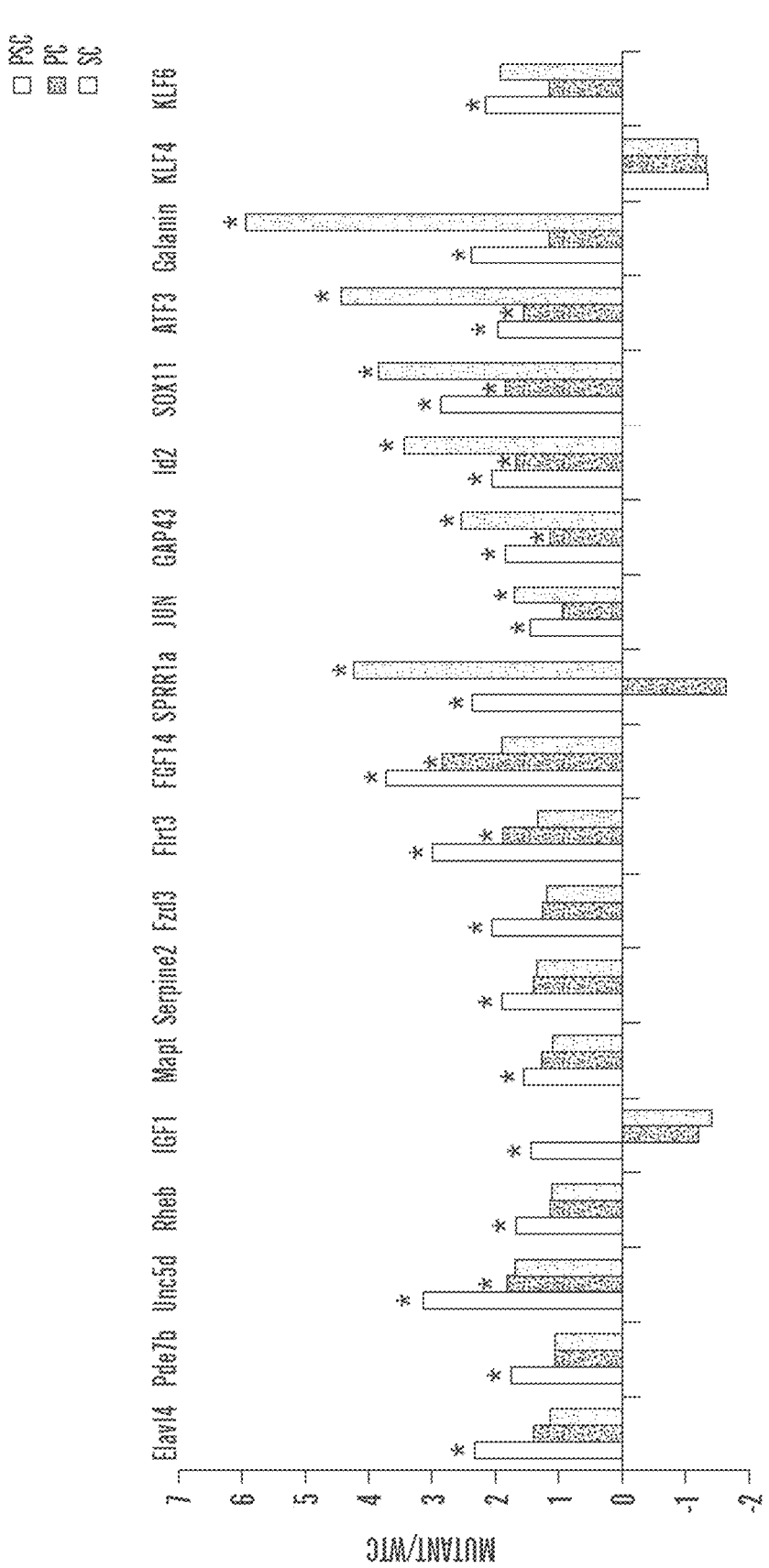
Figure 17A:
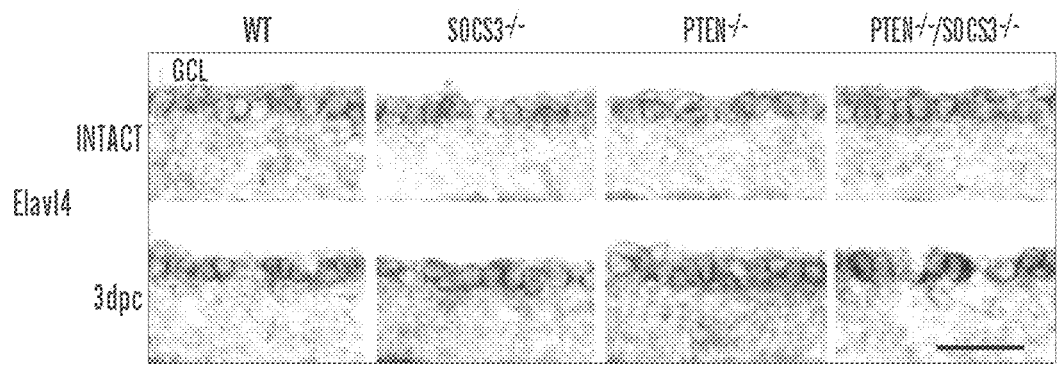
Figure 17B:
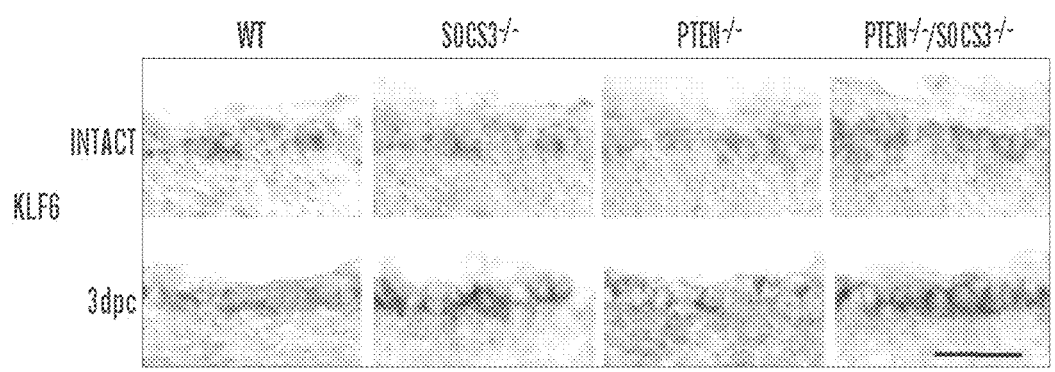
Figure 17C:
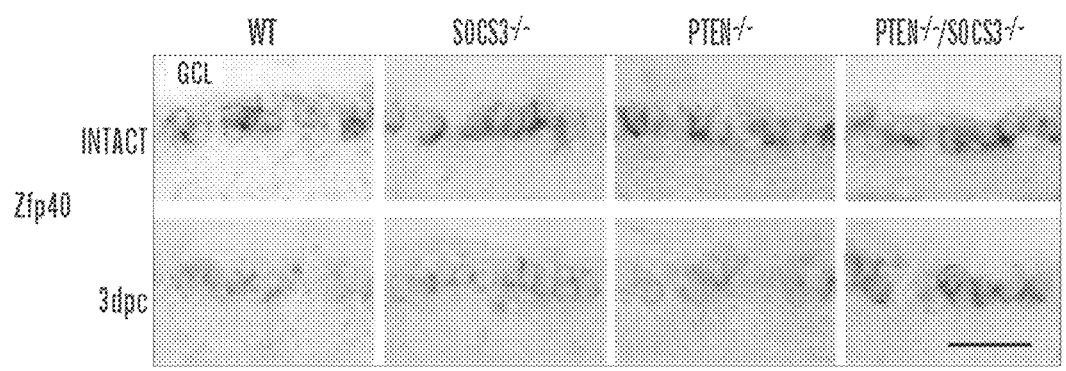
Figure 17D:
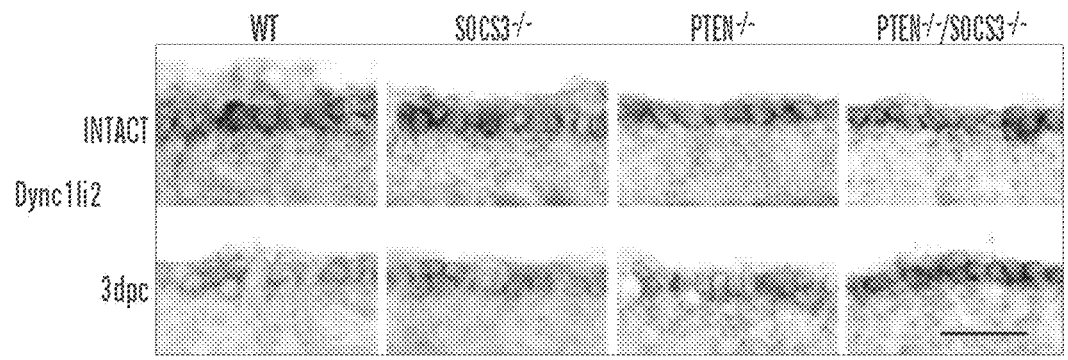
Figure 17E:
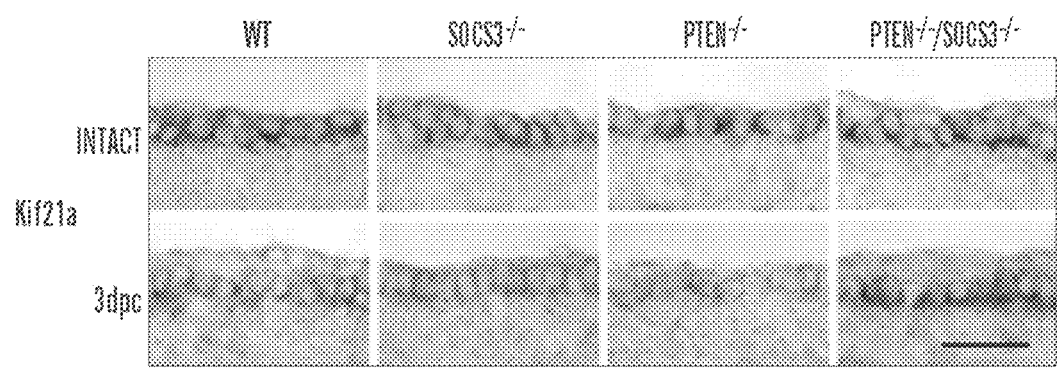
Figure 17F:
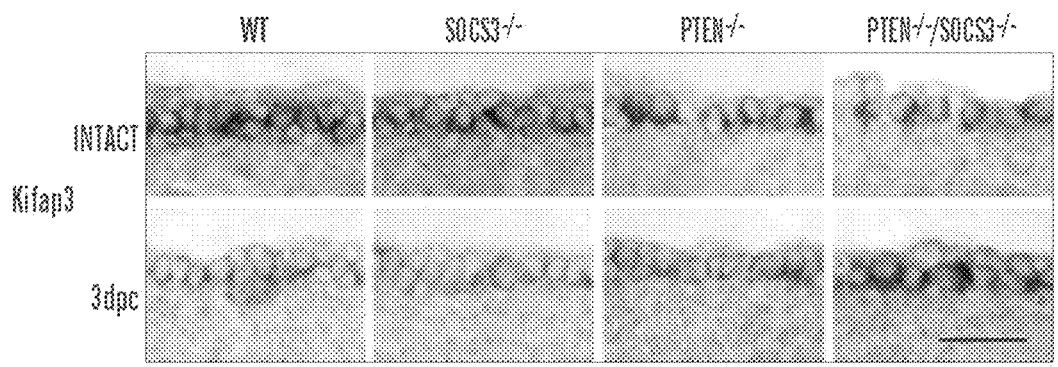

FIG. 16 shows experimental results that indicate the expression levels of some known regeneration-related genes in PTEN and/or SOCS3 mutants. The expression levels of individual genes in each mutant are shown as the ratios of their expression over that in wild type crush controls (WTC). In addition to those genes shown in the gene lists described above, many genes implicated in PNS axon regeneration, such as Jun, GAP43, Id2, SOX11, ATF3 and galanin, are most significantly altered in the groups with SOCS3 deletion (SC and PSC groups), consistent with the notion that JAK/STAT pathway is a critical pathway for PNS axon regeneration. Kruppel-like factors KLF4 and KLF6 showed expression changes in opposite directions (although the changes of KLF4 did not reach the level of statistical significance), consistent with proposed functions of these regeneration regulators.

FIG. 17A-FIG. 17F shows the presence of mRNAs of different genes in retinal sections detected by in situ hybridization. (A-F) Representative images showing the mRNA signals detected by anti-sense probes of Elavl4 (HuD) (A), KLF6 (B), ZFP40 (C), Dyncl 112 (D), Kif21 a (E), and Kifap3 (F) at the retinal sections from intact or 3 days post-injury of wild type (WT), PTEN$^{-/-}$, SOCS3$^{-/-}$ with CNTF, and PTEN$^{-/-}$/SOCS3$^{-/-}$ with CNTF mice. N=5-6 per group. Scale bars: 50 um.

FIG. 18A-FIG. 18F show experimental results that indicate SOCS3 deletion in neonatal cortical neurons increases CST sprouting after unilateral pyramidotomy. (A-C) Representative images of cervical 7 (C7) spinal cord transverse sections from Socs3$^{f/f}$ mice with cortical AAV-Cre injection and a sham injury (A) or with cortical AAV-GFP injection and a left pyramidotomy (Py) (B) or cortical AAV-Cre injection and a left pyramidotomy (C). As illustrated in FIG. 22, AAVs were injected into the right sensorimotor cortex of P1 Socs3$^{f/f}$ mice, which then received a left pyramidotomy or sham lesion at 8 weeks. BDA was injected into the right sensorimotor cortex at 4 weeks post-injury and the mice were terminated 2 weeks later. (D) Quantification of sprouting axon density index (contralateral/ipsilateral). *P<0.01, ANOVA followed by Bonferroni's post hoc test. (E) Scheme of quantifying crossing axons at different regions of the spinal cord (Mid: midline, Z1 or Z2: different lateral positions). (F) Quantification of crossing axons counted in different regions of spinal cord normalized against the numbers of labeled CST axons. *P<0.01, ANOVA followed by Bonferroni's post hoc test. Five mice used in each group. Three sections at the C7 level were quantified per mouse. Scale bar: 500 μm.

FIG. 19A-FIG. 19D show experimental results that indicate SOCS3 deletion in juvenile cortical neurons enhances CST sprouting after left pyramidotomy. (A-B) Representative images of cervical 7 (C7) spinal cord transverse sections from CamkII-cre mice crossed with wild type (A) or Socs3$^{f/f}$ (B) with a left pyramidotomy (Py) at the age of 8 weeks. BDA was injected into the right sensorimotor cortex at 4 weeks post-injury and the mice were terminated 2 weeks later. (C) Quantification of sprouting axon density index (contralateral/ipsilateral). *P<0.01, T-test. (D) Quantification of crossing axons counted in different regions of spinal cord normalized against the numbers of labeled CST axons. *P<0.01, T-test. Five mice in each group. Three sections at the C7 level were quantified per mouse. Scale bar: 500 μm.

FIG. 20A-FIG. 20G show experimental results that indicate CNTF expression in the neurons of the spinal cord deprived of CST inputs. (A-F) Representative images of the C7 transverse sections from the adult mice with a sham injury (A, C, and E) or 3 days after a left pyramidotomy (B, D, and F) stained with anti-CNTF (A, B), anti-NeuN (C, D) antibodies. Merged images are shown in E and F. (G) High magnification images from the area boxed in B showing the co-staining of anti-NeuN and anti-CNTF. Scale bars: 500 μm for A-D and 20 μm for G.

FIG. 21A-FIG. 21E show experimental results that indicate significant enhanced CST sprouting induced by co-deletion of SOCS3 and PTEN. (A-C) Representative images of cervical 7 (C7) spinal cord transverse sections from Socs3$^{f/f}$/Pten$^{f/f}$ mice with cortical AAV-Cre injection and a sham injury (A) or with cortical AAV-GFP injection and a left pyramidotomy (Py) (B) or cortical AAV-Cre injection and a left pyramidotomy (C). The experimental procedures were described in FIG. 22G. (D) Quantification of sprouting axon density index (contralateral/ipsilateral). *P<0.01, ANOVA followed by Bonferroni's post hoc test. (E) Quantifications of crossing axons counted in different regions of spinal cord normalized against the numbers of labeled CST axons. *P<0.01, ANOVA followed by Bonferroni's post hoc test. Five mice used in each group. Three sections at the C7 level were quantified per mouse. Scale bar: 500 μm.

FIG. 22A-FIG. 22G show experimental results that indicate SOCS3 deletion in neonatal cortical neurons increases CST sprouting at thoracic and lumbar levels after unilateral pyramidotomy. (A-D) Representative images of T4 (A, C) or L1 (B, D) spinal cord transverse sections from Socs3$^{f/f}$ mice with cortical AAV-GFP injection (A, B) or AAV-Cre (C, D) and a left pyramidotomy (Py). (E) Quantification of sprouting axon density index (contralateral/ipsilateral). *P<0.01, T-test. (F) Quantification of crossing axons counted in different regions of spinal cord normalized against the numbers of labeled CST axons. *P<0.01, T-test. Five mice used in each group. Three sections at the C7 level were quantified per mouse. Scale bar: 500 μm. (G) Scheme of the experiments. AAVs were injected into the right sensorimotor cortex of P1 Socs3$^{f/f}$ mice, which then received a left pyramidotomy or sham lesion at 8 weeks. BDA was injected into the right sensorimotor cortex at 4 weeks post-injury and the mice were terminated 2 weeks later.

FIG. 23A-FIG. 23F show experimental results that indicate characterization of the CamkII-Cre line. (A-D) Representative transverse spinal cord sections from the CamkII-Cre mice crossed with a foxed Tomato reporter at the age of 1 week (A), 2 weeks (B), 3 weeks (C), or 2 months (D). In the dorsal column, the Tomato signal is seen at the age of 2 months, but not 1-3 weeks, consistent with its reported expression patterns (Yu et al., 2001). Cre is expressed in the superficial levels of dorsal spinal cord starting from 3 weeks. Scale bar: 500 μm. (E, F) co-localization of some Cre-expressing cells with NeuN (E) or GFAP (F). Scale bar: 20 μm.

FIG. 24A-FIG. 24H show experimental results that indicate co-localization of CNTF with NeuN+, but not CD68+ or GFAP+ cells. (A-D) Representative images of C7 transverse sections from the adult mice with a sham injury (A, B) or 3 days after a left pyramidotomy (C, D) stained with anti-CD68 (A, C) or anti-GFAP (B, D). Scale bar: 500 µm. (E-F) High magnification images from the spinal cord of 3 days post-injury showing the co-staining of anti-CNTF with anti-CD68 (E) or anti-GFAP (F). Scale bar: 20 µm. (G, H) Representative images of the cortical sections from the adult mice with a sham injury (G) or 3 days after a left pyramidotomy (H) stained with anti-CNTF. Scale bar: 100 µm.

FIG. 25A-FIG. 25F show experimental results that indicate CNTF injected to the spinal cord leading to CST sprouting. (A, B) Representative images from the C1 transverse spinal cord sections from the mice SOCS3 f/f with cortical AAV-Cre injection at P1 and intraspinal injection of saline (A) or CNTF (B) at 8 weeks. Arrows indicates the injection needle trajectory. (C, D) High magnification images from (A, B) highlights the midline areas without (C) or with (D) numerous crossing CST axons. (E, F) No CST sprouts seen at C7 levels of the mice with saline (E) or CNTF (F) injection. Scale bar: 500 µm for A, B, E, and F; 100 µm for C, and D.

FIG. 26A-FIG. 26E show experimental results that indicate further enhanced CST sprouting in the lower spinal cord of the mice with co-deletion of PTEN and SOCS3 in cortical neurons. (A-D) Representative images of T4 (A, C) or L1 (B, D) spinal cord transverse sections from $PTEN^{f/f}/Socs3^{f/f}$ mice with cortical AAV-GFP injection (A, B) or AAV-Cre (C, D) and a left pyramidotomy (Py). (E) Quantification of crossing axons counted in different regions of spinal cord normalized against the numbers of labeled CST axons. *P<0.01, T-test. Five mice used in each group. Three sections at the C7 level were quantified per mouse. Scale bar: 500 µm.

DETAILED DESCRIPTION OF THE INVENTION

Previous work has indicated that inhibition of either PTEN or SOCS3 results in limited neuronal regeneration of injured neurons. Remarkably, the experiments disclosed herein indicate that simultaneous inhibition of both PTEN and SOCS3 enables robust and sustained axon regeneration. PTEN and SOCS3 are also shown to regulate two independent pathways that act synergistically to promote enhanced axon regeneration. Gene expression analyses suggest that co-inhibition of PTEN and SOCS3 not only results in the induction of many growth-related genes, but also allows neurons to maintain the expression of a repertoire of genes at the physiological level after injury. These results indicate that concurrent activation of mTOR and STAT3 pathways can sustain long-distance axon regeneration in adult, a crucial step toward functional recovery.

Aspect of the invention relate to the combined inhibition of PTEN and SOCS3 in an injured neuron to induce extended or sustained survival and regeneration following an injury. As such, one aspect of the invention relates to a method of promoting sustained survival, sustained regeneration, or a combination of both, in a lesioned mature neuron. The method comprises contacting the lesioned mature neuron with an effective amount of an inhibitor of PTEN and an effective amount of an inhibitor of SOCS3 to thereby promote sustained survival, sustained regeneration, or a combination of both, of the neuron.

It has also been observed that combined inhibition of PTEN and SOCS3 in an uninjured target neuron will promote axonal outgrowth of uninjured neurons to an area of injury and such outgrowth can have a compensatory role in recovery of the organism from the injury. Another aspect of the invention relates to a method of promoting sustained compensatory outgrowth of an uninjured target neuron to a region of neuronal lesion, comprising contacting the target neuron with an effective amount of an inhibitor of PTEN and an effective amount of an inhibitor of SOCS3, to thereby promote compensatory outgrowth (e.g. axonal) of the target neuron to the region of neuronal lesion. In one embodiment, the target neuron is further contacted with a denervation-induced cytokine (e.g., CNTF) at a location proximal to the site of neuronal lesion.

Another aspect of the invention relates to a method of treating a subject for a nervous system lesion. The method comprises administering to the subject a therapeutically effective amount of an inhibitor of PTEN and a therapeutically effective amount of an inhibitor of SOCS3, wherein administering results in contacting one or more lesioned neurons and/or the lesion site of the subject with the inhibitor of PTEN and the inhibition of SOCS3, to thereby promote sustained survival, sustained regeneration, or a combination of both in the injured neurons. The contacting occurs at the same time so as to coordinately inhibit both PTEN and SOCS3.

An effective amount of the inhibitors are contacted with the neuron using a suitable method sufficient to promote sustained survival of the neuron and/or regeneration and/or sustained compensatory outgrowth of the neuronal axon. An effective amount is the amount required to produce statistically significant and reproducible sustained survival, sustained regeneration, or a combination of both, as compared to an appropriate control. For in vitro methods, the inhibitors are, for example, added to the culture medium, usually at nanomolar or micromolar concentrations. The respective inhibitors can be added in the same formulation, or in different formulations.

For in vivo applications, the inhibitors can be administered to the subject by any method that results in contacting both a therapeutically effective amount of each to the neuron at relatively the same time, e.g., orally, by intravenous (i.v.) bolus, by i.v. infusion, subcutaneously, intramuscularly, ocularly (intraocularly, periocularly, retrobulbarly, intravitreally, subconjunctivally, topically, by subtenon administration, etc.), intracranially, intraperitoneally, intraventricularly, intrathecally, by epidural, etc. The respective inhibitors can be administered at the same time or at different times, depending upon various factors associated with each inhibitor (e.g., half life, administration route, etc.). The respective inhibitors can be administered by the same route of administration or through different routes of administration. The administration of the respective inhibitors can be for differing prolonged periods, as long as the combined administration conforms to the time periods specified herein for both inhibitors such that their activities on the contacted neurons completely or substantially overlap. The respective inhibitors can be administered in a formulation which contains both inhibitors (a pharmaceutical composition, as described herein), or they can be in separate formulations (separate pharmaceutical compositions) for separate administration.

Sustained survival of a neuron is indicated by the number of neurons surviving from a specific injury or condition, as compared to the number of neurons surviving as a result of the effects of the individual inhibitor (either PTEN or SOCS3), and also by the length of time the survival persists, as compared to the length of time survival persists as a result of the effects of the individual inhibitor (either PTEN or SOCS3). Survival is considered to be sustained if it persists for an extended period of time post-injury (e.g., greater than 2 weeks post-injury, greater than 3 weeks, and greater than 4 weeks post-injury). In one embodiment, greater than 10% of neurons (e.g., 15%, 20%, 25%, 30%, 35%, 0%, 45%, 50%, 55%, 60%, 65%, 70% and 75%), survive for an extended period of time post-injury. In one embodiment, greater than 20% of neurons survive for an extended period of time post-injury.

Sustained regeneration or outgrowth is indicated by the number of neurons (injured and also uninjured) and by extended length of the axonal outgrowth of the neurons, as compared to the number of neurons and extended length of the axonal outgrowth of the neurons that results from the effects of the individual inhibitor (either PTEN or SOCS3), and by the time frame post-injury that the outgrowth occurs, as compared to the time frame post-injury that outgrowth occurs resulting from the effects of the individual inhibitor (either PTEN or SOCS3). Sustained regeneration and axonal outgrowth occurs if greater than 10% or greater than 20% (e.g., 15%, 20%, 25%, 30%, 35%, 0%, 45%, 50%, 55%, 60%, 65%, 70% and 75%) of the neurons regenerate injured axons or generate new axons, that extend at least 0.5 mm distal to the lesion epicenter. In one embodiment, greater than 10% or greater than 20% (e.g., 15%, 20%, 25%, 30%, 35%, 0%, 45%, 50%, 55%, 60%, 65%, 70% and 75%) of neurons regenerate injured axons or generate axons over 1 mm distal to the lesion site. In one embodiment, greater than 10% (e.g., 15%, 20%, 25%, 30%, 35%, 0%, 45%, 50%, 55%, 60%, 65%, 70% and 75%) or greater than 20% of neurons regenerate or generate new axons that extend at least 2 mm distal from the lesion site.

Sustained regeneration and axonal outgrowth is also indicated by a significant amount of outgrowth occurs on or after 2 weeks post-injury. For example significant outgrowth occurs for up to 3 weeks or 4 weeks post-injury.

Neurons

The methods and compositions described herein are suited for the promotion of sustained survival, sustained neuronal regeneration and sustained axonal outgrowth of CNS (central nervous system) and PNS (peripheral nervous system) neurons. In one embodiment the neuron is a terminally differentiated neuron. In one embodiment, the neuron is an adult neuron (e.g, in a subject that has reached maturity, such as in humans older than 18 years). In one embodiment, the neuron is non-embryonic. In one embodiment, the neuron is in an immature organism (e.g., embryo, infant, child).

All CNS and PNS neurons are suitable for such methods described herein. CNS neurons include, without limitation, a cerebellar granule neuron, or an ocular neuron. In one embodiment, the neuron is the optic nerve. In one embodiment, the neuron is a sensory neuron (e.g., dorsal root ganglion (DRG) sensory neuron). In one embodiment, the CNS neuron is known or determined to be under specific PTEN and/or SOCS3 regeneration inhibition. Such determination can be determined by the skilled practitioner.

As used herein, the term "PNS neurons" is intended to include the neurons commonly understood as categorized in the peripheral nervous system, including sensory neurons and motor neurons. The present invention provides methods and compositions for preventing and/or treating peripheral nerve damage (peripheral neuropathy) in a subject. Peripheral nerves such as dorsal root ganglia, otherwise known as spinal ganglia, are known to extend down the spinal column. These nerves can be injured as a result of spinal injury. Such peripheral nerve damage associated with spinal cord injury can also benefit from neuron axonal outgrowth produced by the methods described herein.

All mammals are suitable subjects for performance of the methods described herein. In one embodiment, the mammal is a human, non-human primate, companion animal (e.g., dog, cat), livestock animal (e.g., horse, cow, pig, sheep), or rodent (mouse, rat, rabbit). In one embodiment, the subject is a non-human primate animal in a model for neurodegeneration or nervous system (CNS or PNS) injury. Neurons derived from said subjects are also suitable for performance of the methods described herein.

Neuronal Lesions

As used in the art, the term lesion refers to damage (e.g., to a system or a cell). Damage to a system is evidenced by aberrant function, reduction of function, loss of function of the system, or loss of essential components (e.g., specialized cells such as neurons). Damage to a specific neuron is also evidenced by aberrant function, loss of function, reduced function, and/or cell death. Some forms of damage to a neuron can be directly detected (e.g., by visualization as with a severed or crushed neuronal axon). Neuronal lesions can result from a variety of insults, including, injury, toxic effects, atrophy (e.g., due to lack of trophic factors). Injuries that typically cause neuronal lesions include, without limitation, severing and crushing.

A neuronal lesion, as the term is used herein, results from damage to the neuron. Such damage may be complete loss of a neuron, or loss of a part of the neuron (e.g., an axon). Such damage may results from acute or traumatic injury to the neuron (e.g., crush, severing) such as the result of external trauma to the subject (e.g., contusion, laceration, acute spinal cord injury, traumatic brain injury, cortical impact, etc.). Acute or traumatic injury to a neuron can also result from an acute condition, such as stroke, that results in acute ischemia to the neuron resulting in acute damage. The specific location of neuronal damage will vary with the specific cause of the damage, and the specific individual. In one embodiment of the invention described herein, the lesioned CNS neuron is located in CNS white matter, particularly white matter that has been subjected to traumatic injury. The specific location of a lesion to a specific neuron will vary with respect to the injury. In one embodiment, the lesion is in the axon or dendrite of a neuron.

Damage to a neuron may also be incurred from a chronic injury (e.g., repetitive stress injury) or condition (e.g., chronic inflammation or disease). Chronic injury leads to neurodegeneration such as caused by neurotoxicity or a neurological disease or disorder (e.g. Huntington's disease, Parkinson's disease, Alzheimer's disease, multiple system atrophy (MSA), etc.).

In one embodiment of the invention, damage results from an ocular injury or disorder (e.g. toxic amblyopia, optic atrophy, higher visual pathway lesions, disorders of ocular motility, third cranial nerve palsies, fourth cranial nerve palsies, sixth cranial nerve palsies, internuclear ophthalmoplegia, gaze palsies, eye damage from free radicals, etc.), or an optic neuropathy (e.g. ischemic optic neuropathies, toxic optic neuropathies, ocular ischemic syndrome, optic nerve inflammation, infection of the optic nerve, optic neuritis, optic neuropathy, papilledema, papillitis, retrobulbar neuritis, commotio retinae, glaucoma, macular degeneration, retinitis pigmentosa, retinal detachment, retinal tears or holes, diabetic retinopathy, iatrogenic retinopathy, optic nerve drusen, etc.).

Damage to a neuron can be detected by the skilled practitioner through a variety of assays known in the art. Loss of function assays can be used to determine neuronal damage. Physical damage to the neuron (e.g., axonal crushing or severing) can sometimes be observed diagnostically through routine methods. One way to detect a lesion is through detection of axotomy-induced stress and/or pathology-induced down-regulation of protein translation (e.g., detected directly, indirectly, or inferred).

Diseases and Disorders

The methods and compositions of the invention are useful for treatment of diseases or disorders resulting from or leading to the neuronal lesions described herein. For example, the methods and compositions described herein can be used specifically to treat damage associated with peripheral neuropathies including, but not limited to, the following: diabetic neuropathies, virus-associated neuropathies, including acquired immunodeficiency syndrome (AIDS) related neuropathy, infectious mononucleosis with polyneuritis, viral hepatitis with polyneuritis; Guillian-Barre syndrome; botulism-related neuropathy; toxic polyneuropathies including lead and alcohol-related neuropathies; nutritional neuropathies including subacute combined degeneration; angiopathic neuropathies including neuropathies associated with systemic lupus erythematosis; sarcoid-associated neuropathy; carcinomatous neuropathy; compression neuropathy (e.g. carpal tunnel syndrome) and hereditary neuropathies, such as Charcot-Marie-Tooth disease, peripheral nerve damage associated with spinal cord injury can also be treated with the present method. The subject is treated in accordance with the present method for peripheral nerve damage as the result of peripheral neuropathies, including those listed above. Subjects at risk for developing such peripheral nerve damage are also so treated.

PTEN Inhibitors

A variety of PTEN inhibitors suitable for use in the methods and compositions described herein are known in the art. Some suitable PTEN inhibitors, such as vanadium-based PTEN inhibitors or siRNA, are described in U.S. Published Patent Application No. 2009/0305333. One example of a PTEN inhibitor is SF1670 (Cellagen Technology C7316). Another example of a PTEN inhibitor is 4-hydroxynonenal Yet another example of a PTEN inhibitor is P-REX2a. In one embodiment, the PTEN inhibitor is a vanadium-based PTEN inhibitor, such as sold commercially by Calbiochem, EMD/Merck, including (a) potassium bisperoxo(bipyridine)oxovanadate (V) (bpV(bipy)); (b) dipotassium bisperoxo(5-hydroxypyridine-2-carboxyl)oxovanadate (V) (bpV(HOpic)); (c) potassium bisperoxo(1,10-phenanthroline)oxovanadate (V), (bpV(phen)); and (d) dipotassium bisperoxo(picolinato)oxovanadate (V), (bpV(pic)). Alternative, suitable PTEN inhibitors include PTEN inhibitor compounds of formulas I-XIV as described in WO2005/097119; vanadium-based PTEN inhibitors described in US20070292532 and by Rosivatz et al. 2006 (ACS Chem. Biol. 1(12) 780-790); the 1,4-naphthoquinone derivative, shikonin, described by Nigorikawa et al. (Mol Pharmacol 70:1143-1149, 2006); and menadione (vitamin K3) as described by Yoshikawa et al., Biochim Biophys Acta. 2007 April; 1770(4):687-93. PTEN inhibition assays for general screening (to identify and confirm alternative, suitable inhibitors) and IC50 determinations are known in the art, e.g. WO 2005/097119. Suitable PTEN inhibitors are also described in WO 2007/0203098, including all recited genera, subgenera and species disclosed and as described therein including, without limitation, I) Ascorbic acid-based PTEN inhibitors, II) 1,2,3-triazole PTEN inhibitors (such as described in WO02/32896), III) Diamide PTEN inhibitors, IV) Aryl imidazole Carbonyl PTEN inhibitors, V) Polyamide PTEN inhibitors, VII) 1,10-phenanthroline-5,6-dione PTEN inhibitors, VIII) substituted phenanthrene-9-10-dione PTEN inhibitors, IX) Isatin PTEN inhibitors, X) substituted phenanthren-9-ol PTEN inhibitors, XI) substituted naphthalene-1,2-dione PTEN inhibitors, XII) substituted naphthalene-1,4-dione PTEN inhibitors, XIII) Vanadate-Based PTEN Inhibitors 1. Potassium Bisperoxo(bipyridine) oxovanadate (V) 2. Dipotassium Bisperoxo (5-hydroxypyridine-2carboxyl) oxovanadate (V) 3. Dipotassium Bisperoxo (picolinato)oxovanadate (V) 4. Monoperoxo(picolinato) oxovanadate (V) 5. Potassiun Bisperoxo (1,10-phenanthroline) oxovanadate (V) 6. bis(N,N-Dimethylhydroxamido) hydroxooxovanadate, XIV) T1-loop binding element containing PTEN inhibitors. The PTEN inhibitors may contain a group that exists at physiological pH in significantly anionic form, such as at least 5% of the molecular species at pH of 7.4 are anionic charged. Such anionic groups can bind to PTEN in the T1 loop of the peptide structure in solution.

PTEN-specific antibody and intrabody inhibitors may also be used, such as have been intrabodies for the therapeutic suppression of a variety of neurodegenerative pathologies, e.g. Messer et al. Expert Opin Biol Ther. 2009 September; 9(9):1189-97.

In one embodiment the PTEN inhibitor is specifically designed and/or targeted to facilitate delivery to the interior of the target neuron(s).

PTEN can be effectively inhibited by targeting one or more components of the PTEN cell signalling pathway. Examples of such components include, without limitation, phosphatase and tensin homologue (PTEN), glycogen synthase kinase 3 beta (GSK3β), and AKT (also referred to as protein kinase B (PKB)), such as with compounds that activate a phosphoinositide-3 kinase (PI3K) pathway, for example, inhibitors of PTEN, inhibitors of GSK3β, or activators of AKT (e.g., as described in U.S. Patent Application Publication 2011/0189308). The use of various combinations of PTEN inhibitors or combinations of inhibition approaches is also envisioned.

SOCS3 Inhibitors

Various inhibitors of suppressor of cytokine signaling 3 (SOCS3) are known in the art. The inhibitor may specifically bind or compete with the SOCS-3 gene, transcript or translate (protein). Suitable inhibitors include, without limitation, SOCS3-specific polynucleotides and PNAs targeting the SOCS3 gene or transcripts, and include SOCS3-specific hpRNA, siRNA, and antisense polynucleotides. Materials and methods for making and using such polynucleotides are known in the art, including design and cloning strategies for constructing suitable SOCS3 shRNA expression vectors (e.g. McIntyre et al., BMC Biotechnol. 2006; 6:1), and suitable antisense SOCS3 cDNAs (Owaki, et al., J. Immunol. 2006 Mar. 1; 176(5):2773-80). Suitable SOCS3-specific polynucleotides targeting the SOCS3 gene or transcripts are also commercially available from several vendors including OriGene (Rockville Md.) such as vector pRFP-C-RS and pGFP-V-RS, human 29mer shRNA constructs against SOCS3 in pRFP-C—RS and pGFP-V-RS vectors, respectively. SOCS3 specific siRNA is also widely commercially available, e.g. Santa Cruz Biotechnology, Inc. Examples of specific SOCS3 specific siRNA to inhibiti SOCS3 are provided in U.S. Patent Application Publication 2011/0124706.

Suitable inhibitors also include SOCS3-based polypeptides like dominant negative SOCS3 peptides and proteins, such as SOCS3 (F25A) (e.g. Owaki, et al., J. Immunol. 2006 Mar. 1; 176(5):2773-80), which contains a point mutation in the kinase inhibitory region of SOCS3.

SOCS3-specific antibody and intrabody inhibitors may also be used, such as have been intrabodies for the therapeutic suppression of a variety of neurodegenerative pathologies, e.g. Messer et al. Expert Opin Biol Ther. 2009 September; 9(9):1189-97. A SOCS3 antibody is commercially available (MyBioSource, Catalog #MBS242513).

The structural determination of SOSC3 has also facilitated development of small-molecule SOCS3 specific inhibitors, e.g. Babon et al., J Mol Biol. 2009 Mar. 20; 387(1):162-74; Babon et al., Mol Cell 2006 Apr. 21; 22 (2) 205-16. Structure-based SAR yield chemically diverse small molecule SOCS3 inhibitors at micro- and nanomolar activity.

In one embodiment the SOCS3 inhibitor is specifically designed and/or targetted to facilitate delivery the target neuron(s) cell interior.

SOCS3 inhibition is readily assayed by specific techniques, such as immunocytochemistry. Because SOCS3 up-regulation occurs after CNTF treatment inhibitors of SOCS3 (expression or activity) allow sustained p-STAT3 levels, and SOCS3 inhibition may be measured by STAT3 activation. For example, COS cells can be treated with CNTF and monitored for sustained phosph-STAT3 signals. In another embodiment, cultured neurons can be incubated in serum-free medium with or without serially-diluted inhibitor, e.g. for 6 hr. The cells are then incubated with a polyclonal antibody against phospho-STAT3, such as Tyr705 (Cell Signaling Technology, Danvers, Mass.); see, e.g. Liu et al., J Neurosci, September 2001, 21(17) RC164, 1-5.

The use of various combinations of SOCS3 inhibitors is also envisioned.

Administration

Administration is to a subject by a route that results in contacting an effective amount of the respective inhibitors to the target neuron(s). As the term is used herein, the target neuron is the neuron which is intentionally contacted by the administered agent. A target neuron can be a lesioned neuron or a non-lesioned neuron (e.g., for compensatory axonal outgrowth to a region of dennervation). The target neuron may be contacted at one or more specific target sites of the neuron. As the term is used herein, the target site of the neuron is the region of the neuron to which the agent is intentionally contacted. Regions of the neuron include the dendrites, cell body, and the axon. Since regeneration and axonal generation in the treatment of a neuronal injury includes compensatory promotion of axonal outgrowth of uninjured neurons, benefit is expected from mere delivery of the inhibitors and/or other agents to an injury site. As such, suitable target neurons are actual damaged neurons, and also neurons that are in the immediate area of an injury site or an area of dennervation. The specific location and extent of an injury site can be determined by the skilled practioner. Examples of injury sites are the site of physical damage or disruption of neuronal activity. The immediate area of an injury site will vary with respect to the specific injury, the nature of the injury, and the nature of the injured neurons (e.g., axonal length, specific function, etc.) and can be determined by the skilled practitioner. Typically a lesion is in the axon of the injured neuron. In one embodiment, the immediate area of the injury site is within about 1-10 mm of identified damaged neurons (e.g., 1, 2, 3, 4, 5, 6, 7, 8, 9, or 10 mm).

In one embodiment, the administration is localized so as to be highly targetted to a specific site. In one embodiment, the administration is systemic, and results in delivery of the appropriate concentration to the specific site.

Depending on the intended route of delivery, the compositions may be administered in one or more dosage form(s) (e.g. liquid, ointment, solution, suspension, emulsion, tablet, capsule, caplet, lozenge, powder, granules, cachets, douche, suppository, cream, mist, eye drops, gel, inhalant, patch, implant, injectable, infusion, etc.). The dosage forms may include a variety of other ingredients, including binders, solvents, bulking agents, plasticizers etc.

In a specific embodiment, the inhibitors are contacted with the neuron using an implantable device that contains the inhibitors and that is specifically adapted for delivery to a neuron. Examples of devices include solid or semi-solid devices such as controlled release biodegradable matrices, fibers, pumps, stents, adsorbable gelatin (e.g. Gelfoam), etc. The device may be loaded with premeasured, discrete and contained amounts of the inhibitors sufficient to promote sustained regeneration or sustained survival of the neuron. In one embodiment, the device provides continuous contact of the neuron with the inhibitors at nanomolar or micromolar concentrations, (e.g., for at least 2, 5, or 10 days, or for at least 2, 3, or 4 weeks, or for greater than 4 weeks, e.g., 5, 6, 7, or 8 weeks).

In one embodiment, administration of the inhibitor of PTEN and inhibitor of SOCS3 to a subject (e.g., in a single or in different pharmaceutical compositions, with or without an additional factor described herein) results in the inhibitors directly contacting an injured neuron in need of regeneration. In one embodiment, administration results in contacting neurons proximal to a site of neuronal injury. Neurons can be contacted at any point along their length (e.g., at the axon, dendrite and/or the cell body).

Administration to the subject can be by any one or combination of a variety of methods (e.g., parenterally, enterally and/or topically). The appropriate method(s) will depend upon the circumstances of the individual (e.g. the location of the target neuron(s), the condition of the individual, the desired duration of the contact, whether local or systemic treatment is desired). The administration can be by any methods described herein that will result in contact of sufficient inhibitor(s) to the target neuron to promote sustained survival, sustained regeneration, or a combination of both. For instance, parenteral, enteral and topical administration can be used. The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. Enteral administration involves the esophagus, stomach, and small and large intestines (i.e., the gastrointestinal tract). The phrases "systemic administration," "administered systemically", "peripheral administration" and "administered peripherally" as used herein mean the administration of a compound other than directly into the central nervous system, such that it enters the animal's system and, thus, is subject to metabolism and other like processes, for example, subcutaneous administration. Administration may be topical (including ophthalmic, vaginal, rectal, intranasal, epidermal, and transdermal), oral or pulmonary administration, e.g., by inhalation or insufflation, or intracranial, e.g., intrathecal or intraventricular, administration, topically to the eye, or by intraocular injection.

Specific routes of administration and the dosage regimen will be determined by skilled clinicians based on factors such as the exact nature of the condition being treated, the severity of the condition, and the age and general physical condition of the patient.

The invention also provides methods for promoting sustained survival, sustained regeneration, or a combination of both in a lesioned neuron of central nervous system neurons following an injury. The method involves administering to a subject a combination of the inhibitor of PTEN and inhibitor of SOCS3 to the subject to thereby contact the site of injury.

The term "administering" to a subject includes dispensing, delivering or applying an active compound in a pharmaceutical formulation to a subject by any suitable route for delivery of the active compound to the desired location in the subject to thereby contact the desired portion(s) of the neuron(s), (e.g., the injury, the injured neuron, or the site of desired outgrowth of the neuron). This includes, without limitation, delivery by either the parenteral or oral route, intramuscular injection, subcutaneous/intradermal injection, intravenous injection, buccal administration, transdermal delivery and administration by the rectal, colonic, vaginal, intranasal or respiratory tract route, intraocular, ocular. Another form of administration suitable for treatment of spinal cord injury is injection into the spinal column or spinal canal.

In one embodiment, the inhibitor(s) is contacted in vivo by introduction into the central nervous system of a subject, e.g., into the cerebrospinal fluid of the subject. In certain aspects of the invention, the inhibitor(s) is introduced intrathecally, e.g., into a cerebral ventricle, the lumbar area, or the cisterna magna. In another aspect, the inhibitor(s) is introduced intraocullarly, to thereby contact retinal ganglion cells or the optic nerve. Modes of administration are described in U.S. Pat. No. 7,238,529.

In one embodiment, administration occurs following neuronal injury in the subject, not prior to or at the time of neuronal injury.

In another embodiment of the invention, the inhibitor(s) formulation is administered into a subject intrathecally. As used herein, the term "intrathecal administration" is intended to include delivering an inhibitor(s) formulation directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of an inhibitor(s) to any of the above mentioned sites can be achieved by direct injection of the inhibitor(s) formulation or by the use of infusion pumps. For injection, the inhibitor(s) formulation of the invention can be formulated in liquid solutions, preferably in physiologically compatible buffers such as Hank's solution or Ringer's solution. In addition, the inhibitor(s) formulation may be formulated in solid form and re-dissolved or suspended immediately prior to use. Lyophilized forms are also included. The injection can be, for example, in the form of a bolus injection or continuous infusion (e.g., using infusion pumps) of the inhibitor(s) formulation.

In one embodiment of the invention, said inhibitor(s) formulation is administered by lateral cerebro ventricular injection into the brain of a subject in the inclusive period from the time of the injury to a time determined by the skilled practitioner (e.g., 100 hours). The injection can be made, for example, a burr hole made in the subject's skull. In another embodiment, said encapsulated therapeutic agent is administered through a surgically inserted shunt into the cerebral ventricle of a subject in the inclusive period from the time of the injury to a time determined by the skilled practitioner (e.g., 100 hours thereafter). For example, the injection can be made into the lateral ventricles, which are larger, even though injection into the third and fourth smaller ventricles can also be made.

In yet another embodiment, said inhibitor(s) formulation is administered by injection into the cisterna magna, or lumbar area of a subject in the inclusive period from the time of the injury to a time determined by the skilled practitioner (e.g., 100 hours thereafter). Administration can be continuous, or can be by repeated doses. In one embodiment, the repeated doses are formulated so that an effective amount of the inhibitors is continually present at the injury site.

Duration and Levels of Administration

The pharmaceutical composition, used in the method of the invention, contains a therapeutically effective amount of the inhibitor of PTEN and/or SOCS3. A "therapeutically effective amount" refers to an amount effective, at dosages and for periods of time necessary, to achieve the desired result (e.g., sustained neuronal survival, sustained neuronal outgrowth from lesioned or proximal neurons). A therapeutically effective amount of the inhibitor may vary according to factors such as the disease state, age, and weight of the subject, and the ability of the inhibitor (alone or in combination with one or more other agents) to elicit a desired response in the subject. Dosage regimens may be adjusted to provide the optimum therapeutic response. A therapeutically effective amount is also one in which any toxic or detrimental effects of the inhibitor(s) thereof are outweighed by the therapeutically beneficial effects.

The term "therapeutically effective amount" refers to an amount that is sufficient to effect a therapeutically reduction in a symptom associated with the neuronal injury, disease, disorder or condition described herein, when administered to a typical subject who has said injury, disease, disorder, condition. A therapeutically significant reduction in a symptom is, e.g. about 10%, about 20%, about 30%, about 40%, about 50%, about 60%, about 70%, about 80%, about 90%, about 100%, about 125%, about 150% or more as compared to a control or non-treated subject. In some embodiments the term "therapeutically effective amount" refers to the amount that is safe and sufficient to prevent or delay the development and further spread of neuronal injury, disease, or other disease symptoms. The amount can also cure or cause the disease, disorder or condition to go into remission, slow the course of, or otherwise inhibit progression by promoting sustained survival, sustained regeneration, or a combination of both of the lesioned or threatened neurons.

In one embodiment, the therapeutically effective amount is evidenced by the restoration of nerve function. Restoration of nerve function can be evidenced, for example, by restoration of nerve impulse conduction, a detectable increase in conduction action potentials, observation of anatomical continuity, restoration of more than one spinal root level, an increase in behavior or sensitivity, or a combination thereof.

Contacting of the injured neuron(s) (e.g., by administration to a subject) can be anytime following the injury. In one embodiment, the injured neuron is contacted within 96 hours of formation of the lesion on the neuron to be contacted, and more preferably within 72, 48, 24, or 12 hours. In one embodiment, the subject is administered one or both inhibitors prior to injury as a precautionary measure.

The treatment of a subject may likewise begin anytime following the injury. In one embodiment, the treatment progresses upon detection or suspicion of the injury. For example, the treatment can be begun at about 1 hr, 2 hr, 3 hr, 4 hr, 5 hr, 6 hr, 7 hr, 8 hr, 9 hr, 10 hr, 11 hr, 12, hr, 18 hr, or 24 hours post injury. Benefit is also expected to be had from treatment that takes place considerably longer after the injury. The injury may have occurred more than three months prior to the treatment, more than one month prior, more than three weeks prior to the treatment, or more than two weeks prior to the treatment, more than one week prior to the treatment or from between 1-6 days prior to the treatment.

Since the combined action of the inhibitors produces sustained survival and sustained regeneration in a lesioned neuron, significant benefit is expected to result from extended contacting of the inhibitors to the lesioned neuron. Such contacting can be achieved by extended administration of the inhibitors to the subject in need. As such, administration can take place for at least 2, 5, or 10 days. Even longer period of time are expected to also provide substantial benefit (e.g., for at least 2, 3, or 4 weeks). In some situations administration for greater than 4 weeks (e.g., 5, 6, 7, or 8 weeks) is expected to provide therapeutic results.

In one embodiment, the inhibitors (e.g., in the form of a pharmaceutical composition) described herein are contacted to the neuron, and/or administered to the subject in the period from the time of injury (for example within 24, 12, 6, 3, or 1 hours after the injury has occurred) to for at least 2, 5, or 10 days, or for at least 2, 3, or 4 weeks, or for greater than 4 weeks, e.g., 5, 6, 7, or 8 weeks). Useful longer period can be determined by the skilled practitioner.

In one embodiment, administration occurs following neuronal injury in the subject, not prior to or at the time of neuronal injury. In one embodiment, administration occurs prior to injury, as a precautionary measure.

Detection of Therapeutic Effects

The methods described herein can further comprise the further step of detecting a resultant regeneration of the axon. For in vitro applications, axonal regeneration may be detected by any routinely used method to assay axon regeneration such as a neurite outgrowth assay.

In one embodiment, the method of treatment further comprises a detecting step, such as the step of detecting a resultant improved recovery from the injury, or detecting a resultant promoted regeneration of the injured neuron. Such improvement can be detected directly using imaging methodologies such as MRI, or indirectly or inferentially, such as by neurological examination showing improvement in the targeted neural function. The detecting step may occur at any time point after initiation of the treatment, e.g. at least one day, one week, one month, three months, six months, etc. after initiation of treatment. In certain embodiments, the detecting step will comprise an initial neurological examination and a subsequent neurological examination conducted at least one day, week, or month after the initial exam. Improved neurological function at the subsequent exam compared to the initial exam indicates resultant axonal regeneration. The specific detection and/or examination methods used will usually be based on the prevailing standard of medical care for the particular type of neuron injury being evaluated (i.e. trauma, neurodegeneration, etc.).

Pharmaceutically Acceptable Compositions

In one embodiment, the combination of inhibitors of PTEN and SOCS3 which is administered in vivo to a subject is contained in one or more pharmaceutically acceptable compositions. The pharmaceutical composition or solution can further include one or more other exogenous agents (e.g., one or more axogenic factors) described herein as administered with or contacted in the presence of the inhibitors. The pharmaceutical composition may optionally be specifically formulated to exclude one or more such other agents. In one embodiment, the pharmaceutical composition consists essentially of the inhibitors of PTEN and SOCS3 and a pharmaceutically acceptable carrier. By the term "consists or consisting essentially of" is meant that the pharmaceutical composition does not contain any other active agents (e.g., modulators of neuronal outgrowth).

A pharmaceutical composition comprising an effective amount of an inhibitor of SOCS3 and an effective amount of an inhibitor of PTEN is encompassed by the present invention. The pharmaceutical composition comprises the respective inhibitors in the respective concentrations that are sufficient to promote sustained survival, sustained regeneration, or a combination of both to a lesioned neuron when administered at the appropriate dosage for the appropriate period of time, as discussed herein.

In one embodiment, the pharmaceutical composition of the invention can be provided as a packaged formulation. The packaged formulation may include a pharmaceutical composition of the invention in a container and printed instructions for administration of the composition for treating a subject having a neuronal injury, and/or disease, disorder or condition associated with neuronal injury, as described herein.

Pharmaceutical compositions are considered pharmaceutically acceptable for administration to a living organism. For example, they are sterile, the appropriate pH, and ionic strength, for administration. They generally contain the inhibitor(s) formulated in a composition within/in combination with a pharmaceutically acceptable carrier, also known in the art as excipients.

The pharmaceutically acceptable carrier is formulated such that it facilitates delivery of the active ingredient (e.g., the PTEN and SOCS3 inhibitors) to the target site. Such a carrier is suitable for administration and delivery to the target neuron. The pharmaceutically acceptable carrier will depend upon the location of the target neuron and the route of administration. For example, a typical carrier for intravenous administration of an agent is saline. The term "pharmaceutically acceptable carrier" includes, without limitation, any and all solvents, dispersion media, coatings, antibacterial and anti fungal agents, isotonic and absorption delaying agents, and the like that are physiologically compatible. For example, the carrier can be suitable for injection into the cerebrospinal fluid. The pharmaceutical composition can further be designed to provide protection of the inhibitor from unnecessary dispersion or degradation. The pharmaceutical composition may also contain additional ingredients such as stabilizers and disintegrants. Appropriate carriers and pharmaceutical compositions will be determined by the skilled practitioner.

In one embodiment, the pharmaceutical composition is easily suspended in aqueous vehicles and introduced through conventional hypodermic needles or using infusion pumps. Prior to introduction, the composition can be sterilized with, preferably, gamma radiation or electron beam sterilization, described in U.S. Pat. No. 436,742 the contents of which are incorporated herein by reference.

Additional examples of carriers are synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

In one embodiment, the pharmaceutically acceptable carrier comprises a polymeric matrix. The terms "polymer" or "polymeric" are art-recognized and include a structural framework comprised of repeating monomer units which is capable of delivering the inhibitor(s) such that treatment of a targeted condition, e.g., a nervous system injury, occurs. The terms also include co-polymers and homopolymers e.g., synthetic or naturally occurring. Linear polymers, branched polymers, and cross-linked polymers are also meant to be included.

For example, polymeric materials suitable for forming the pharmaceutical composition employed in the present invention, include naturally derived polymers such as albumin, alginate, cellulose derivatives, collagen, fibrin, gelatin, and polysaccharides, as well as synthetic polymers such as polyesters (PLA, PLGA), polyethylene glycol, poloxomers, polyanhydrides, and pluronics. These polymers are biocompatible with the nervous system, including the central nervous system, they are biodegradable within the central nervous system without producing any toxic byproducts of degradation, and they possess the ability to modify the manner and duration of the inhibitor(s) release by manipulating the polymer's kinetic characteristics. As used herein, the term "biodegradable" means that the polymer will degrade over time by the action of enzymes, by hydrolytic action and/or by other similar mechanisms in the body of the subject. As used herein, the term "biocompatible" means that the polymer is compatible with a living tissue or a living organism by not being toxic or injurious and by not causing an immunological rejection.

Polymers can be prepared using methods known in the art (Sandler. S. R.; Karo, W. Polymer Syntheses; Harcourt Brace: Boston. 1994; Shalaby, W.; Ikada, Y.; Langer, R.: Williams, J. Polymers of Biological and Biomedical Significance (ACS Symposium Series 540; American Chemical Society: Washington, D.C. 1994). Polymers can be designed to be flexible; the distance between the bioactive side-chains and the length of a linker between the polymer backbone and the group can be controlled. Other suitable polymers and methods for their preparation are described in U.S. Pat. Nos. 5,455,044 and 5,576,018, the contents of which are incorporated herein by reference.

The polymeric formulations are preferably formed by dispersion of the inhibitor(s) within liquefied polymer, as described in U.S. Pat. No. 4,883,666, the teachings of which are incorporated herein by reference or by such methods as bulk polymerization, interfacial polymerization, solution polymerization and ring polymerization as described in Odian G., Principles of Polymerization and ring opening polymerization, 2nd ed., John Wiley & Sons, New York, 1981, the contents of which are incorporated herein by reference. The properties and characteristics of the formulations are controlled by varying such parameters as the reaction temperature, concentrations of polymer and inhibitor, types of solvent used, and reaction times.

One or both of the inhibitors can be encapsulated in one or more pharmaceutically acceptable polymers, to form a microcapsule, microsphere, or microparticle, terms used herein interchangeably. Microcapsules, microspheres, and microparticles are conventionally free-flowing powders consisting of spherical particles of 2 millimeters or less in diameter, usually 500 microns or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two. In one aspect of the present invention, the mean average diameter is less than about 45 preferably less than 20 and more preferably between about 0.1 and 10 μm.

In another embodiment, the pharmaceutical composition comprises lipid-based formulations. Any of the known lipid-based drug delivery systems can be used in the practice of the invention. For instance, multivesicular liposomes (MVL), multilamellar liposomes (also known as multilamellar vesicles or "MLV"). unilamellar liposomes, including small unilamellar liposomes (also known as unilamellar vesicles or "SUV") and large unilamellar liposomes (also known as large unilamellar vesicles or "LUV"), can all be used so long as a sustained release rate of the encapsulated inhibitor(s) can be established. In one embodiment, the lipid-based formulation can be a multivesicular liposome system. Methods of making controlled release multivesicular liposome drug delivery systems is described in PCT Application Serial Nos. US96/11642, US94/12957 and US94/04490, the contents of which are incorporated herein by reference. The composition of the synthetic membrane vesicle is usually a combination of phospholipids, usually in combination with steroids, especially cholesterol. Other phospholipids or other lipids may also be used.

Examples of lipids useful in synthetic membrane vesicle production include phosphatidylglycerols, phosphatidylcholines, phosphatidylserines, phosphatidylethanolamines, sphingolipids, cerebrosides, and gangliosides. Preferably phospholipids including egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol are used.

In preparing lipid-based vesicles containing inhibitor(s), such variables as the efficiency of encapsulation, lability of the inhibitor, homogeneity and size of the resulting population of vesicles, inhibitor-to-lipid ratio, permeability, instability of the preparation, and pharmaceutical acceptability of the formulation should be considered (see Szoka, et al., Annual Reviews of Biophysics and Bioengineering, 9:467, 1980; Deamer, et al., in Liposomes, Marcel Dekker, New York, 1983, 27; and Hope, et al., Chem. Phys. Lipids, 40:89, 1986, the contents of which are incorporated herein by reference). [0059] In one, the pharmaceutical composition provides sustained delivery, e.g., "slow release" of the inhibitor(s) to a subject for at least one, two, three, or four weeks after the pharmaceutical composition is administered to the subject.

As used herein, the term "sustained delivery" is intended to include continual delivery of the inhibitors in vivo over a period of time following administration, preferably at least several days, a week or several weeks. Sustained delivery of the inhibitors can be demonstrated by, for example, the continued therapeutic effect of the inhibitors over time (e.g., by continued outgrowth of neurons over time). Alternatively, sustained delivery of the inhibitors may be demonstrated by detecting the presence of the inhibitors in vivo over time.

In one embodiment, the pharmaceutical composition provides sustained delivery of the inhibitor(s) thereof to a subject for less than 30 days after the inhibitor(s) is administered to the subject. For example, the pharmaceutical composition, e.g., "slow release" formulation, can provide sustained delivery of the inhibitor(s) to the subject for one, two, three or four weeks after the formulation is administered to the subject. Alternatively, the pharmaceutically composition may provide sustained delivery of the inhibitor(s) to a subject for more than 30 days after the formulation is administered to the subject.

Other Agents

The PTEN inhibitor and SOCS3 inhibitor can be contacted to the injured neuron in combination with, or prior or subsequent to, other agents (also referred to herein as additional agents) such as anti-inflammatory or anti-scarring agents, growth or trophic factors, denervation-induced cytokines, etc. In one embodiment, the lesion results from acute spinal cord injury and the method additionally comprises contacting the neuron with methylprednisolone sufficient to reduce inflammation of the spinal cord. In one embodiment, the inhibitors are administered in combination with trophic and/or growth factors (e.g., denervation-induced cytokines) known in the art to promote or enhance neuronal survival/regeneration, growth and/or differentiation. Examples include, without limitation, brain-derived neurotrophic factor (BDNF), ciliary neurotrophic factor (CNTF) (WO2011/066182), fibroblast growth factor (FGF), chondroitinase, nerve growth factor (NGF), NT-3 (Piantino et al, Exp Neurol. 2006 October; 201(2):359-67), inosine (Chen et al, Proc Natl Acad Sci USA. (2002) 99:9031-6; U.S. Pat. No. 6,551,612 to Benowitz; U.S. Pat. No. 6,440,455 to Benowitz; and US Pat Publ 20050277614 to Benowitz), oncomodulin (Yin et al, Nat Neurosci. (2006) 9:843-52; US Pat Publ 20050054558 to Benowitz; US Pat Publ 20050059594 to Benowitz; and U.S. Pat. No. 6,855,690 to Benowitz). Another such agent is an agent to remove extracellular matrix molecules (e.g., chondroitin sulphate proteoglycans) that are inhibitory to neuronal outgrowth, such as chondroitinase ABC (ChABC), which breaks up chondroitin sulphate proteoglycans.

In one embodiment, the inhibitors are administered in combination with one or more factors that facilitate neuronal synapse formation. Examples of such factors include, without limitation, activators of Rab3A, NMDA-I, synapsin-1, tetanus toxin receptor, BDNF-receptor and a GABA receptor. Such factors are described in U.S. Patent Application Publication 2008/0214458. Neuronal synapse formation can be modulated, for example, by modulating the activity of the transcriptional factor myocyte enhancer factor 2 (MEF2) (e.g., MEF2A), MEF2C, MEF2D, dMEF2, CeMEF2, Activating transcription factor 6 beta (ATF6), Estrogen related receptor alpha (ERR1), Estrogen related receptor beta (ERR2), Estrogen related receptor gamma (ERR3), Erythroblastosis virus E26 oncogene homolog 1 (ETS1), Forkhead box protein C2 (FOXC2), Gata binding factor 1 (GATA-1), Heat shock factor 1 (HSF1), HSF4, MLL3, Myeloblastosis oncogene homolog (MYB), Nuclear receptor coactivator 2 (NCOA2), Nuclear receptor corepressor 1 (NCOR1), Peroxisome proliferative activated receptor gamma (PPARg), SMAD nuclear interacting protein 1 (SNIP1), SRY-box containing protein 3 (SOX3), SOX8, SOX9, Sterol regulatory element-binding transcription factor 2 (SREBP2), or Thyroid hormone receptor beta-1 (THRB1) (described in U.S. Patent Application Publication 20100112600).

The other agent(s) can be administered to the same site or to a different site as the PTEN inhibitor and/or SOCS3 inhibitor. The other agent may be contacted to the same site of the neuron or to a different site of the neuron. In one embodiment, the PTEN inhibitor and/or the SOCS3 inhibitor is contacted to the neuron(s) at the neuron's region of origin in the brain (e.g., by administration to cortical neurons at the cerebral ventricle) and the other agent is contacted to the neuron at the site of injury (e.g., the lesioned axon such as a cortical spinal tract axon). Other combinations of site of contact and routes of administration discussed herein are also envisioned.

Devices

The invention also provides activator-eluting or activator-impregnated implantable solid or semi-solid devices. Examples of implantable devices include polymeric microspheres (e.g. see Benny et al., Clin Cancer Res. (2005) 11:768-76) or wafers (e.g. see Tan et al., J Pharm Sci. (2003) 4:773-89), biosynthetic implants used in tissue regeneration after spinal cord injury (reviewed by Novikova et al., Curr Opin Neurol. (2003) 6:711-5), biodegradable matrices (see e.g. Dumens et al., Neuroscience (2004) 125:591-604), biodegradable fibers (see e.g. U.S. Pat. No. 6,596,296), osmotic pumps, stents, adsorbable gelatins (see e.g. Doudet et al., Exp Neurol. (2004) 189:361-8), etc. Preferred devices are particularly tailored, adapted, designed or designated for implantation. The implantable device may contain one or more additional agents used to promote or facilitate neural regeneration. For example, in one embodiment, an implantable device used for treatment of acute spinal cord injury contains the activator and methylprednisolone or other anti-inflammatory agents. In another embodiment, the implantable device contains the activator and a nerve growth factor, trophic factor, or hormone that promotes neural cell survival, growth, and/or differentiation, such as brain-derived neurotrophic factor (BDNF), ciliary neurotrophic factor (CNTF), nerve growth factor (NGF), inosine, oncomodulin, NT-3, etc.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. A method of promoting sustained survival in a lesioned mature neuron, sustained regeneration in a lesioned mature neuron, sustained compensatory outgrowth in a mature neuron, or a combination thereof, comprising:
contacting the neuron with an effective amount of an inhibitor of PTEN and an effective amount of an inhibitor of SOCS3 to thereby promote sustained survival, sustained regeneration, and/or sustained compensatory outgrowth of the neuron.

2. The method of paragraph 1, wherein the lesioned mature neuron is the result of an acute injury.

3. The method of paragraph 2, wherein the acute injury is selected from the group consisting of crush, severing, and acute ischemia.

4. The method of paragraph 1, wherein the lesioned mature neuron is the result of chronic neurodegeneration.

5. The method of any one of paragraphs 1-4 wherein contacting first occurs within 24 hours of the injury 6. The method of any one of paragraphs 1-4, wherein contacting first occurs within 3 days of the injury.

7. The method of any one of paragraphs 1-4, wherein contacting first occurs within 6 days of the injury.

8. The method of any one of paragraphs 1-7, wherein contacting is continued for a period of time selected from the group consisting of 1 week after initiation, 2 weeks after initiation 3 weeks after initiation, 4 weeks after initiation, 5 weeks after initiation, 6 weeks after initiation, 7 weeks after initiation, and 8 weeks after initiation.

9. The method of any one of paragraphs 1-8, wherein contacting occurs in vivo.

10. The method of any one of paragraphs 1-8, wherein contacting occurs in vitro.

11. The method of any one of paragraphs 1-10, wherein the neuron is human.

12. A method of treating a subject for a CNS lesion, comprising:
administering to the subject a therapeutically effective amount of an inhibitor of PTEN and a therapeutically effective amount of an inhibitor of SOCS3, wherein administering results in contacting one or more target CNS neurons of the subject with the inhibitor of PTEN and the inhibitor of SOCS3, to thereby promote sustained survival, sustained regeneration, sustained compensatory outgrowth, or a combination thereof in the CNS neurons.

13. The method of paragraph 12, wherein the subject is a human.

14. The method of any one of paragraphs 1-13, wherein the inhibitor of PTEN is selected from the group consisting of:
(a) potassium bisperoxo(bipyridine)oxovanadate (V) (bpV (bipy));
(b) dipotassium bisperoxo(5-hydroxypyridine-2-carboxyl) oxovanadate (V) (bpV(HOpic));
(c) potassium bisperoxo(1,10-phenanthroline)oxovanadate (V), (bpV(phen));
(d) dipotassium bisperoxo(picolinato)oxovanadate (V), (bpV(pic)); and
(e) combinations thereof.

15. The method of any one of paragraphs 1-14, wherein the inhibitor of SOCS3 is selected from the group consisting of SOCS3-specific hpRNA, siRNA, antisense SOCS3, dominant negative SOCS3, and combinations thereof.

16. The method of any one of paragraphs 12-15, wherein the CNS lesion results from an acute injury.

17. The method of paragraph 16, wherein the acute injury is selected from the group consisting of crush, severing, and acute ischemia.

18. The method of any one of paragraphs 16-17 wherein administration first occurs within 24 hours of the injury 19. The method of any one of paragraphs 16-17, wherein administration first occurs within 3 days of the injury.

20. The method of any one of paragraphs 16-17, wherein administration first occurs within 6 days of the injury.

21. The method of paragraph 12, wherein the CNS lesion results from chronic neurodegeneration.

22. The method of paragraph 12, wherein the CNS lesion results from a traumatic injury.

23. The method of paragraph 12 wherein the CNS lesion results from a traumatic brain injury.

24. The method of paragraph 12 wherein the CNS lesion results from a stroke.

25. The method of paragraph 12 wherein the lesioned CNS neuron is in the optic nerve.

26. The method of paragraph 12 wherein the CNS lesion results from an acute spinal cord injury.

27. The method of paragraph 12 wherein the lesioned CNS neuron is in the spinal cord of a patient, and the inhibitor is intrathecally administered to the patient.

28. The method of paragraph 12 wherein lesioned CNS neuron is a sensory neuron.

29. The method of any one of paragraphs 1-28 wherein the inhibitor is administered intravenously.

30. The method of any one of paragraphs 1-28 wherein the inhibitor is administered intrathecally.

31. The method of any one of paragraphs 1-28 wherein the inhibitor is administered ocularly.

32. The method of any one of paragraphs 1-28 wherein the inhibitor is administered locally at the neuron.

33. The method of any one of paragraphs 1-32, wherein an additional agent is administered to the subject.

34. The method of paragraph 33, wherein the additional agent is selected from the group consisting of inosine, oncomodulin, BNDF, NGF, CNTF, and combinations thereof.

35. A device for promoting sustained survival of a lesioned mature neuron, sustained regeneration of a lesioned mature neuron, compensatory outgrowth of a neuron, or a combination thereof, comprising a reservoir loaded with a pre-measured and contained amount of a therapeutically effective amount of an inhibitor of PTEN and an inhibitor of SOCS3, and specifically adapted for implementing the method of paragraph 12.

36. A pharmaceutical composition comprising a therapeutically effective amount of an inhibitor of SOCS3 and a therapeutically effective amount of an inhibitor of PTEN.

The invention is further illustrated by the following examples, which should not be construed as further limiting.

EXAMPLES

Example 1

During development axons reach their targets first through de novo outgrowth in embryos, followed by "networked growth" in which axons elongate with termini tethered to their targets. As animals increase in body size during postnatal and adolescent stages, the distance resulted from the "networked growth" could be much longer than that traveled by the initial de novo growth. After injury in the adult CNS, regenerating axons need to carry out de novo growth over relatively vast distances to reach their targets. Thus, the robustness of axon regeneration, in terms of both speed and duration of axon regrowth, is critical for making functional reconnections in adulthood. Approaches that have been shown to promote axon regeneration in the adult CNS include reducing extracellular inhibitory activity and increasing intrinsic growth ability[1-9]. However, the extents of axon regeneration observed in these studies are still limited. For example, previous studies demonstrated that the injured optic nerve could undergo significant axon regeneration after conditional deletion of PTEN or SOCS3 in adult RGCs, but the regrowth only occurred during the first 2 weeks post-injury, and then subsided afterwards[1,2].

Results

To identify a strategy for promoting sustained robust axon regeneration, the effects of deleting both PTEN and SOCS3 in adult RGCs on optic nerve regeneration was assessed. Adeno-associated viruses (AAV)-Cre (AAV-GFP as a control) were injected into the vitreous body of $PTEN^{f/f(10)}$, or $SOCS3^{f/f(11)}$, or $PTEN^{f/f}/SOCS3^{f/f}$ mice to delete the floxed genes 2 weeks prior to optic nerve injury. In addition, ciliary neurotrophic factor (CNTF) was applied intravitreously to the $SOCS3^{f/f}$ or $PTEN^{f/f}/SOCS3^{f/f}$ mice, as this enhances axon regeneration induced by SOCS3 deletion[2].

Figure 1B:
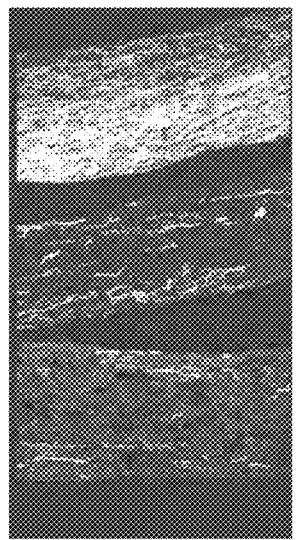
FIG. 1A-FIG. 1E show experimental results that indicate the synergistic effects of double deletion of PTEN and SOCS3 on axon regeneration observed at 4 weeks after injury. (A) Images of the optic nerve sections showing CTB-labeled axons in AAV-Cre-injected SOCS3$^{f/f}$ with CNTF (SOCS3$^{-/-}$), PTEN$^{f/f}$(PTEN$^{-/-}$), or PTEN$^{f/f}$/SOCS3$^{f/f}$ with CNTF (PTEN$^{-/-}$/SOCS3$^{-/-}$) mice. Asterisks: lesion sites. (B) High-magnification images of the boxed area in (A), which is about 1.5-2.0 mm from the lesion sites. (C) Regenerating axons at the optic chiasm. (D) Estimated numbers of regenerating axons. There was a significant difference between PTEN$^{-/-}$/SOCS3$^{-/-}$ group and others. ♦-PTEN$^{-/-}$/SOCS3$^{-/-}$; ■-PTEN$^{-/-}$; ▲-SOCS3$^{-/-}$; X-WT; *: p<0.001, ANOVA, Bonferroni's post hoc test. (E) Percentages of TUJ1-positive RGCs in each group compared to that in the intact retinas. *: p<0.001, ANOVA, Tukey's post hoc test. N=7-8 per group. Error bars, s.d. Scale bars: 200 μm.
Figure 1C:
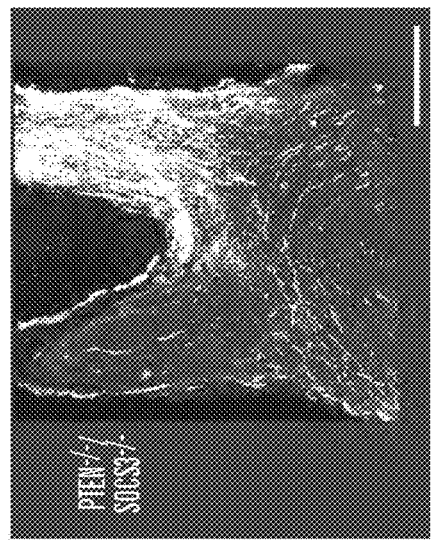
Figure 1A:
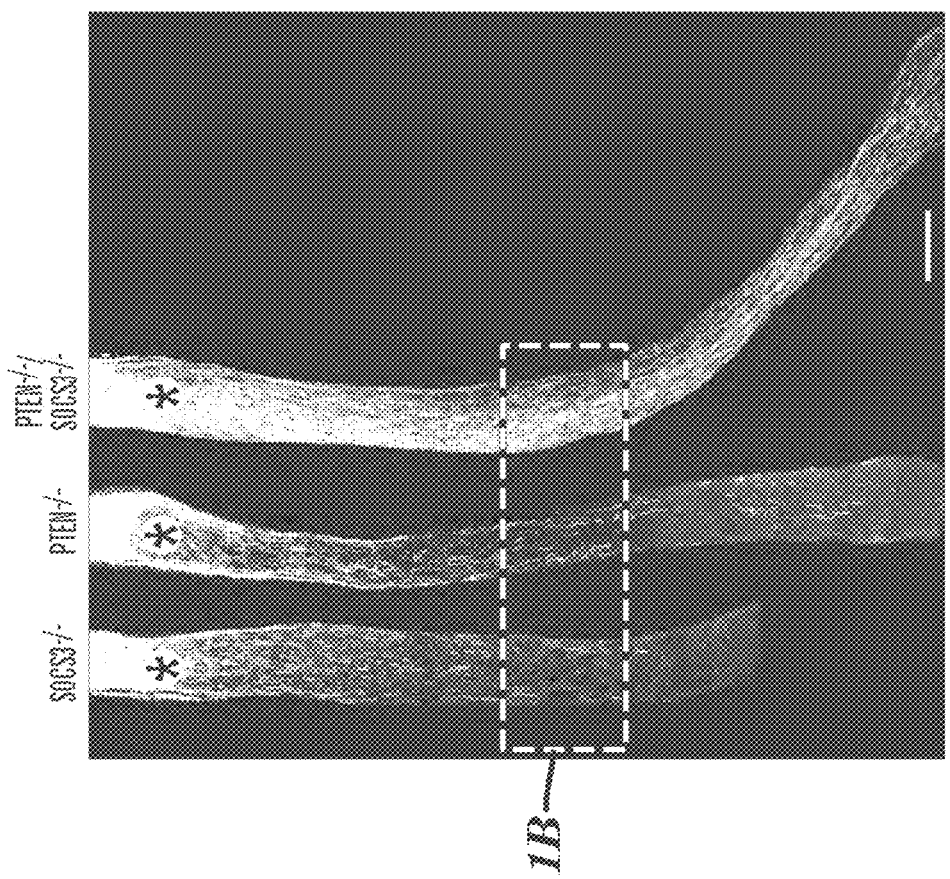
Figure 6A:
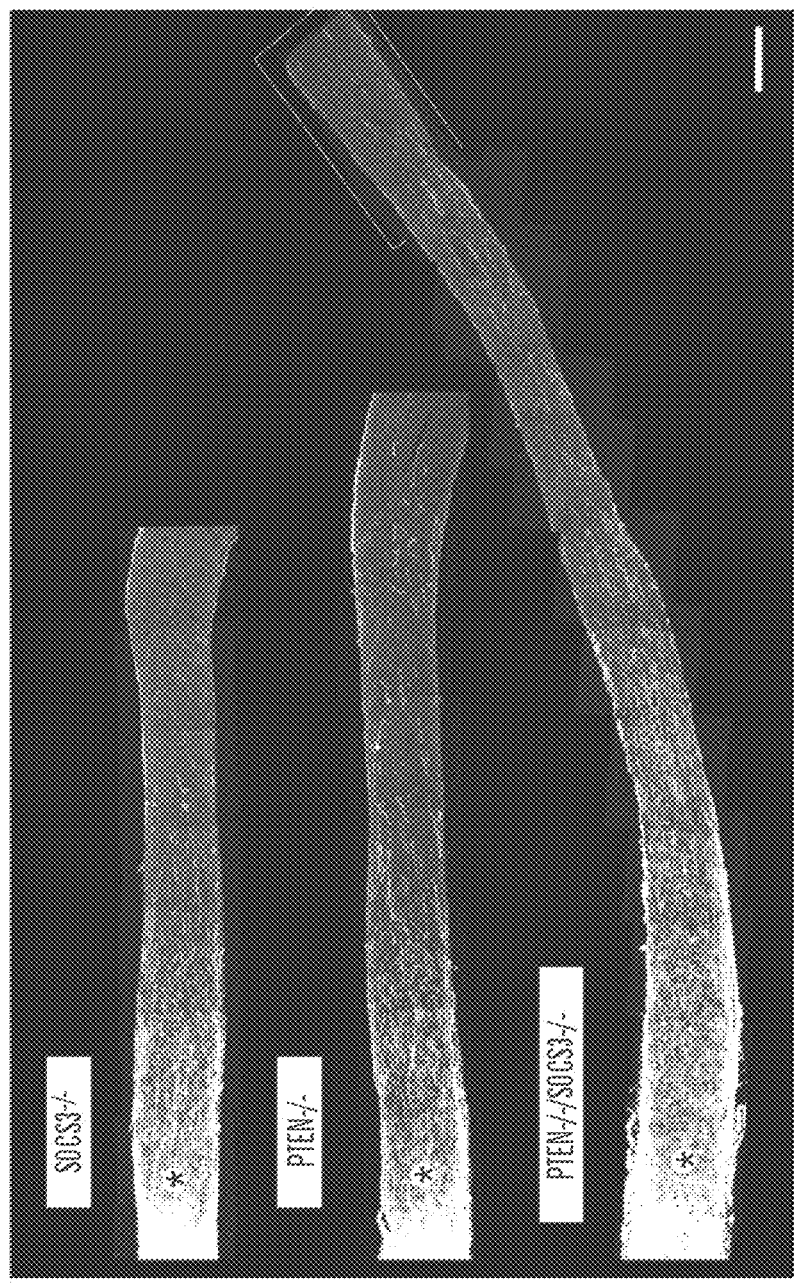
FIG. 6A-FIG. 6C show experimental results that indicate axon regeneration is observed at 2 weeks after an optic nerve injury. (A) Representative confocal images of the optic nerve sections showing that CTB labeled axons in AAV-Cre-injected SOCS3$^{f/f}$ with CNTF (SOCS34$^{-/-}$), PTEN$^{f/f}$ (PTEN$^{-/-}$), or PTEN$^{f/f}$/SOCS3$^{f/f}$ with CNTF (PTEN$^{-/-}$/SOCS3$^{-/-}$) mice. Asterisks indicate lesion sites. (B) Quantification of axon regeneration seen in (A) (♦) PTEN$^{-/-}$/SOCS3$^{-/-}$; (■) PTEN$^{-/-}$; (▲) SOCS3$^{-/-}$; (X) WT. The numbers of regenerating axons in the PTEN$^{-/-}$/SOCS3$^{-/-}$ group are significantly higher than each individual mutant group at all distance measured (up to 3 mm away from the lesion site). *: p<0.001, ANOVA, Bonferroni's post hoc test; N=6 per group. Error bars, s.d. (C) Quantification of RGC survival as measured by TUJ1 staining. All three mutant groups had significantly higher numbers of TUJ1+ RGCs after injury compared to the injured wild type group. *: p<0.001, ANOVA, Tukey's post hoc test. Error bars, s.d. Scale bars: 200 urn.
Figure 6C:
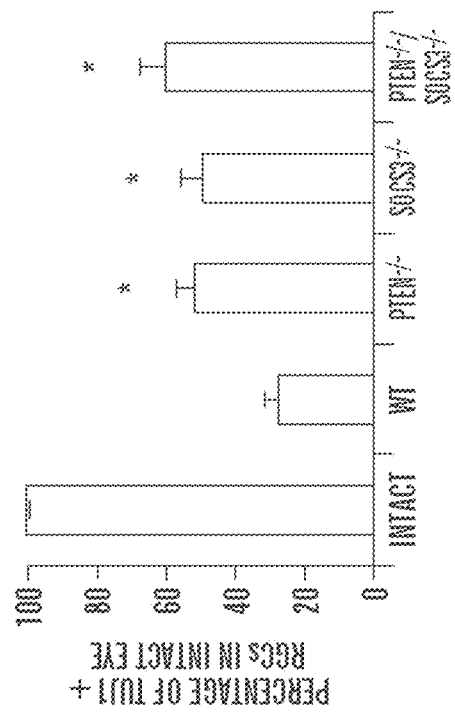
Figure 6B:
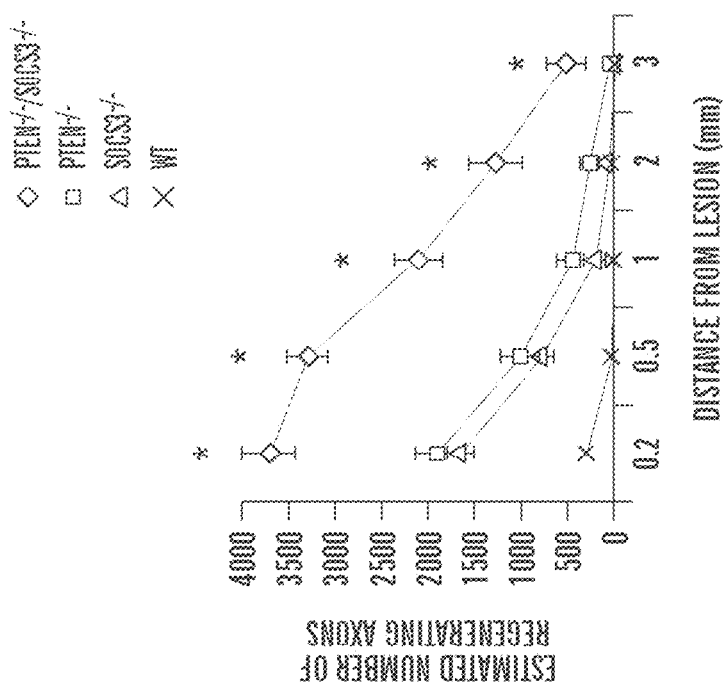
Figure 7A:
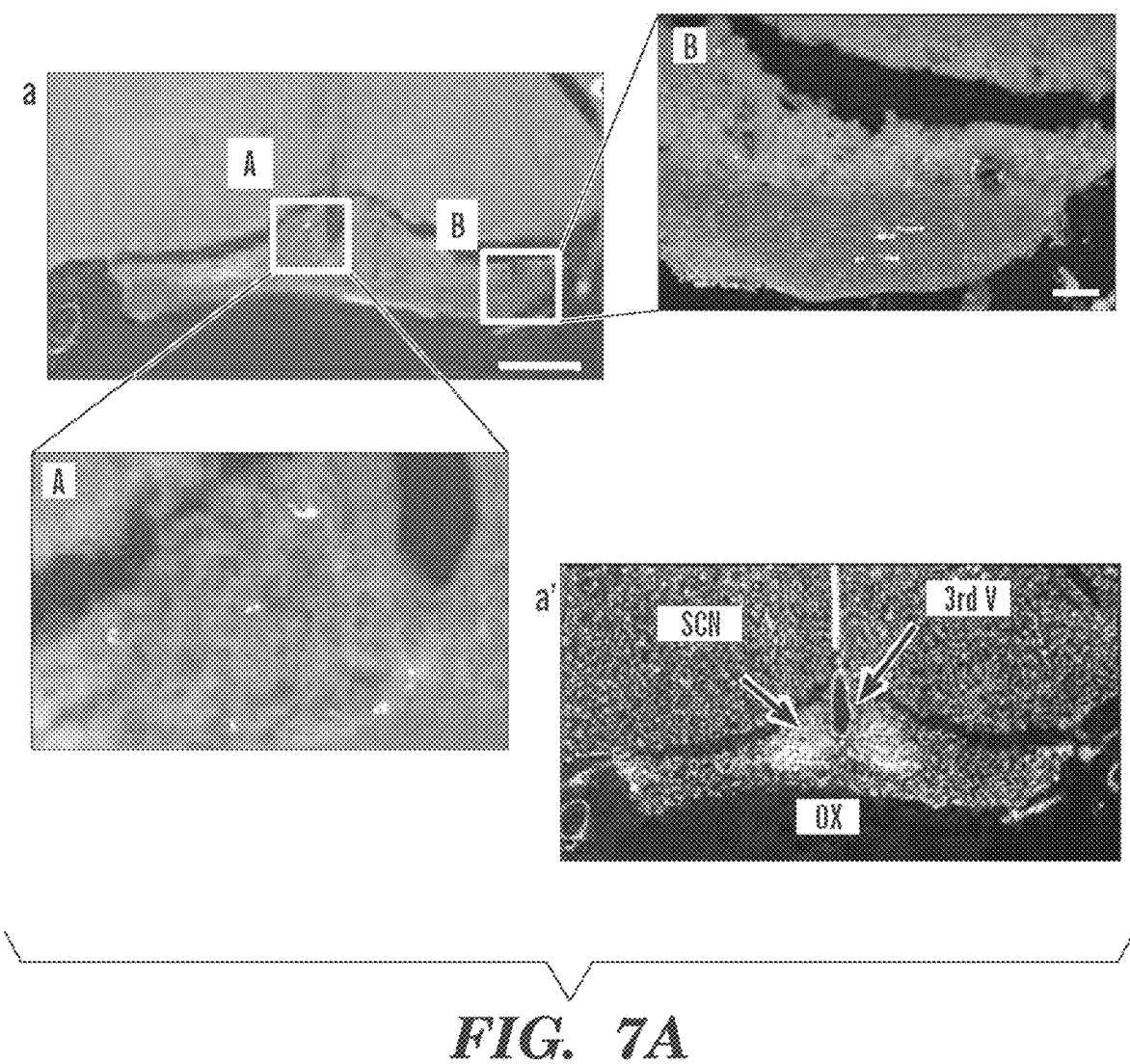
FIG. 7A-FIG. 7B are experimental results that show the regenerating axons in the brain areas after optic nerve injury in the adult mice with PTEN and SOCS3 double deletion and CNTF treatment at 4 weeks post-injury. (a) A few CTB-labeled axons could be seen in the suprachiasmatic nuclei (SCN) area (A), as indicated by Dapi nuclear staining (a'). (B) Regenerating axons in the optic tract at this anatomical level. (b) More caudally, regenerating axons could be seen at around the optic tract brain entry zone (A, A') and occasionally in area more medially (B). SCN: superachiasmic nuclei; 3rd V: third ventricle; OX: optic chiasm; EZ: entry-zone. Scale bars: 500 urn in (a, a' and b). 50 urn in (A, A' and B).
Figure 7B:
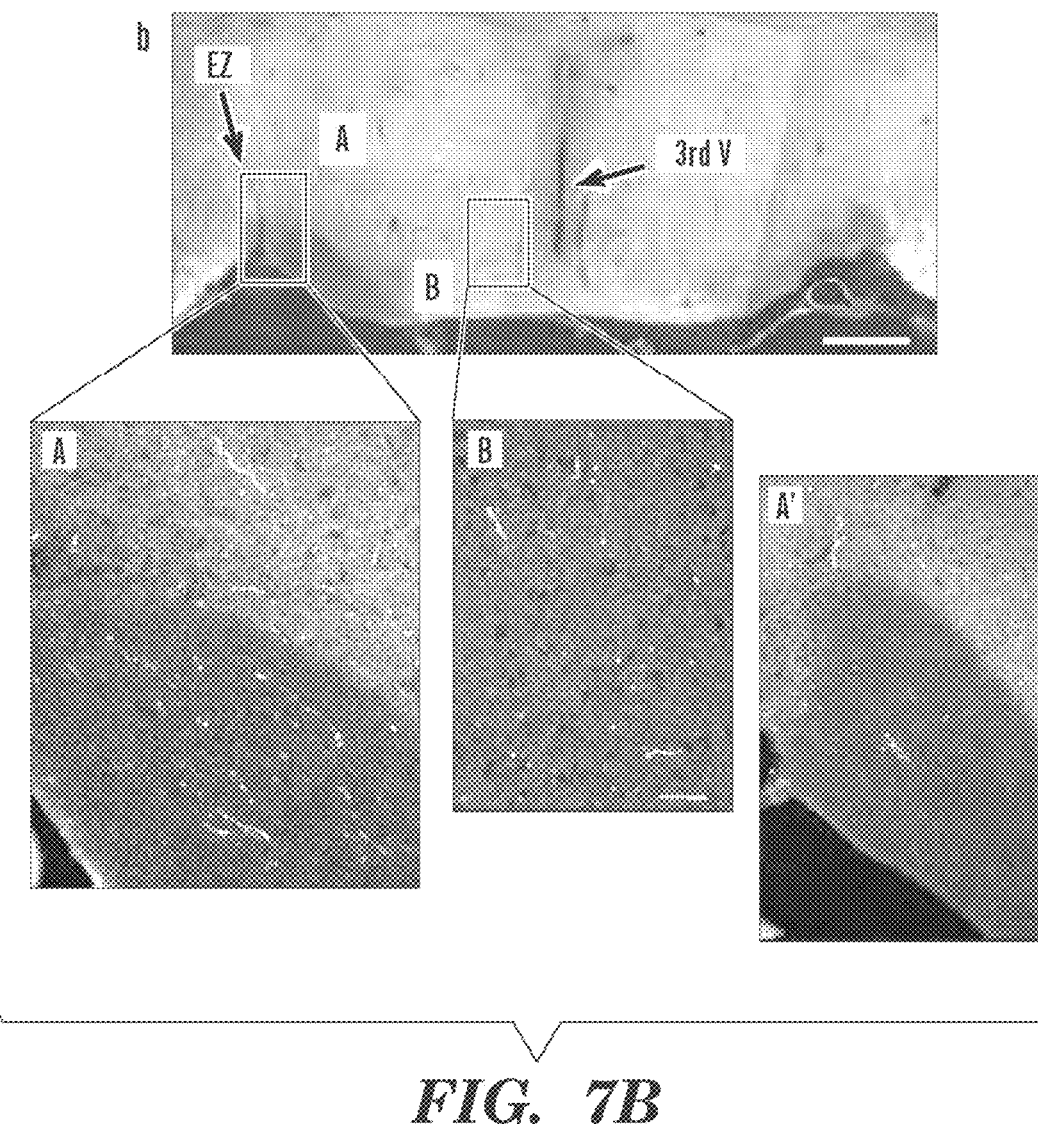

At 2 weeks post-injury, a significant increase in axon regeneration in the double knockout group was observed (FIG. 6 a-b). The synergistic effects of the double deletion became even more dramatic at 4 weeks after injury (FIG. 1). At 2 mm distal to the lesion site, deletion of both genes resulted in more than 10-fold increase in the number of regenerating axons compared to deletion of either gene alone (FIG. 1a-d). In the double mutants, more than 20% of the regenerating axons reached the region proximal to the optic chiasm (FIG. 1c). Among the regenerating axons passing the chiasm, some crossed the midline and projected to the contralateral side, while others remained ipsilateral. Occasionally, a few axons could be seen projecting into the opposite uninjured optic nerve (FIG. 1c). Interestingly, several regenerating axons could grow even further, reaching the optic tract brain entry zone and in the hypothalamus, the suprachiasmatic nuclei area (FIG. 7).

Figure 1E:
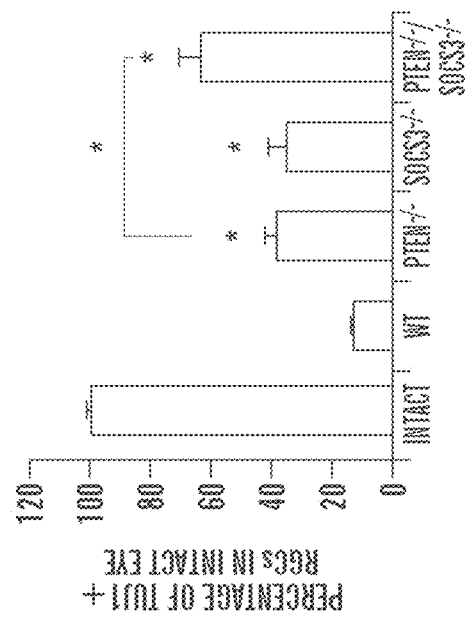
Figure 1D:
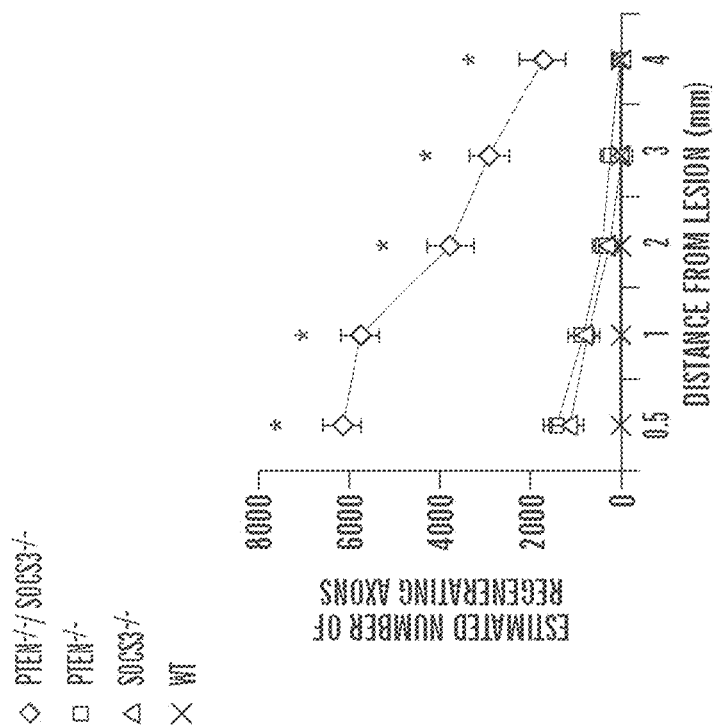
Figure 2A:
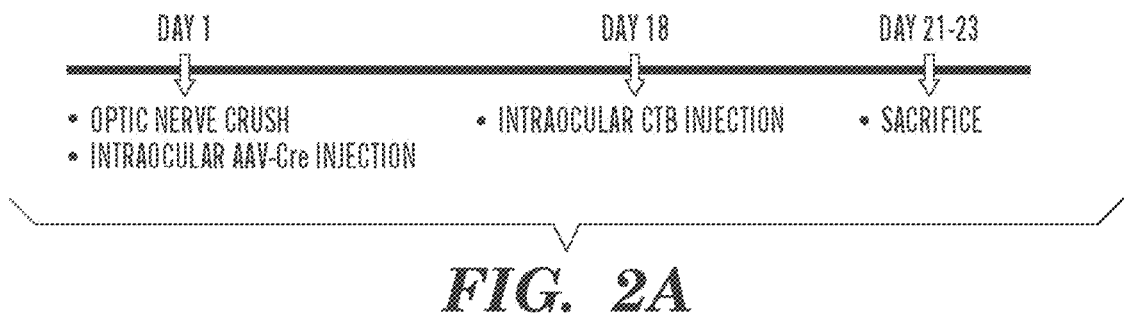
FIG. 2A-FIG. 2D show experimental results that indicate the synergistic effects of double deletion of PTEN and SOCS3 on optic nerve regeneration in a delayed treatment paradigm. (A) Scheme of the experiment. (B) Images of the optic nerve sections showing CTB-labeled axons in AAV-Cre-injected SOCS3$^{f/f}$ with CNTF (SOCS3$^{-/-}$), PTEN$^{f/f}$ (PTEN$^{-/-}$), or PTEN$^{f/f}$/SOCS3$^{f/f}$ with CNTF (PTEN$^{-/-}$/SOCS3$^{-/-}$) mice. Asterisks: lesion sites. (C) Extensive axon regeneration is only evident in double mutants. Top panel shows the entire optic nerve up to the chiasm. Bottom panels show high-magnified areas (A and B) as indicated in the top panel. OX: optic chiasm. (D) Estimated numbers of regenerating axons. At all distances quantified, there was a significant difference between the PTEN$^{-/-}$/SOCS3$^{-/-}$ (represented by the top line on the graph) group and the remaining groups (PTEN$^{-/-}$; SOCS3$^{-/-}$; WT, respectively represented as the next lower lines on the graph, in descending order). *: p<0.001, ANOVA, Bonferroni's post hoc test. N=5-6 per group. Error bars, s.d. Scale bars: 100 μm.
Figure 2B:
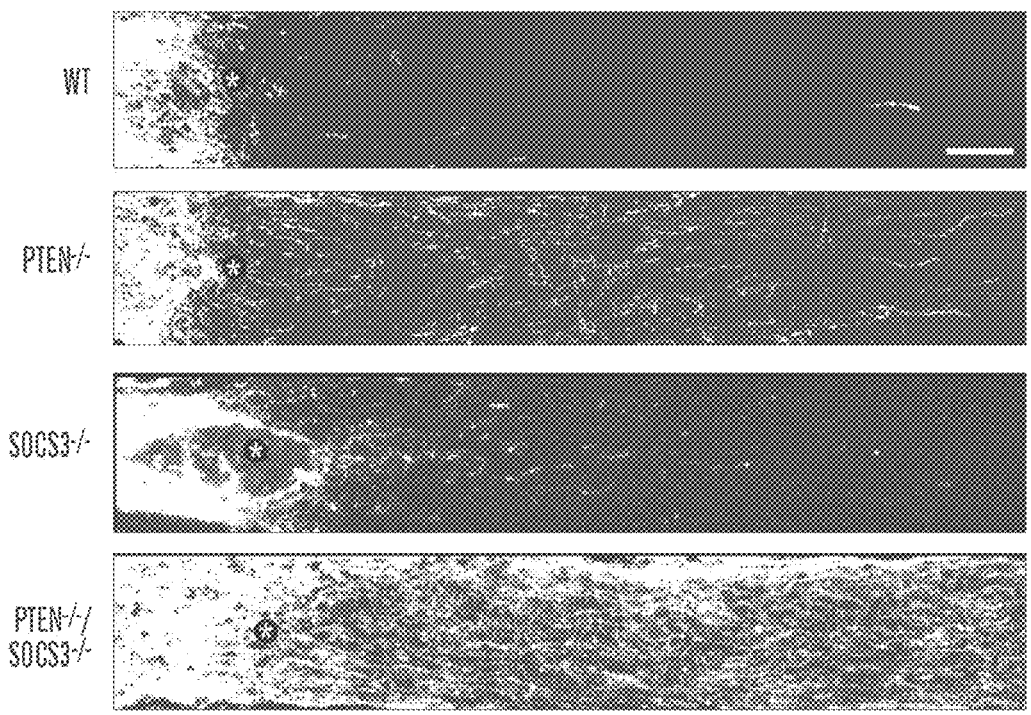
Figure 2C:
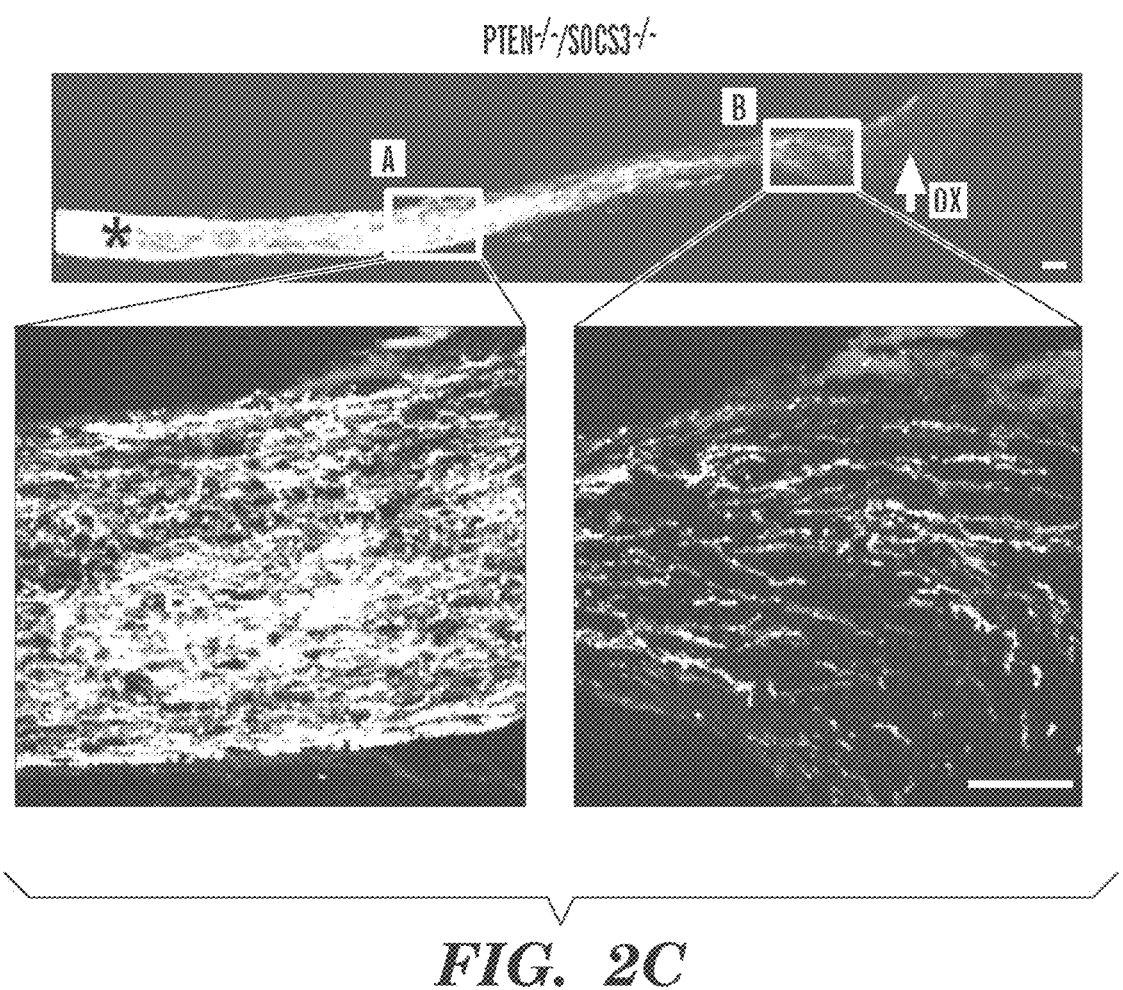
Figure 2D:
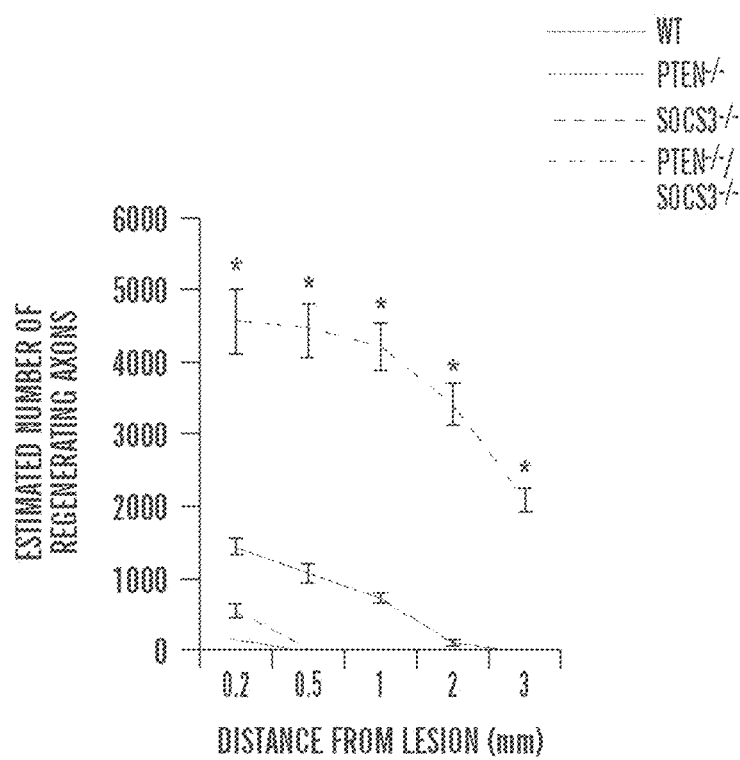

Compared to wild type animals, all three mutant groups showed significantly increased RGC survival after injury. At 2 weeks after injury, the survival was comparable among the three mutant groups (FIG. 6c). At 4 weeks after injury however, the number of surviving RGCs declined in the PTEN or SOCS3 single mutants, while the survival rate was maintained in the double mutants (FIG. 1e).

Figure 8A:
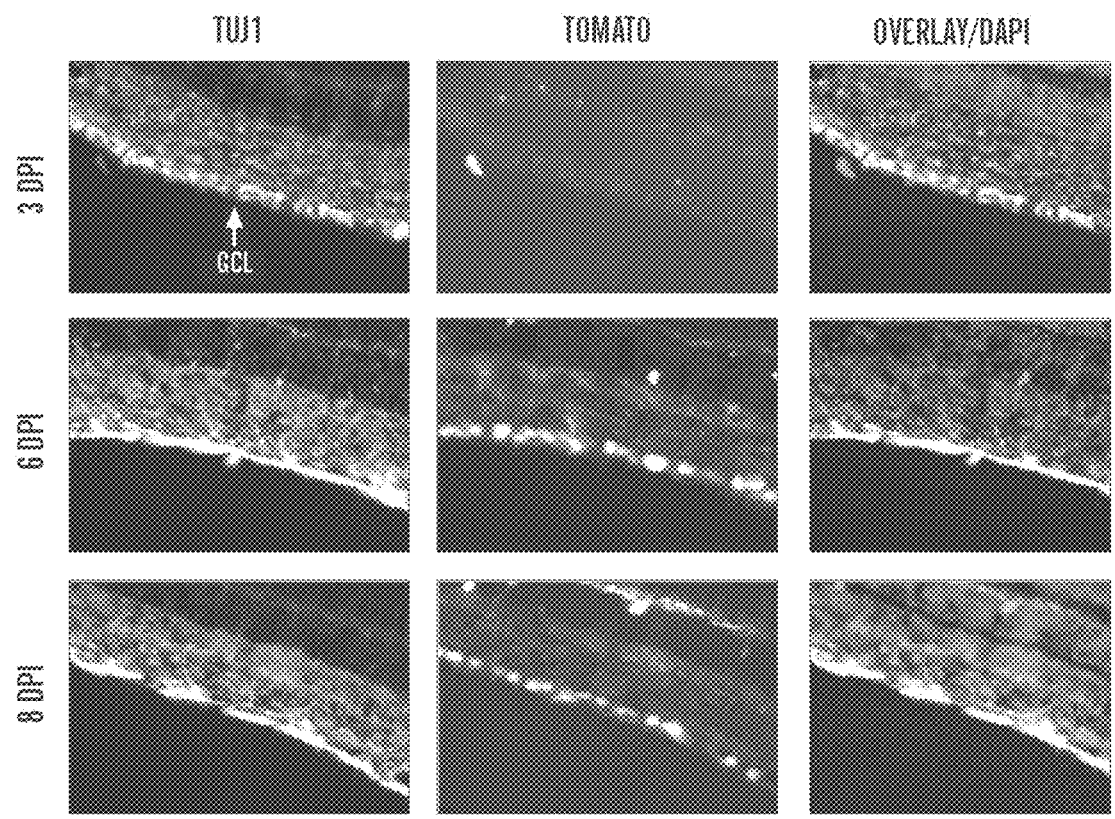
FIG. 8A-FIG. 8C are experimental results that show the characterization of the delayed treatment experiment. (A)
Figure 8B:
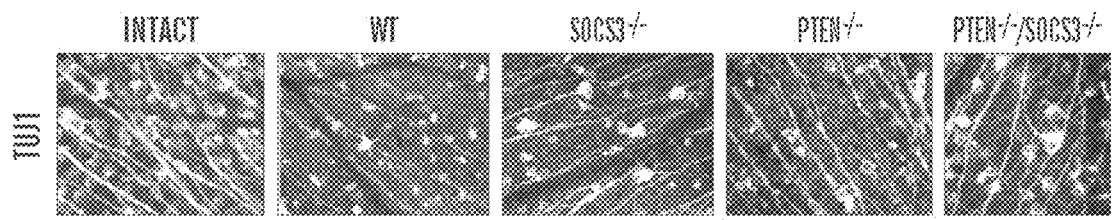
Figure 8C:
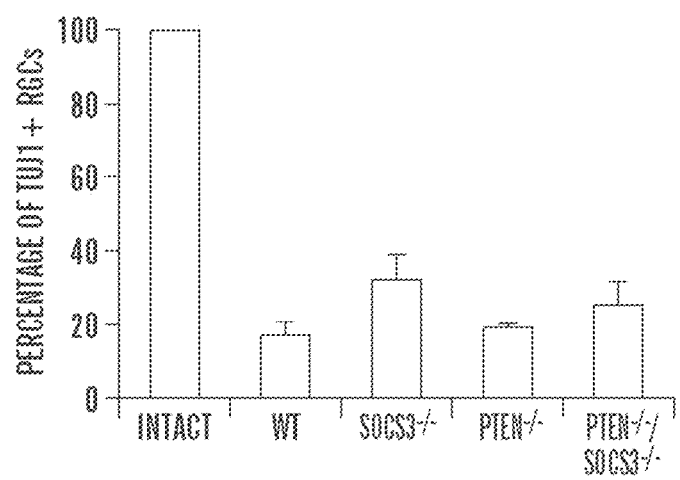

To mimic a clinically relevant scenario, whether a delayed deletion of PTEN and/or SOCS3 still promoted sustained optic nerve regeneration was examined. Thus, intravitreal AAV-Cre injection was performed immediately after optic nerve injury (FIG. 2). It takes at least 3-6 days for Cre-dependent reporter expression to be observed (FIG. 8a). RGC survival and axon regeneration was examined 3 weeks post-injury in these animals. Despite similar survivals in all groups (FIG. 8b-c), double and single mutants showed significant differences in the extents of axon regeneration (FIG. 2). At 0.5 mm distal to the lesion site, up to 20-fold more regenerating axons were seen in double mutants, compared to individual single mutants. Thus, adult RGCs with concomitant deletion of PTEN and SOCS3 can activate a program for sustained de novo axon growth after injury.

Figure 3A:
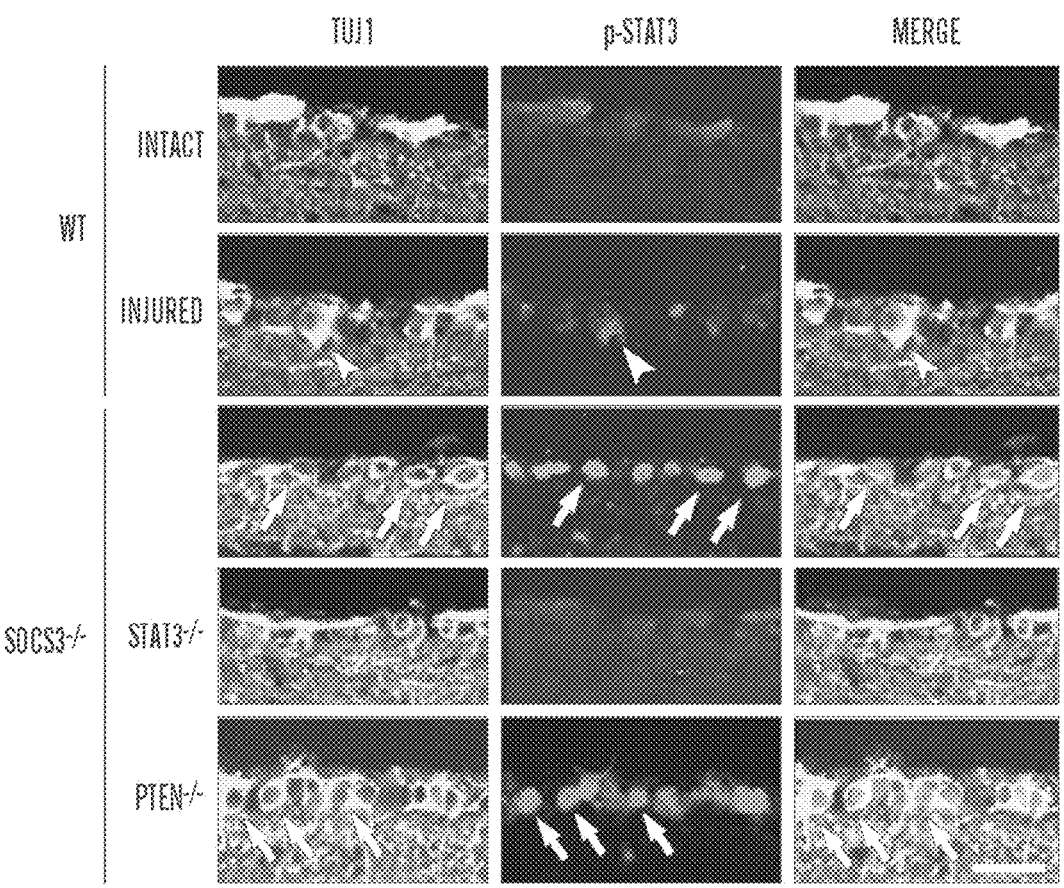
FIG. 3A-FIG. 3D show experimental results that indicate STAT3 in axon regeneration is induced by SOCS3 deletion. (A) Images showing signals detected with TUJ1 or anti-p-STAT3 antibodies in the retinal sections from intact or 1-day-post-injury mice. (B). Percentage of RGCs with nuclear phospho-STAT3 signals. N=3-4 per group. *: p<0.001, ANOVA, Dunnett's post hoc test. (C, D) Images (C) and quantification (D) of optic nerve sections showing regenerating axons in each group at 14 days post-injury. By Bonferroni's post hoc test, regenerating axons in SOCS3$^{-/-}$/STAT3$^{-/-}$ double mutants were significantly less than those in the SOCS3$^{-/-}$ mutants at 0.2-2.0 mm from lesion site (p<0.01; N=5 per group). ▲-SOCS3$^{-/-}$; ♦-SOCS3$^{-/-}$/STAT3$^{-/-}$; ■-STAT3$^{-/-}$; X-WT; Error bars, s.d. Scale bars: 50 μm in (A), 100 μm in (C).
Figure 3B:
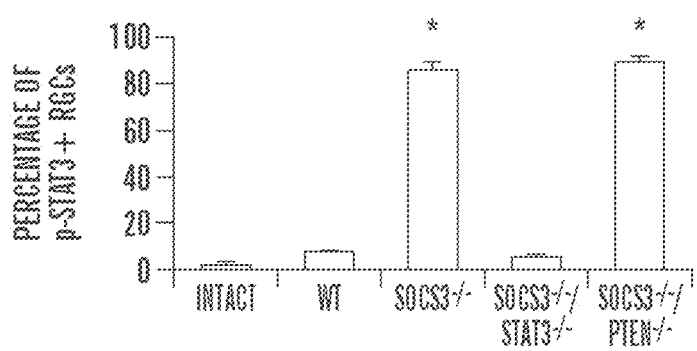

What mechanism(s) contribute to the synergy produced by concurrent deletion of PTEN and SOCS3 was then examined. While mTOR activation is likely to be a major mediator of PTEN deletion[1], the regeneration phenotype of SOCS3 deletion is dependent on gp130, a shared receptor components for cytokines[12,13]. However, multiple downstream effectors have been implicated in cytokines-gp130 signaling[12-15]. Because of a suggested relevance to axon regeneration[16-18], the specific involvement of the transcription factor STAT3, a major target of the JAK/STAT pathway[19] was tested. Upon phosphorylation-mediated activation, STAT3 accumulates in the nucleus to initiate transcription[19]. By immunostaining with anti-phospho-STAT3, phospho-STAT3 expression was found to be rarely detectable in intact RGCs. In wild type mice, optic nerve injury increased phospho-STAT3 levels in RGCs, but such signals were mainly localized in the cytosol (FIG. 3a, b). In contrast, phospho-STAT3 was evident in the nuclei of axotomized RGCs with both SOCS3 single and SOCS3/PTEN double mutants (FIG. 3a, b), suggesting the activation of STAT3 under these conditions.

Figure 3C:
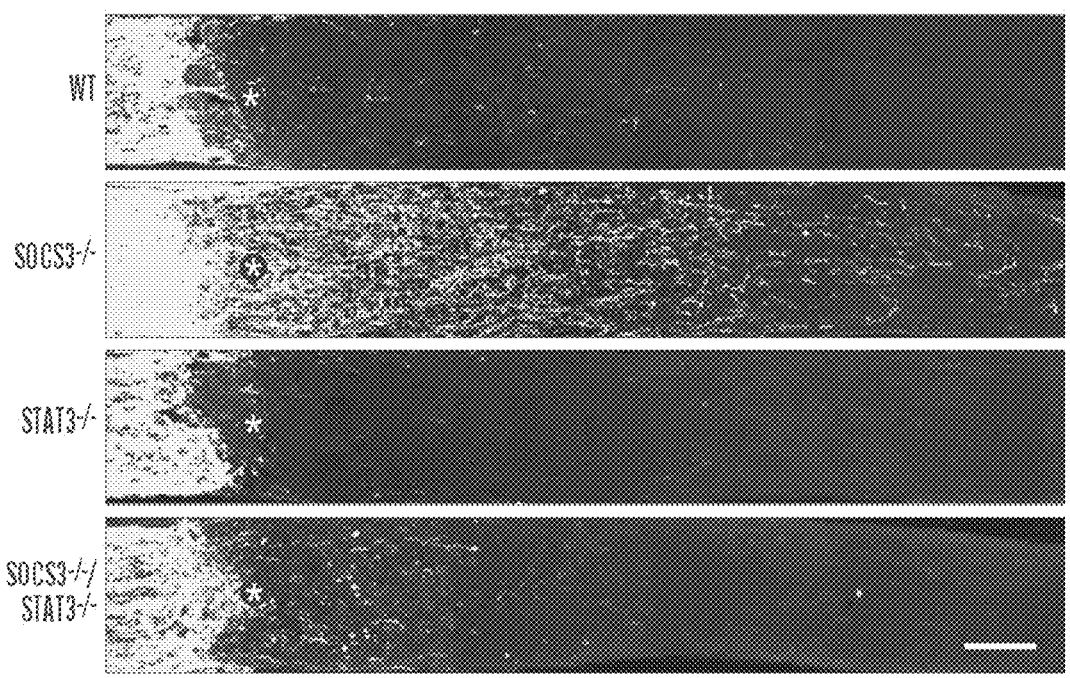
Figure 3D:
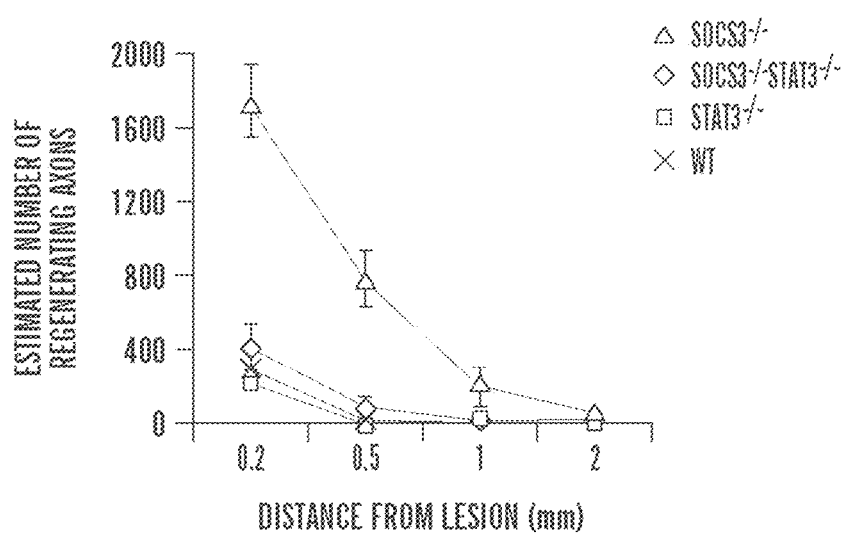

The contribution of STAT3 to the axon regeneration induced by SOCS3 deletion and CNTF administration was then evaluated. Deletion of STAT3 had no significant effects on RGC survival (FIG. 9) and axon regeneration (FIG. 3c). However, double deletion of STAT3 and SOCS3 abolished injury-induced phospho-STAT3 signal (FIG. 3a, b), RGC survival (FIG. 9), and axon regeneration (FIG. 3c, d) seen in SOCS3 single mutants, suggesting that STAT3 is a critical mediator of SOCS3 regulated axon regeneration and RGC survival.

Figure 4A:
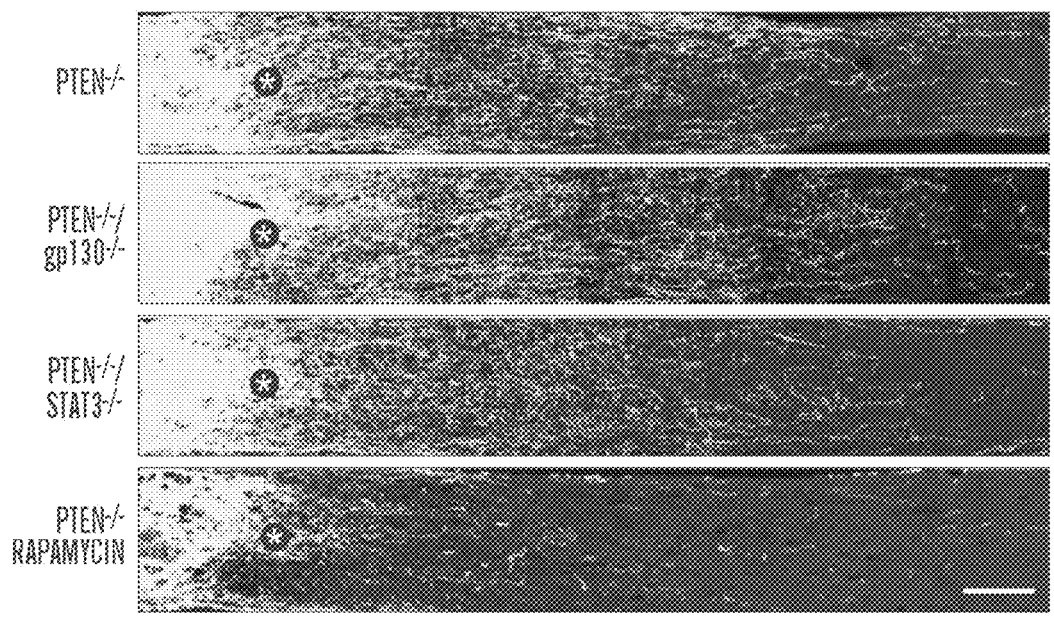
FIG. 4A-FIG. 4D show experimental results that indicate the independence of PTEN- and SOCS3-regulated pathways. (A, B) Images of optic nerve sections from PTEN$^{-/-}$ and various PTEN$^{-/-}$ combined groups (A) or SOCS3$^{-/-}$ mutants with or without rapamycin treatment (B) at 14 days post-injury. (C, D) Quantification of regenerating axons shown in (A) and (B) respectively. (C) Axon regeneration in either (■) PTEN$^{-/-}$/gp130$^{-/-}$ or (▲) PTEN$^{-/-}$/STAT3$^{-/-}$ group was comparable to that in (♦) PTEN$^{-/-}$, but was significantly reduced in the (+) PTEN$^{-/-}$ group with rapamycin (p<0.01, ANOVA, Bonferroni's post hoc test; N=5 per group) (●) WT; (X) STAT3$^{-/-}$. (D) Rapamycin treatment did not significantly reduce the number of regenerating axons in (♦) SOCS3$^{-/-}$ mice (N=6 per group) (■) SOCS3$^{-/-}$ plus rapamycin; (▲) WT. Error bars, s.d. Scale bars: 100 μm.

Possible interactions of the PTEN- and SOCS3-regulated pathways on optic nerve regeneration were then examined. Similar to wild type, phospho-STAT3 expression in PTEN deleted RGCs after injury was rarely detectable (FIG. 10), arguing against STAT3 activation after PTEN deletion. Importantly, the extents of axon regeneration and RGC survival were similar in the animals with PTEN single deletion and PTEN/STAT3 or PTEN/gp130 double deletion (FIG. 4a, c and FIG. 11a, b), suggesting that STAT3 is unlikely to be an important mediator of PTEN deletion.

Figure 4B:
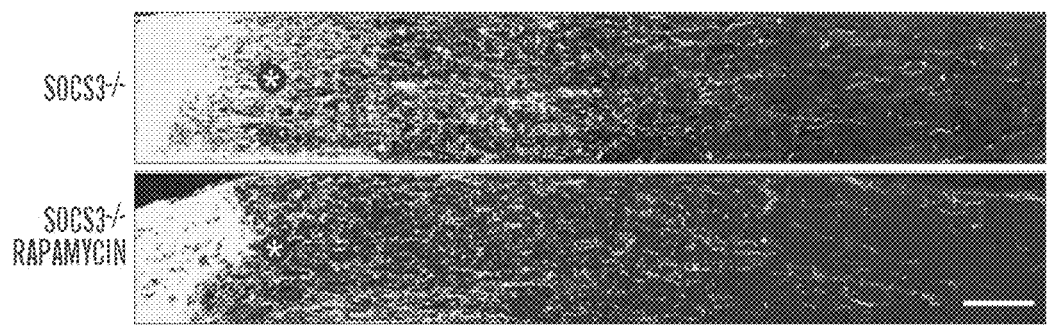
Figure 4D:
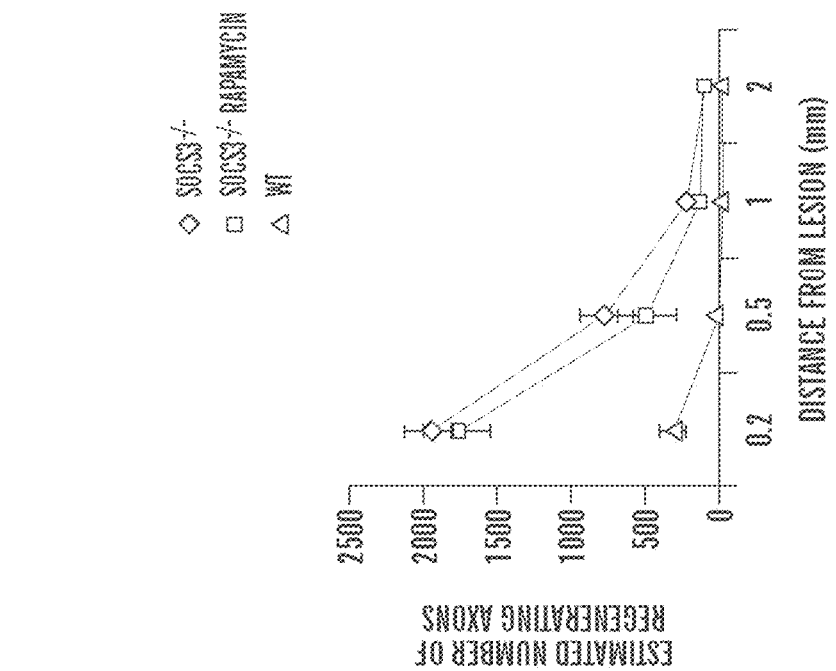
Figure 4C:
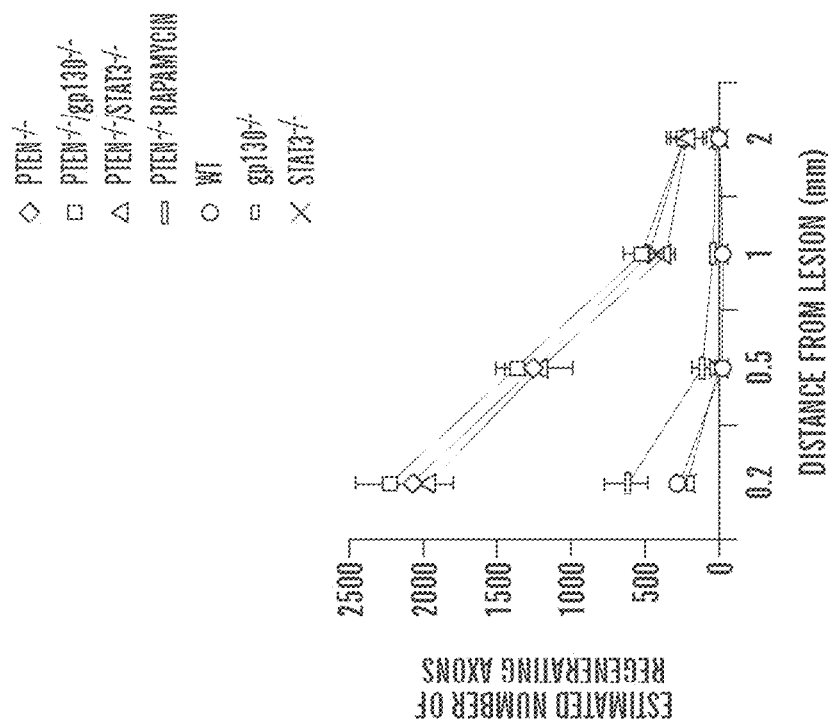

The potential role of mTOR activation in axon regeneration induced by SOCS3 deletion was also evaluated. While systematic administration of rapamycin, a specific mTOR inhibitor, abolished the majority of the axon regeneration after PTEN deletion (FIG. 4a, c), the same treatment did not affect axon regeneration from SOCS3-deleted RGCs (FIG. 4b, d). These results suggest that these two pathways act independently in regulating axon regeneration.

To assess possible gene expression alteration triggered by PTEN/SOCS3 double-deletion, gene-expression profiling studies were performed. Transgenic YFP17 mice expressing YFP in most RGCs (with only few amacrine cells, FIG. 12a), either in a control background or crossed to three different mutants, were subjected to AAV-Cre injection and optic nerve injury. 3-days post injury, mRNAs were extracted from FACS-sorted RGCs and analyzed by microarray (FIG. 12b-e).

The first potential mechanism is that certain key regeneration-promoting genes are significantly altered by PTEN/SOCS3 double deletion, when compared to both single deletions and the wild type controls. Among 15 genes selected, two encode critical positive mTOR regulators, namely small GTPase Rheb and Insulin-like growth factor 1 (IGF1)[20] (FIG. 13, 16), suggesting that positive feedback regulation of the mTOR activity in the double mutant may contribute to the enhanced and sustained axon regeneration.

The list also includes several axon growth-related genes, such as the RNA-binding protein Elavl4 (HuD), the cell adhesion molecules MAM domain-containing glycosylphosphatidylinositol anchor 2 (Mdga2)[21], procadherin beta 9 (Pcdhb9)[22], the axon guidance molecule Unc5D[23], and a cAMP-regulator phosphodiesterase 7B (Pde7b)[24] (FIG. 13, 16).

In addition, double deletion may "enhance" the regeneration-related gene-expression changes that occur poorly or moderately in the single mutants. By the criteria of significant changes (q>0.05, fold change <1.6) for comparisons between the double mutants and wild type controls, but not between the single mutants and wild type controls, the gene set shown in FIG. 14a was revealed. This includes most of genes shown in FIG. 13. Further, it shows the up-regulation of a number of axon growth-related genes, such as the signaling molecule mitogen-activated protein kinase kinase (Map2k4)[25] and the axon transport components dynein component Dync1li2, kinesin family member Kif21a, and kinesin-associated protein 3 (Kifap3)[26,27] (FIG. 14a, 16). Consistently, pathway analysis indicates that this list is enriched in genes serving cellular functions related to axon growth (FIG. 14b).

Other non-exclusive possibilities may also contribute to the synergy of the double deletion. For example, SOCS3 deletion might regulate certain axon growth-promoting genes that are poorly regulated by PTEN single deletion, thus, double deletion allows the actions of both mTOR activity and these genes. Therefore screening was performed for two sets of genes preferentially regulated by SOCS3 or PTEN deletion in the double deletion induced gene alteration (FIG. 15). These lists contain a number of genes related to axon regeneration, but whether any of the above genes show complementary/synergistic functions is still unknown. In addition, Kruppel-like factors KLF4 and KLF6 showed expression changes in opposite directions (although the changes of KLF4 did not reach statistical significance, FIG. 16), consistent with proposed opposite functions of these regeneration regulators[8].

Complementarily, the expression of a subset of genes in both intact and injured RGCs was assessed by in situ hybridization. When compared to the expression in intact RGCs, some genes, such as Elavl4 and KLF6, were induced in the mutant(s) after injury (FIG. 17a, b), consistent with the model of the activation of axon growth-related genes in these mutants. However, some other genes, such as axon transport genes Dync1li2, Kif21a, and Kifap3, and a transcription factor ZFP40, were maintained in the double-mutant RGCs but down-regulated in both wild type and single mutant RGCs after injury (FIG. 17c-f). These results suggested that in addition to inducing growth-related gene expression, the double deletion enables injured neurons to maintain their pre-injury physiological states, which might be an important contributing mechanism for the enhanced and sustained axon regeneration.

Together, these experiments reveal an important strategy for achieving sustainable de novo axon regrowth in the adult CNS neurons: co-activation of specific protein translations and gene transcriptions by concomitant inactivation of PTEN and SOCS3. Notably, the mTOR activity is maintained and phospho-STAT3 levels are increased in adult peripheral sensory neurons after injury[17,28]. Thus, the activation states of these two pathways may underlie the differential regenerative abilities of CNS and PNS neurons. However, deletion of PTEN and SOCS3 is not converting the CNS neurons to a PNS-like state, because PTEN is similarly expressed in adult PNS neurons and SOCS3 is increased during PNS regeneration[17,29]. Nonetheless, enhancing mTOR activity through deletion of PTEN or TSC2 also drastically increases axon re-growth in PNS neurons[29,30], indicating deletion of PTEN and SOCS3 may make an end-run around different growth-suppressive mechanisms. Considering the formidable long distances that regenerating axons must travel in the adult after injury, the synergistic effects of two different pathways suggest a potential solution to this challenge, making the goal of functional recovery more realistic.

Materials and Methods

Summary of Methods

AAV-Cre Injection and Optic Nerve Injury.

Adult mice were intravitreally injected with AAV-Cre and/or CNTF to the left eyes. Optic nerve injury and quantifications were done with the methods described previously[1,2].

Purification of RGCs.

72 hours after injury, isolated retinas were incubated in digestion solution, dissociated by gentle trituration, and then filtered before FACS sorting.

RNA Extraction and Microarray.

Isolated RNA was subjected to microarray analysis. Data were log 2 transformed at probe level, and the PM model-based expression values were annotated and normalized using dChip. Statistical significance of gene expression differences between groups was determined by SAM (Significance Analysis of Microarrays). After an initial filter of very low expressed genes (average log 2 transformed value <5), a False Discovery Rate (FDR rate), or q value, less than 0.05 were used to generate the significant gene lists. Functional analyses were performed using DAVID (The Database for Annotation, Visualization and Integrated Discovery).

Detailed Methods

AAV-Cre Injection.

All experimental procedures were performed in compliance with animal protocols approved by the IACUC at Children's Hospital, Boston. C57BL6/J mice (WT) or various foxed mice including Rosa-lox-STOP-lox-Tomato (from F. Wang), SOCS3$^{f/f}$, PTEN$^{f/f}$, SOCS3$^{f/f}$/PTEN$^{f/f}$, STAT3$^{f/f}$, gp130$^{f/f}$, SOCS3$^{f/f}$/STAT3$^{f/f}$, PTEN$^{f/f}$/STAT3$^{f/f}$, PTEN$^{f/f}$/gp130$^{f/f}$, YFP-17 crossed with or without SOCS3$^{f/f}$ and/or PTEN$^{f/f}$ were intravitreally injected with 1-2 μl volume of AAV-Cre (titers at 0.5-1.0×10$^{12}$) to the left eyes. For each intravitreal injection, a glass micropipette was inserted into the peripheral retina, just behind the ora serrata, and was deliberately angled to avoid damage to the lens. In some experiments, 1 μl (1 μg/μl) CNTF (Pepro Tech) was intravitreally injected immediately after injury and at 3 days post injury, and weekly thereafter.

Optic Nerve Injury.

Two weeks following AAV-Cre injection, the left optic nerve was exposed intraorbitally and crushed with jeweler's forceps (Dumont #5; Roboz) for 5 seconds approximately 1 mm behind the optic disc. Counting TUJ1+ RGCs in retina whole mount and regenerating axons were done with the methods described previously[1,2].

Purification of RGCs.

YFP17 mice, either themselves or crossed with PTEN and/or SOCS3 floxed mice, were subjected to AAV-Cre injection and optic nerve injury. 72 hours post injury, animals were euthanized and retinas were immediately dissected out for dissociation. Retinas were incubated in digestion solution (20 U/ml papain, Worthington; 1 mM L-cysteine HCL; 0.004% DNase; 0.5 mM EDTA in Neurobasal) for 30 min at 37° C., and then moved into Ovomucoid/BSA (1 mg/ml) solution to stop digestion. Subsequently, retinas were dissociated by gentle trituration with trituration buffer (0.5% B27; 0.004% DNase; 0.5 mM EDTA in Opti-MEM), and then filtered through 40 um cell strainer (BD Falcon) before FACS sorting.

FACS sorting was performed with BD FACSAria IIu. Each time immediately before sorting, a purity test was performed to insure the specificity for sorting YFP signal is higher than 99%. Dissociated retinal cells were separated based on both size (forward scatter) and surface characteristics (side scatter). Aggregated cells were excluded based on FSC-H vs FSC-A ratio. Retinal cells without YFP expression was used as negative controls to set up the detection gate each time before sorting the YFP positive cells. Sorted cells were immediately performed with RNA extraction.

RNA Extraction and Microarray.

RNA was extracted using the Qiagen RNeasy mini kit (Qiagen), and RNA quality was assessed using a bioanalyzer (Agilent Technologies). For microarray assays, RNA was amplified and labeled with the Nugen Ovation WTA System (Nugen), to obtain 2.8 μg of cRNA to be hybridized on Affymetrix mouse Genechip 1.0 ST (Affymetrix). To ensure reproducibility and biological significance, three hybridizations were performed for each group, with RNA samples collected from three independent FACS purifications, each including three or four animals (biological replicates). The microarray data accession number is GSE32309

Data from microarrays were log 2 transformed at probe level, and the PM model-based expression values were annotated and normalized using dChip (www.dchip.org <http://www.dchip.org/>). Statistical significance of gene expression differences between groups was determined by SAM (Significance Analysis of Microarrays) software (http://www-stat.stanford.edu/~tibs/SAM/). After an initial filter of very low expressed genes (average log 2 transformed value <5), a False Discovery Rate (FDR rate), or q value, less than 0.05 were used to generate the significant gene lists.

Functional annotation clustering analysis was performed using DAVID (The Database for Annotation, Visualization and Integrated Discovery, http://david.abcc.nciferf.gov/). The functional annotation groups with similar EASE score, the Fish Exact Probability Value, were clustered and grouped under the same overall enrichment score. The higher of the score, the more enriched. The five top-scored clusters were listed, and the count of genes and their percentage to corresponding categories in the database were shown.

Example 2

Central nervous system lesions, such as spinal cord injury and stroke, can damage projecting neurons, resulting in the de-nervation of functional important target areas. In principle, if the neuronal cell body is spared, functional recovery can be achieved by regeneration of lesioned axons; alternatively, especially when neuronal cell bodies are lost, sprouting from non-injured neurons/axons can form new circuits compensating for the lost functions. Although spontaneous sprouting can occur extensively in early postnatal life, it is restricted in the adult, thus functional deficits are often permanent.

The corticospinal pathway, controlling voluntary movements, is particularly important for functional recovery after spinal cord injury and stroke. It is also a valuable model for studying injury-induced axon sprouting in rodents, because it has a precise topographic organization of fibers projecting into the spinal cord, which is lost without compensation after a simple pyramidotomy in wild type animals. This mouse corticospinal injury model was therefore utilized to examine whether SOCS3 or SOCS3 PTEN double deletion could promote compensatory sprouting from the uninjured contralateral side.

Results

Figure 5:
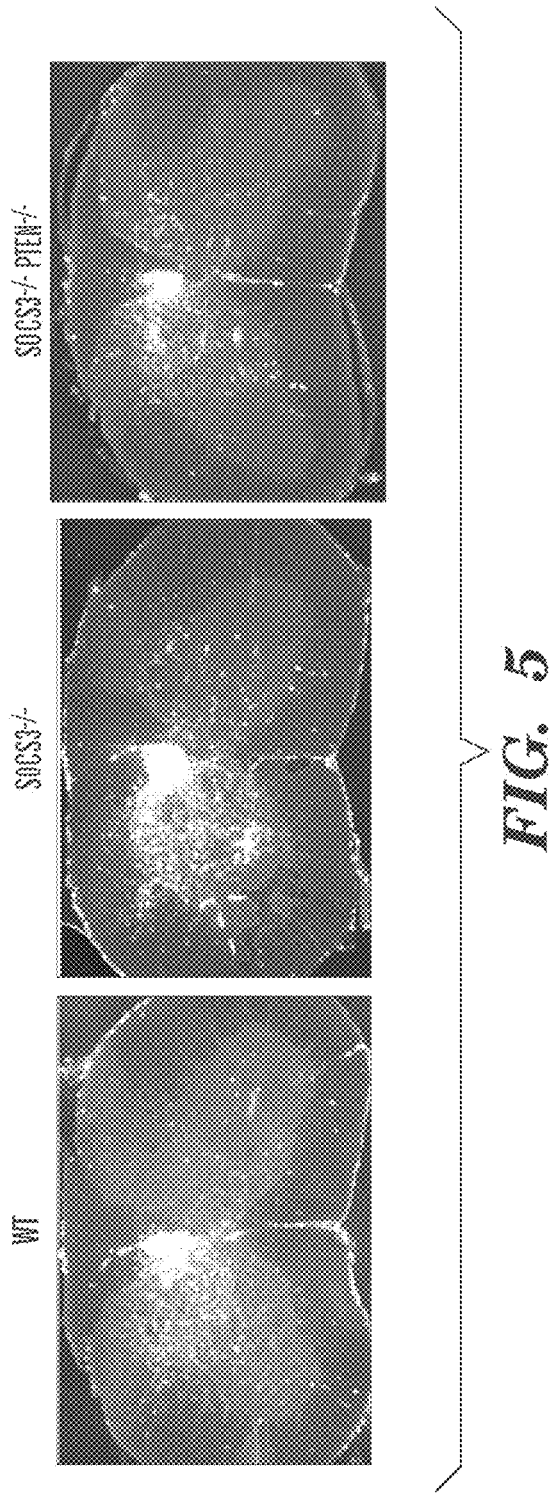
FIG. 5 shows experimental results of CST sprouting indicates co-inhibition of PTEN and SOCS3 produced synergy in promoting compensatory sprouting from intact and spared axons after partial injury. Left panel (wild type) shows BDA labeled CST fibers were rare in the denervated side of spinal cord. Central panel (SOCS3$^{-/-}$) shows SOCS3 deletion promoted robust CST sprouting into the denervated side of spinal cord. Right panel SOCS3$^{-/-}$ and PTEN$^{-/-}$): shows SOCS3 and PTEN double deletion synergistically promoted CST sprouting. C6-8 spinal cord level.

The results of the experiment are presented in FIG. 5. In results obtained from wild type mice (Left panel) BDA labeled CST fibers were rarely seen in the denervated side of spinal cord. In results obtained from SOCS3$^{-/-}$ mice (central panel), the SOCS3 deletion promoted robust CST sprouting into the denervated side of the spinal cord. In results obtained from SOCS3$^{-/-}$ and PTEN$^{-/-}$ mice (right panel), the SOCS3 and PTEN double deletion synergistically promoted CST sprouting. Sprouting was observed at the C6-8 spinal cord level.

These results indicate co-inhibition of PTEN and SOCS3 synergize at promoting compensatory sprouting from intact and spared axons after partial injury, which is different from promoting axon regeneration from injured neurons. These data provide a basis for designing therapies for incomplete injuries such as stroke, traumatic brain injury, multiple sclerosis and spinal cord injury.

Materials and Methods

AAV Injection.

Neonatal SOCS3$^{loxP/loxP}$ or SOCS3$^{loxP/loxP}$/PTEN$^{loxP/loxP}$ mice were cryoanesthetized and injected with 2 μl of AAV-Cre for gene deletion or AAV-GFP as control. Injections were made into the right sensorimotor cortex using a nanoliter injector attached to a fine glass pipette. Mice were then placed on a warming pad and returned to their mothers after regaining normal color and activity. A pyramidotomy was performed 6-8 weeks later.

Pyramidotomy.

Mice were anesthetized with ketamine/xylazine. An incision was made at the left side of the trachea. Blunt dissection was performed to expose the skull base and a craniotomy in the occipital bone allowed for access to the medullary pyramids. The left or right pyramid was cut with a fine scalpel medially up to the basilar artery. The wound was closed in layers with 6.0 sutures. The mice were placed on soft bedding on a warming blanket held at 37° C. until fully awake.

BDA Tracing.

8-12 weeks after injury, CST axons on the non-injured side was anterogradely traced with biotinylated dextran amines (BDA). A total of 4.0 μl of BDA (10%, Invitrogen) was injected into sensorimotor cortex at four sites (anterior-posterior coordinates from bregma in mm: 1.0/1.5, 0.5/1.5, −0.5/1.5, −1.0/1.5, all at a depth of 0.5 mm into cortex). Mice were kept for an additional 2 weeks before being killed.

References for Examples 1 and 2

1. Park, K. K., et al. Promoting axon regeneration in the adult CNS by modulation of the PTEN/mTOR pathway. *Science* 322, 963-966 (2008).
2. Smith, P. D., et al. SOCS3 deletion promotes optic nerve regeneration in vivo. *Neuron* 64, 617-623 (2009).
3. Fawcett, J. Molecular control of brain plasticity and repair. *Prog Brain Res* 175, 501-509 (2009).
4. Filbin, M. T. Recapitulate development to promote axonal regeneration: good or bad approach? *Philos Trans R Soc Lond B Biol Sci* 361, 1565-1574 (2006).

5. Fitch, M. T. & Silver, J. CNS injury, glial scars, and inflammation: Inhibitory extracellular matrices and regeneration failure. *Exp Neurol* 209, 294-301 (2008).
6. Hellal, F., et al. Microtubule stabilization reduces scarring and causes axon regeneration after spinal cord injury. *Science* 331, 928-931 (2011).
7 Leibinger, M., et al. Neuroprotective and axon growth-promoting effects following inflammatory stimulation on mature retinal ganglion cells in mice depend on ciliary neurotrophic factor and leukemia inhibitory factor. *J Neurosci* 29, 14334-14341 (2009).
8. Moore, D. L., et al. KLF family members regulate intrinsic axon regeneration ability. *Science* 326, 298-301 (2009).
9. Winzeler, A. M., et al. The lipid sulfatide is a novel myelin-associated inhibitor of CNS axon outgrowth. *J Neurosci* 31, 6481-6492 (2011).
10. Groszer, M., et al. Negative regulation of neural stem/progenitor cell proliferation by the Pten tumor suppressor gene in vivo. *Science* 294, 2186-2189 (2001).
11. Mori, H., et al. Socs3 deficiency in the brain elevates leptin sensitivity and confers resistance to diet-induced obesity. *Nat Med* 10, 739-743 (2004).
12. Fasnacht, N. & Muller, W. Conditional gp130 deficient mouse mutants. *Semin Cell Dev Biol* 19, 379-384 (2008).
13. Ernst, M. & Jenkins, B. J. Acquiring signalling specificity from the cytokine receptor gp130. *Trends Genet* 20, 23-32 (2004).
14. Park, K. K., et al. Cytokine-induced SOCS expression is inhibited by cAMP analogue: impact on regeneration in injured retina. *Mol Cell Neurosci* 41, 313-324 (2009).
15. Park, K., Luo, J. M., Hisheh, S., Harvey, A. R. & Cui, Q. Cellular mechanisms associated with spontaneous and ciliary neurotrophic factor-cAMP-induced survival and axonal regeneration of adult retinal ganglion cells. *J Neurosci* 24, 10806-10815 (2004).
16. Bareyre, F. M., et al. In vivo imaging reveals a phase-specific role of STAT3 during central and peripheral nervous system axon regeneration. *Proc Natl Acad Sci USA* 108, 6282-6287 (2011).
17. Miao, T., et al. Suppressor of cytokine signaling-3 suppresses the ability of activated signal transducer and activator of transcription-3 to stimulate neurite growth in rat primary sensory neurons. *J Neurosci* 26, 9512-9519 (2006).
18. Qiu, J., Cafferty, W. B., McMahon, S. B. & Thompson, S. W. Conditioning injury-induced spinal axon regeneration requires signal transducer and activator of transcription 3 activation. *J Neurosci* 25, 1645-1653 (2005).
19. Aaronson, D. S. & Horvath, C. M. A road map for those who don't know JAK-STAT. *Science* 296, 1653-1655 (2002).
20. Sengupta, S., Peterson, T. R. & Sabatini, D. M. Regulation of the mTOR complex 1 pathway by nutrients, growth factors, and stress. *Mol Cell* 40, 310-322 (2010).
21. Joset, P., et al. Rostral growth of commissural axons requires the cell adhesion molecule MDGA2. *Neural Dev* 6, 22 (2011).
22. Junghans, D., Haas, I. G. & Kemler, R. Mammalian cadherins and protocadherins: about cell death, synapses and processing. *Curr Opin Cell Biol* 17, 446-452 (2005).
23. Low, K., Culbertson, M., Bradke, F., Tessier-Lavigne, M. & Tuszynski, M. H. Netrin-1 is a novel myelin-associated inhibitor to axon growth. *J Neurosci* 28, 1099-1108 (2008).
24. Hannila, S. S. & Filbin, M. T. The role of cyclic AMP signaling in promoting axonal regeneration after spinal cord injury. *Exp Neurol* 209, 321-332 (2008).
25. Nix, P., Hisamoto, N., Matsumoto, K. & Bastiani, M. Axon regeneration requires coordinate activation of p38 and JNK MAPK pathways. *Proc Natl Acad Sci USA* 108, 10738-10743 (2011).
26. Hanz, S. & Fainzilber, M. Retrograde signaling in injured nerve—the axon reaction revisited. *J Neurochem* 99, 13-19 (2006).
27. Hoffman, P. N. A conditioning lesion induces changes in gene expression and axonal transport that enhance regeneration by increasing the intrinsic growth state of axons. *Exp Neurol* 223, 11-18 (2010).
28. Park, K. K., Liu, K., Hu, Y., Kanter, J. L. & He, Z. PTEN/mTOR and axon regeneration. *Exp Neurol* 223, 45-50 (2010).
29. Abe, N., Borson, S. H., Gambello, M. J., Wang, F. & Cavalli, V. Mammalian target of rapamycin (mTOR) activation increases axonal growth capacity of injured peripheral nerves. *J Biol Chem* 285, 28034-28043 (2010).
30. Christie, K. J., Webber, C. A., Martinez, J. A., Singh, B. & Zochodne, D. W. PTEN inhibition to facilitate intrinsic regenerative outgrowth of adult peripheral axons. *J Neurosci* 30, 9306-9315 (2010).

Example 3

Injury to the mammalian adult CNS often results in functional deficits, largely owing to the disruption of neuronal circuits. In the case of spinal cord injury, the disruption of axonal tracts that convey ascending sensory and descending motor information leads to pronounced and persistent sensorimotor dysfunction in the body below the lesion. Presumably, re-building the neuronal circuits may result from two types of axon regrowth: regenerative growth of injured axons and/or compensatory sprouting from spared axons. While spontaneous regenerative growth occurs rarely in the adult CNS, compensatory sprouting of the same or different types of axons occurs often after incomplete injury and has been proposed as a major mechanism for spontaneous functional recovery after CNS injuries (Kaas 1991; Florence et al., 1998; Maier and Schwab, 2008; Benowitz and Carmichael, 2010; Rosenzweig et al., 2010).

In both experimental animal models and human patients, partial injury of the spinal cord is often followed by functional recovery, which is usually incomplete (Maier and Schwab, 2008). For example, in monkeys, a small portion (25%) of spared white matter is sufficient to allow recovery of coordinated hindlimb locomotion but not grasping after injury (Eidelberg et al. 1981). Importantly, a close correlation has been observed between the anatomical reorganization of spared descending fibers and spontaneous functional recovery after injury. For example, in young animals with a unilateral CST lesion, CST fibers from the uninjured side sprout heavily into the contralateral, denervated side, and this sprouting is followed by a high level of recovery of forelimb function (Kuang & Kalil 1990; Rouiller et al. 1991; Aisaka et al. 1999). However, in adults, spared descending fibers send few to no collaterals across the midline to the denervated side (Aoki et al. 1986; Woolf et al. 1992; Goldstein et al. 1997; Weidner et al., 2001; Bareyre et al., 2004; Cafferty and Strittmatter, 2006), and this has been proposed as a key limiting factor for functional recovery after spinal cord injury in the adult.

In recent studies investigating the molecular mechanisms that control the intrinsic regenerative ability of mature CNS neurons, it has been shown that the mTOR activity is a critical determinant of intrinsic growth ability and undergo a down-regulation in cortical neurons over the course of postnatal development (Liu et al., 2010). As a result, deletion of PTEN, a negative regulator of the mTOR pathway (reviewed in Ma and Blenis, 2009; Liu et al., 2011), significantly increases compensatory sprouting responses of CNS neurons (Liu et al., 2010), suggesting that neuronal intrinsic growth ability is an important regulator of axonal sprouting.

PTEN deletion in cortical neurons does not induce sprouting, however, unless there is also an injury (Liu et al., 2010), suggesting that increased intrinsic growth potential, by itself, is insufficient to initiate a sprouting response. This observation raises an important question: what extrinsic factors trigger spared axons to initiate a sprouting response after partial injury? In this study, it was demonstrate that genetic deletion of SOCS3, an established inhibitor of the JAK/STAT pathway, enhances CST sprouting after unilateral pyramidotomy. The JAK/STAT pathway is usually activated by cytokines such as CNTF (Nicholson et al., 2000; Crocker et al., 2008). Consistently, it is also shown that denervated neurons in the spinal cord up-regulate CNTF expression, suggesting that denervation-induced cytokine expression might be an important trigger for axonal sprouting.

Results

SOCS3 Deletion Increases CST Sprouting after Unilateral Pyramidotomy

Figure 22A:
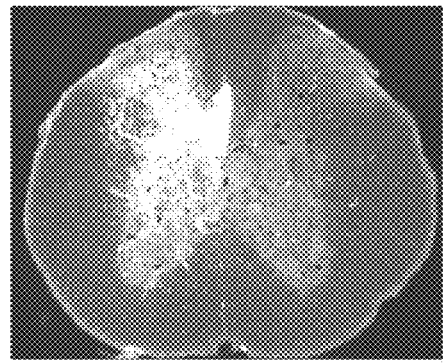
Figure 22B:
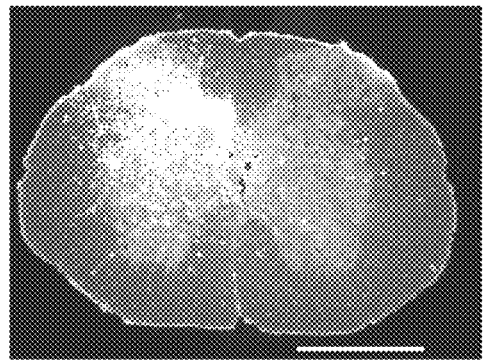
Figure 22C:
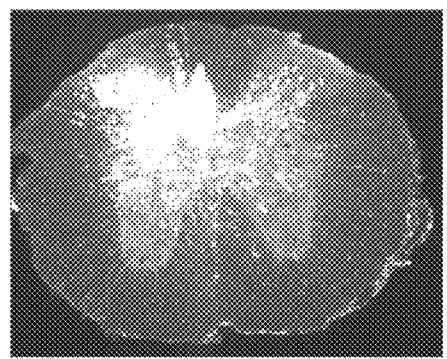
Figure 22D:
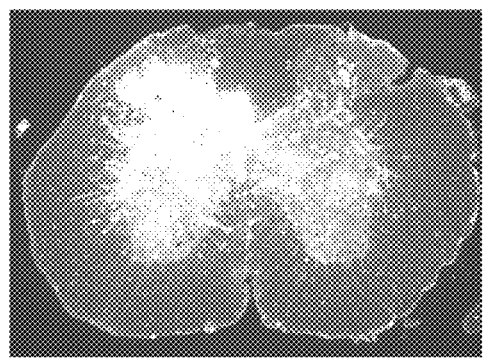
Figure 22E:
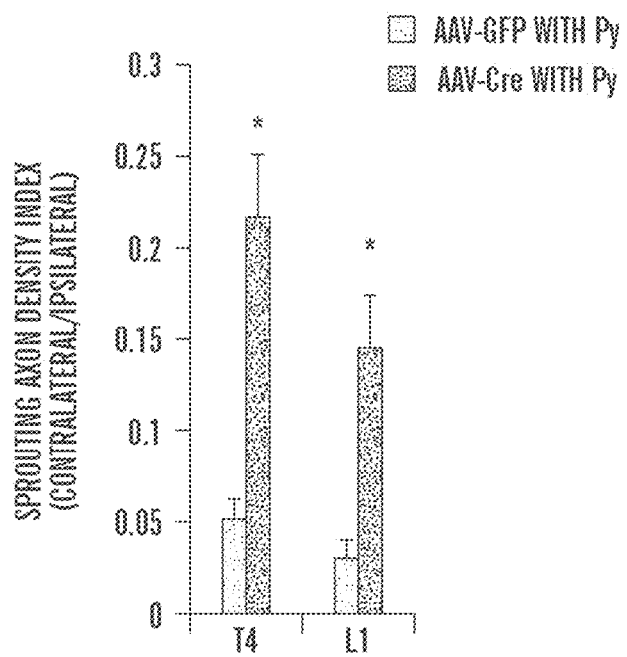
Figure 22F:
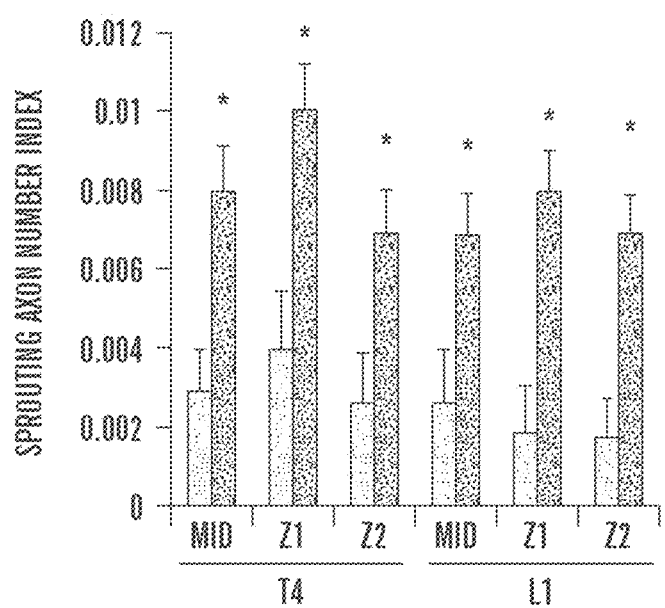
Figure 22G:
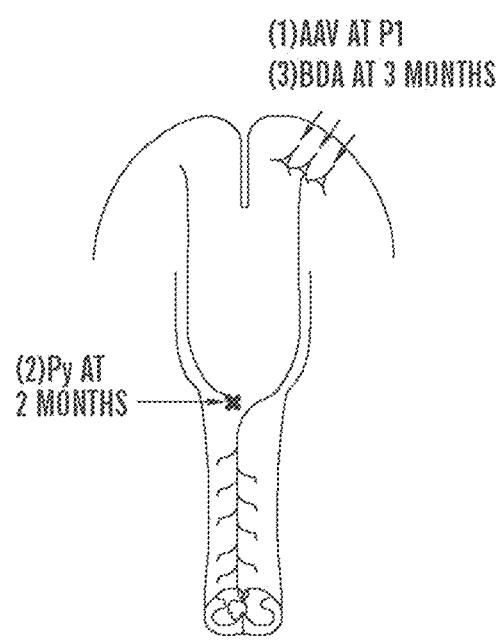
Figure 23A:
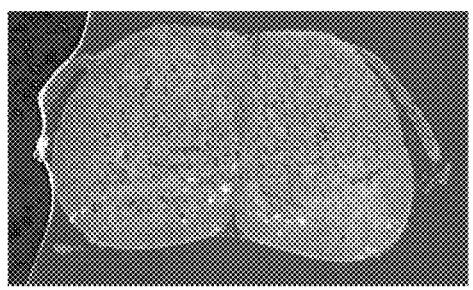
Figure 23B:
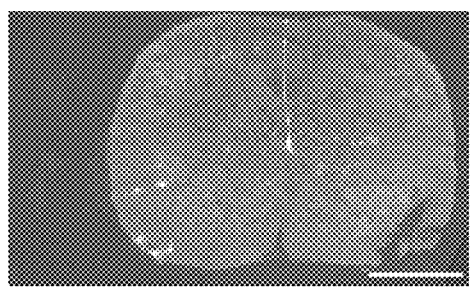
Figure 23C:
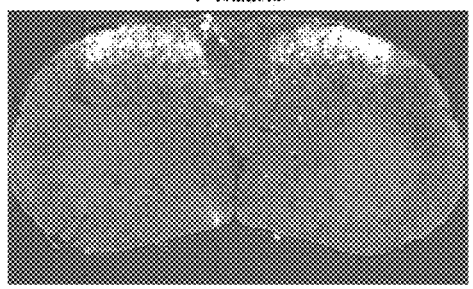
Figure 23D:
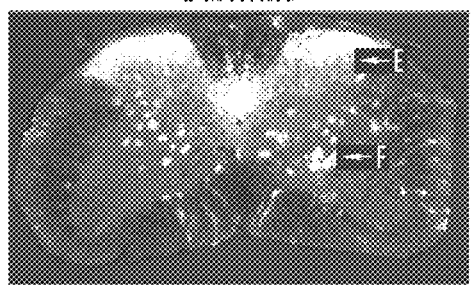
Figure 23E:
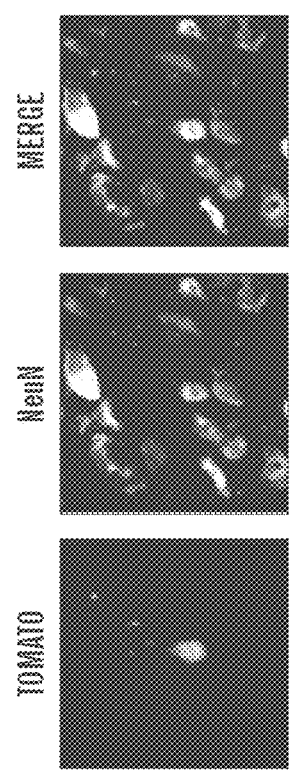
Figure 23F:
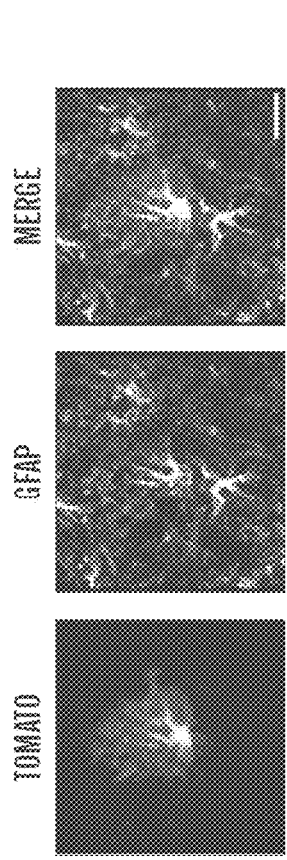

Previous studies showed that deleting SOCS3 in retinal ganglion neurons promotes the regeneration of injured optic nerve axons after injury (Smith et al., 2009, Sun et al., 2011). Thus, whether SOCS3 deletion could affect the sprouting response of CST axons after unilateral pyramidotomy was assessed (FIG. 22G). In this injury paradigm, CST axons from the left cortical hemisphere are transected at the medullary pyramid above the pyramidal decussation. To monitor collateral sprouting from uninjured CST axons, BDA is injected into the right sensoromotor cortex at 4 weeks post-injury and cross sections from different levels of the spinal cord are analyzed after waiting an additional 2 weeks (FIG. 22G). In control mice, most of the labeled axons are on the left side of the spinal cord, with minimal labeling on the right side (Weidner et al., 2001; Bareyre et al., 2004; Cafferty and Strittmatter, 2006; Liu et al., 2010). Thus, the number of labeled axons on the right side of the spinal cord originating from the left intact CST can be used to quantify the extent of CST compensatory sprouting.

Figure 18A:
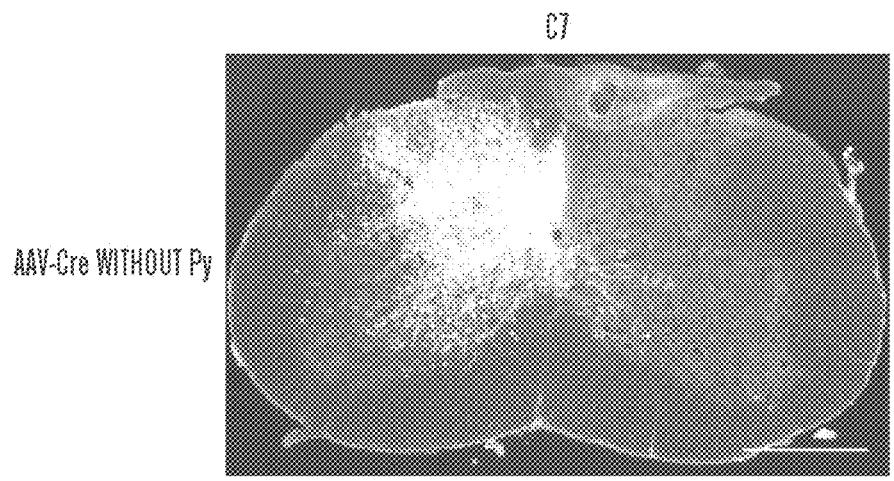
Figure 18B:
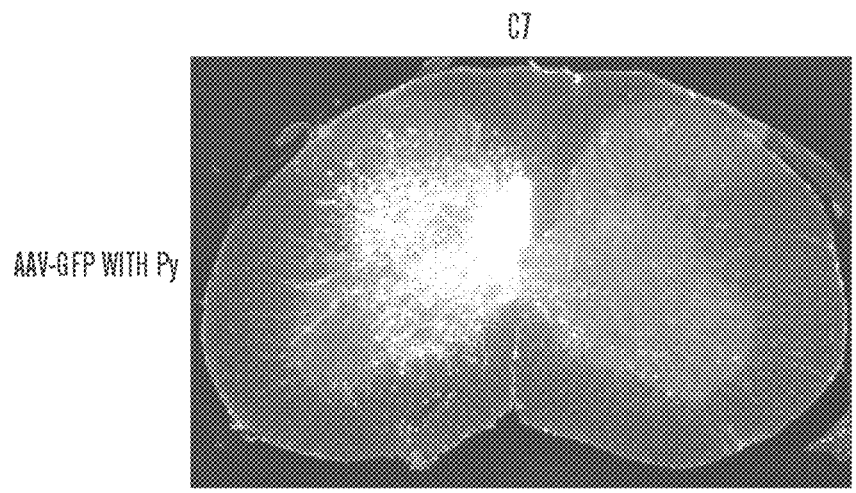
Figure 18C:
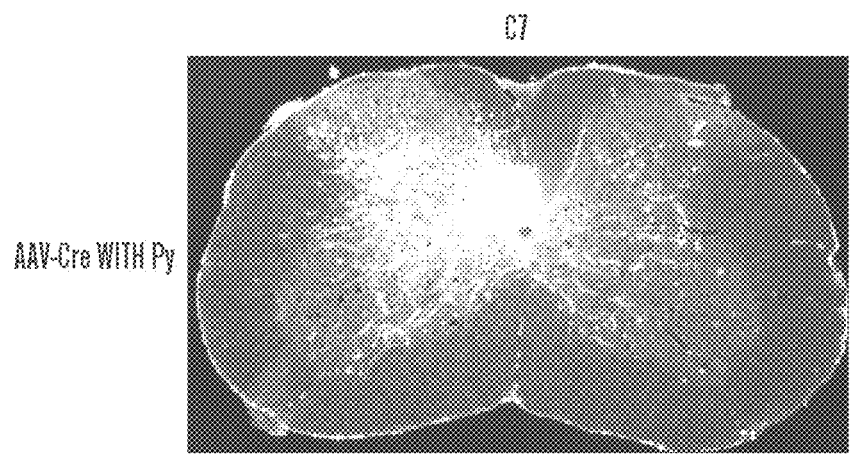
Figure 18D:
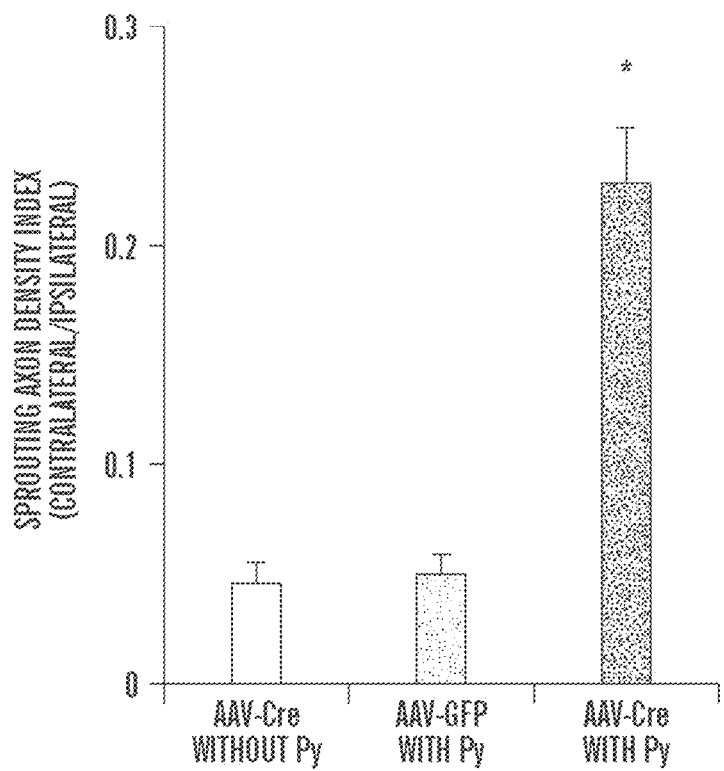
Figure 18E:
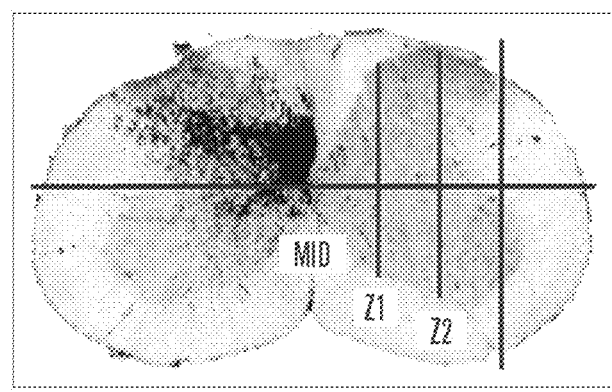
Figure 18F:
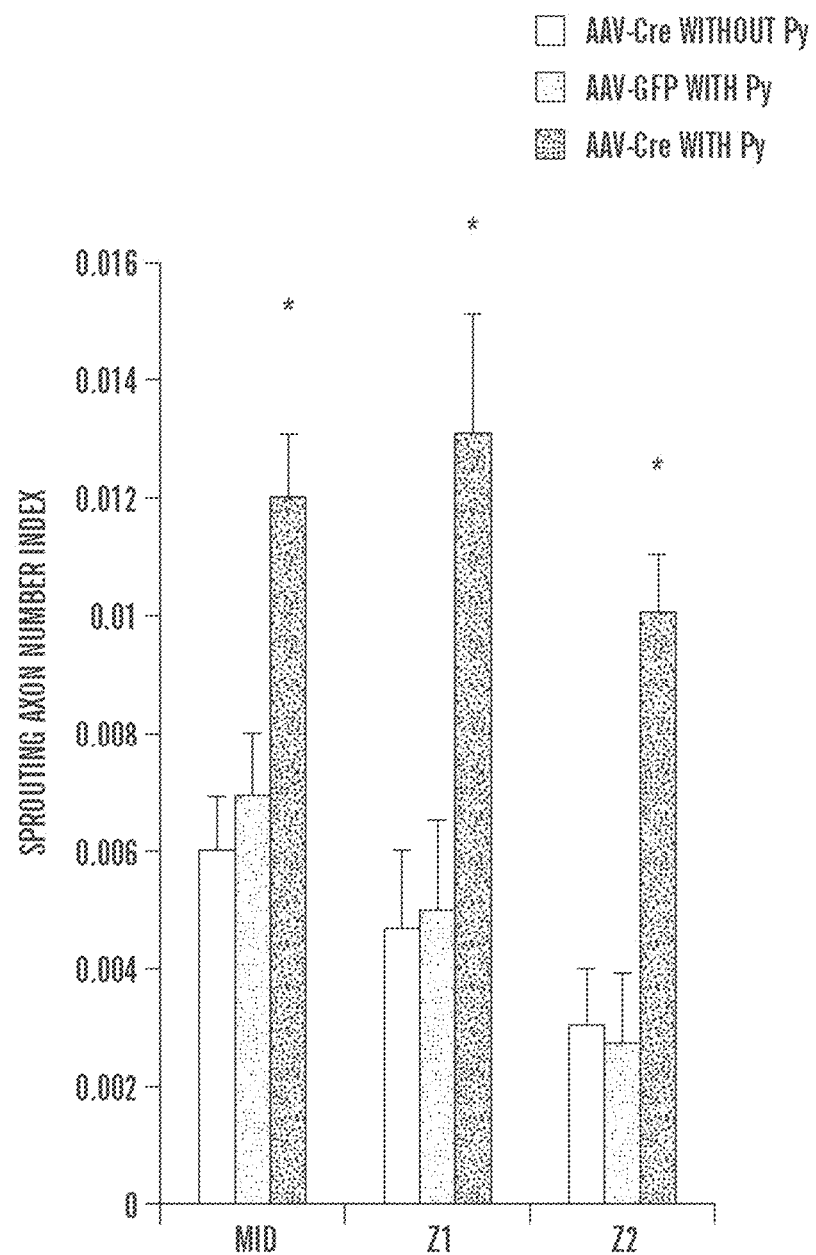
Figure 19A:
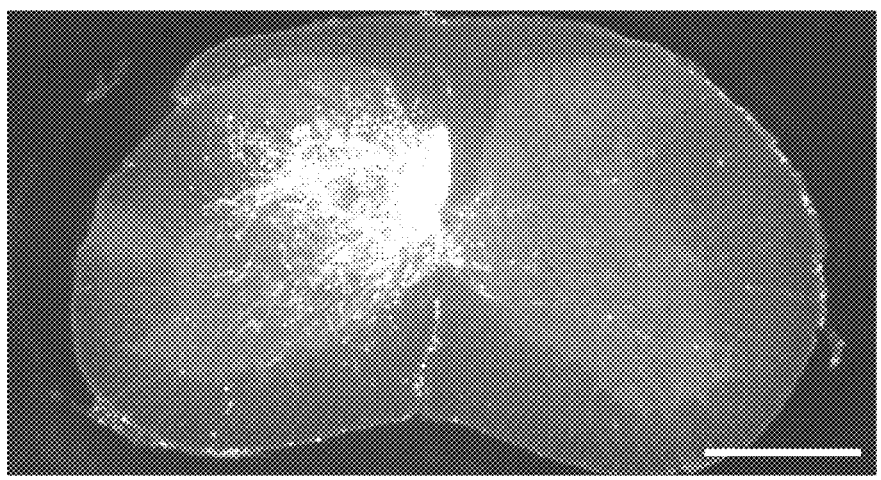
Figure 19B:
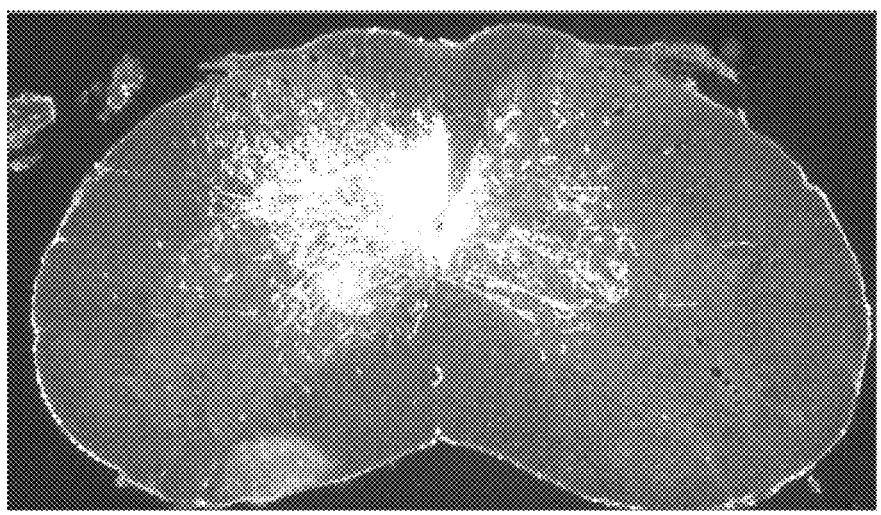
Figure 19D:
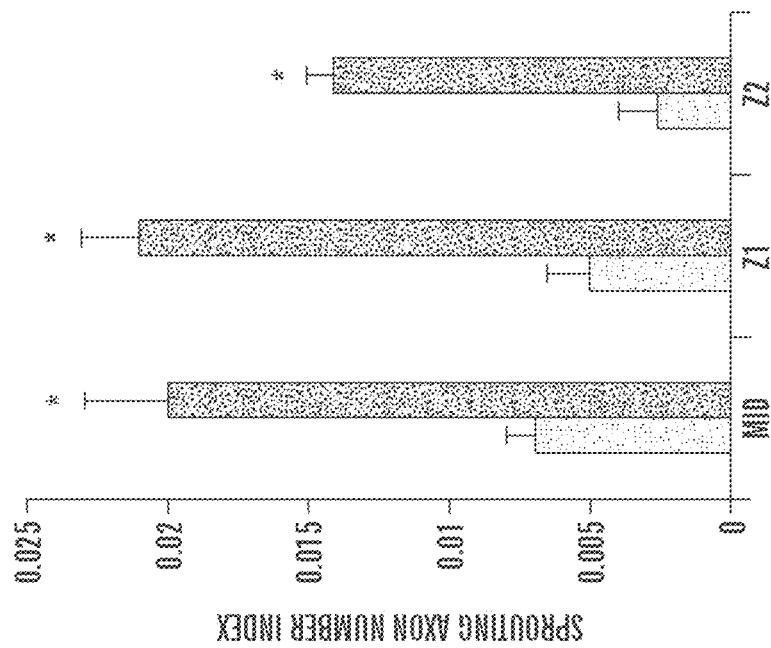
Figure 19C:
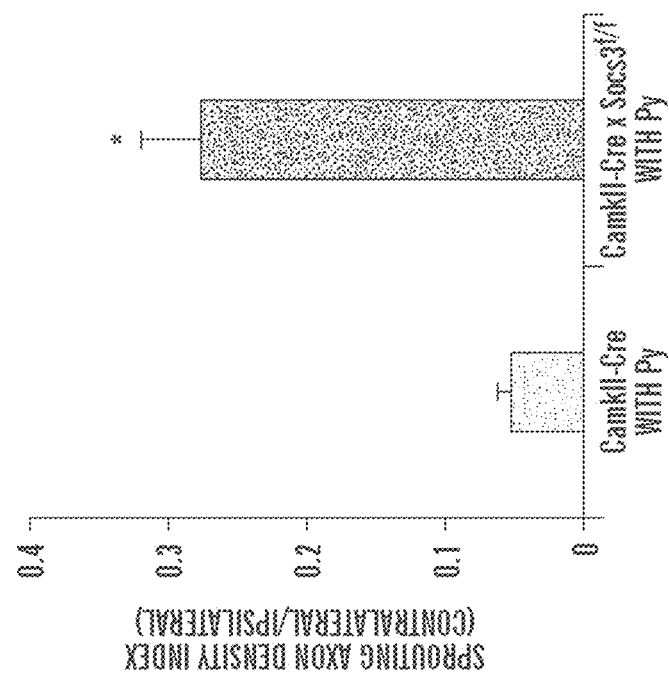
Figure 20A:
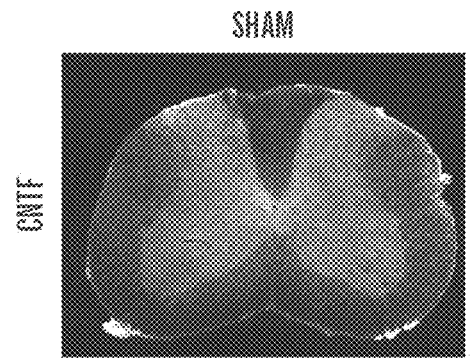
Figure 20B:
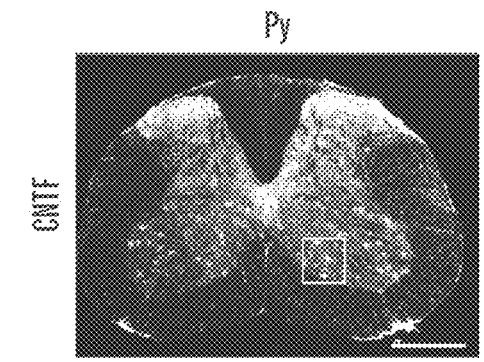
Figure 20C:
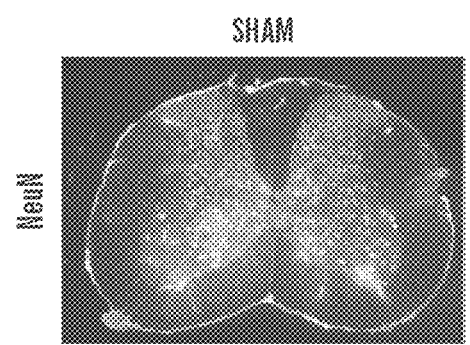
Figure 20D:
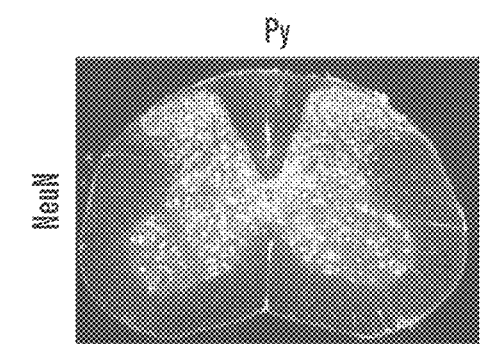
Figure 20E:
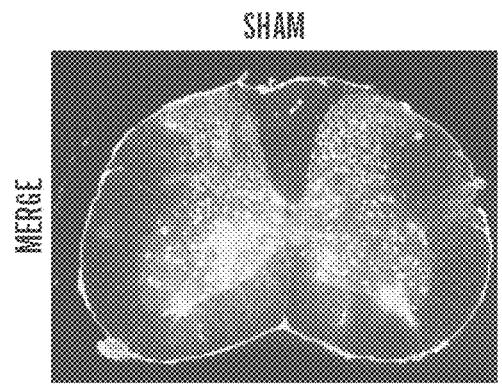
Figure 20F:
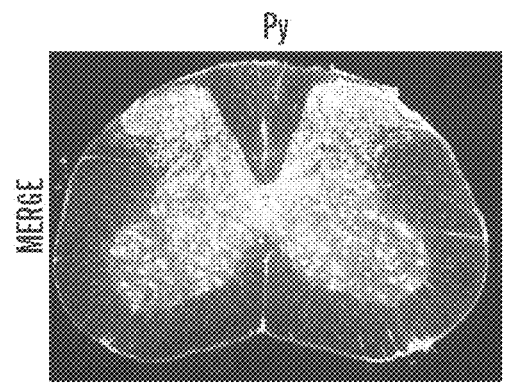
Figure 20G:
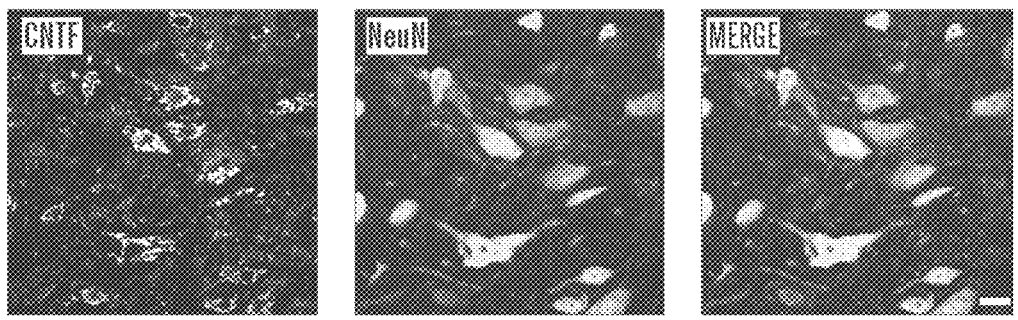

To delete SOCS3 in cortical neurons, Cre-expressing adeno-associated virus (AAV-Cre) was injected into the right side of the sensorimotor cortex of homozygous conditional SOCS3 mutants (SOCS3loxp/loxp, Mori et al., 2004) on postnatal day 1 (P1). This approach has been previously shown to induce efficient Cre-dependent recombination in neurons throughout the sensorimotor cortex (Liu et al., 2010). Deletion of SOC3 at this stage did not appear to change the pattern of CST projections in the adult (FIG. 18A). A left unilateral pyramidotomy was performed at eight weeks of age, and sprouting responses were analyzed 6 weeks post-injury. SOCS3 deletion significantly increased sprouting from the spared (intact, left) half of the CST into the denervated (right) side of the spinal cord (FIG. 18C). The number of labeled CST axons is enhanced most significantly at cervical levels of the spinal cord, but the increase is also obvious at lower levels (FIG. 22A-22F). In the denervated (right) side of the spinal cord, the labeled axons could be seen in different regions of the gray matter, with the most abundant projections in the intermediate and dorsal spinal cord (FIG. 18C). The density of compensatory/collateral sprouting fibers amounted to 25% of the uncrossing CST (FIG. 18D), similar to the extent observed after PTEN deletion (Liu et al., 2010). These results suggest that the signaling pathway(s) regulated by SOCS3 regulate the capacity for compensatory sprouting of spared CST axons.

To determine if SOC3 deletion is able to enhance post-injury sprouting when it is deleted from neurons at stages later than P1, the above experiment was repeated with a CamKII-Cre driver, which is not active in CST neurons until P21 (FIG. 23, Yu et al., 2001). As shown in FIG. 19, significant sprouting responses are also observed in SOCS3f/f mice crossed with CamKII-Cre mice, and the extent was similar to that seen when SOCS3 is deleted at P1 (compare FIGS. 18C and 19B). This suggests that SOCS3 deletion in neonatal and relatively mature cortical neurons is able to initiate sprouting responses after a unilateral pyramidotomy.

CNTF is up-regulated in the spinal cord after unilateral pyramidotomy SOCS3 is a negative regulator of the JAK/STAT pathway, which is often activated by cytokines such as CNTF (Crocker et al., 2008; Sun et al., 2011). Enhanced CST sprouting from intact cortical neurons after SOCS3 deletion suggests that axonal sprouting responses might be regulated by access to extrinsic cytokines which activate the JAK/STAT pathway. Because the pyramidotomy is performed on one side of the medullary pyramid, we examined the expression of CNTF in the cortex (where CST axons originate) and in the spinal cord (where CST axons terminate) in both intact and injured wild type mice.

Figure 24A:
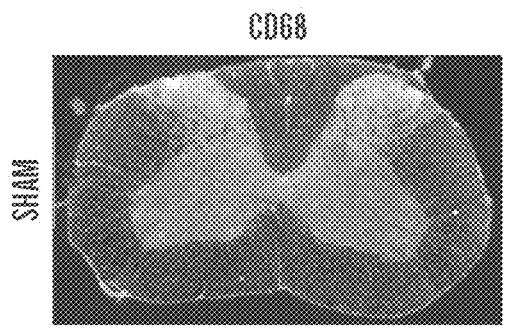
Figure 24B:
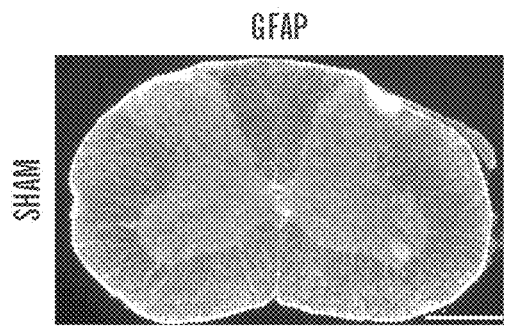
Figure 24C:
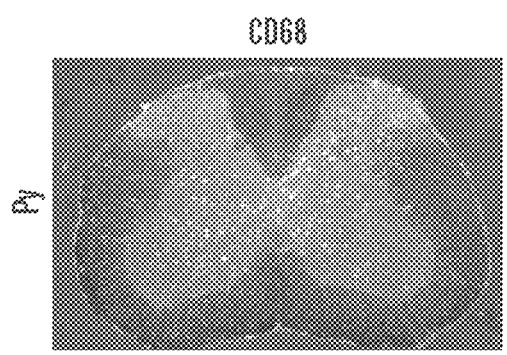
Figure 24D:
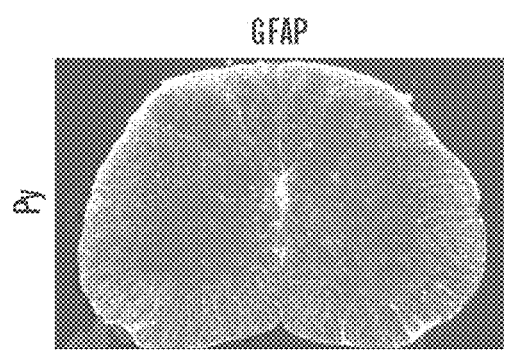
Figure 24F:
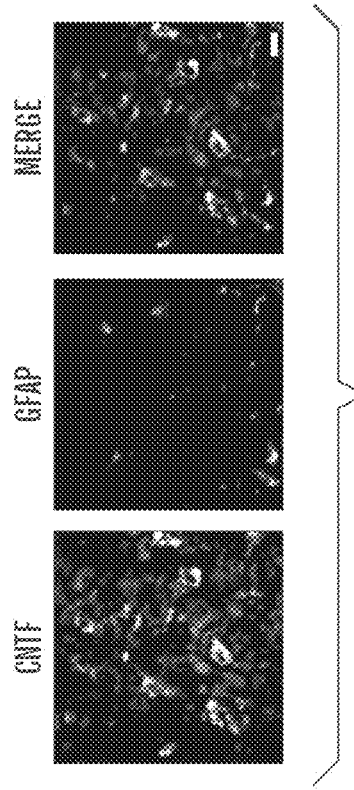
Figure 24H:
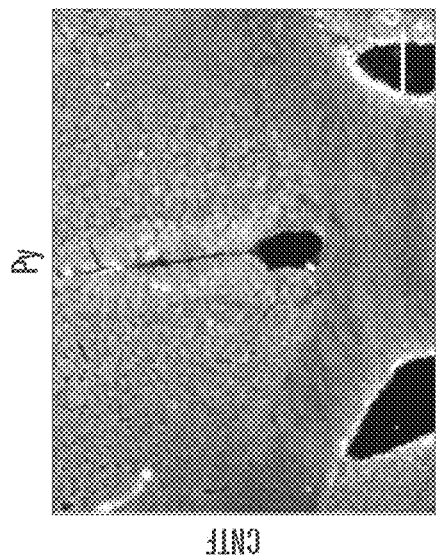
Figure 24E:
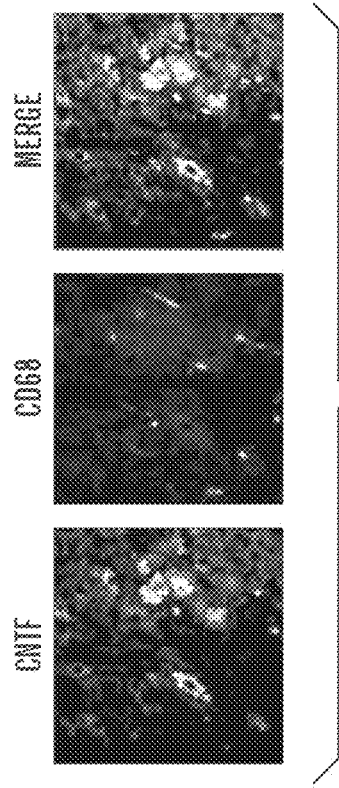
Figure 24G:
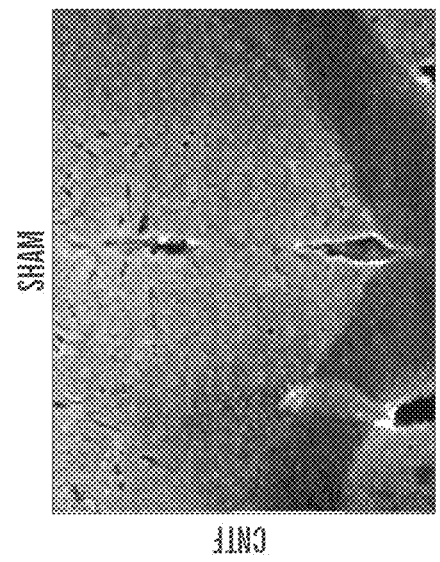
Figure 26A:
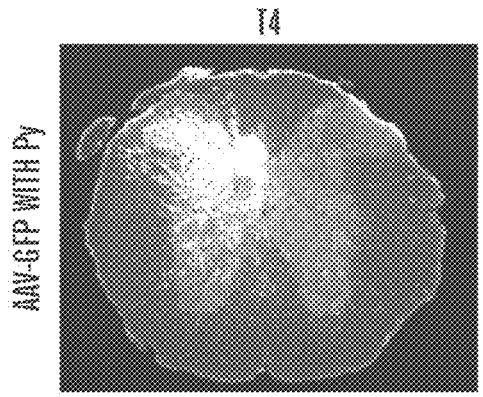
Figure 26B:
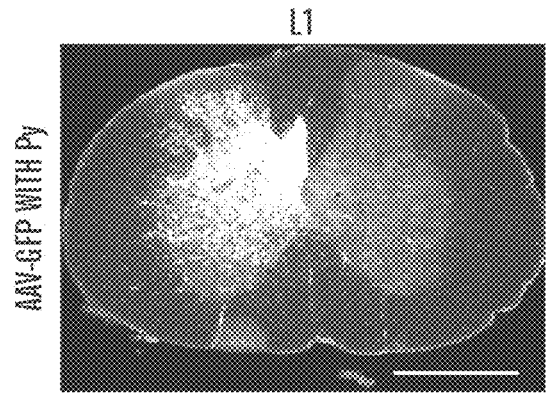
Figure 26C:
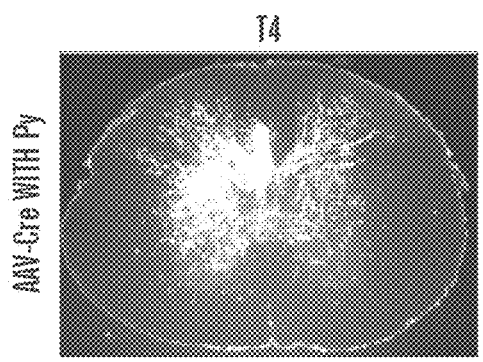
Figure 26D:
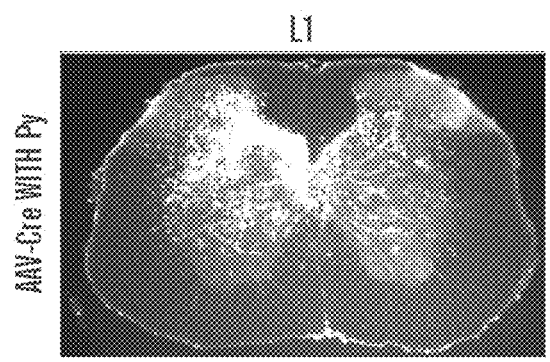
Figure 26E:
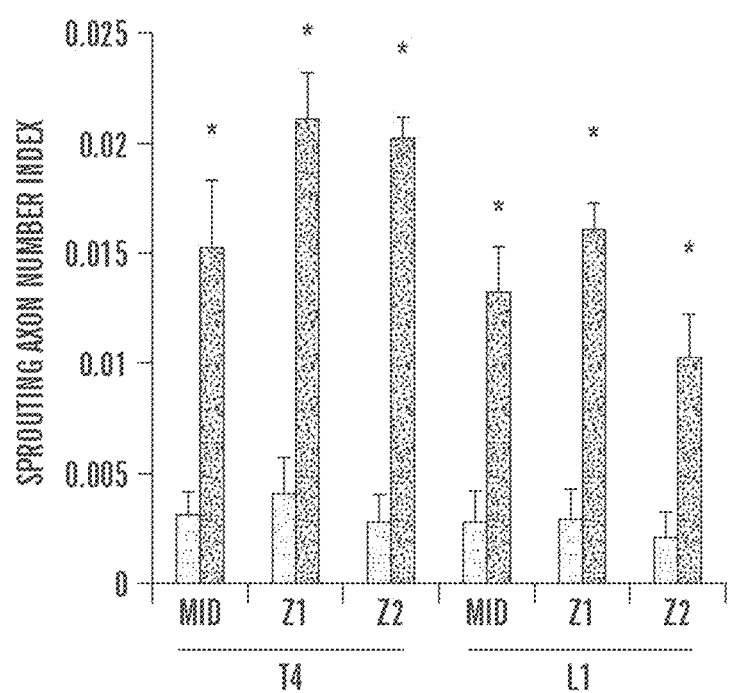

As shown in FIGS. 24G and 24H, no detectable immunoreactivity with anti-CNTF antibodies could be found on either side of the cortex after a left pyramidotomy on different days post-injury, suggesting that it is unlikely that CNTF from cortical regions contribute to the enhanced sprouting response. However, at 3 days post-injury, CNTF immunoreactivity was significantly increased in the spinal cord, especially on the denervated side, compared to the low level signals seen in the intact spinal cord (FIG. 20).

CNTF is Up-Regulated in Neurons after Pyramidotomy

Next, possible mechanisms of CNTF up-regulation after unilateral CST ablation were examined. At least two possibilities could be envisioned. First, neurons in the spinal cord deprived of CST inputs may up-regulate cytokines to stimulate collateral axonal sprouting. Second, an inflammatory response triggered by the Wallerian degeneration of the transected CST might result in an upreguation of cytokines from infiltrating immune cells as well as activated CNS cells, such as astrocytes and microglia. Indeed, although the lesion site for the pyramidotomy is at the medullary pyramid level and there are no manipulations applied to the spinal cord, we found that by 3 days after unilateral pyramidotomy, CD68+ cells (likely macrophages or microglia) accumulated in the spinal cord, with more in the right dorsal column where the transected CST undergo Wallerian degeneration (FIG. 24C). Sparse GFAP labeling was seen in the intact spinal cord, and this is not altered by a left pyramidotomy, suggesting no obvious astrocyte activation after unilateral pyramidotomy (FIG. 24D).

Next, which cell type(s) increased CNTF expression in the spinal cord after a left pyramidotomy was examined. It appeared that most immuno-reactivity with anti-CNTF antibodies co-localizes with NeuN+ neurons (FIG. 20), but not with CD68+ or GFAP+ cells (FIGS. 24E and 24F). This is different from what was seen after spinal cord injury, where CNTF expression is increased in reactive glial cells around the lesion (Tripathi and Mctigue, 2008). Thus, by using the pyramidotomy at the medullary pyramid, our results reveal that CNTF expression is induced mainly in neurons in the spinal cord after CST inputs are depleted, which might provide a possible explanation for extensive CST sprouting towards the denervated site. The identity of these neurons, however, is unknown. It is also unknown whether these neurons are direct or indirect synaptic targets of CST axons.

To assess whether the CNTF up-regulation in denervated neurons is secondary to the inflammatory response in the degenerating CST, the time course of the accumulation of CD68+ cells versus CNTF+up-regulation in neurons was analyzed. Increased CNTF signals were seen as early as 2 day after injury, which continues to increase at 3 days after injury (FIG. 20). CD68+ cells, on the other hand, did not become obvious until 3 days post-injury (FIG. 24C and data not shown), arguing against the notion that CNTF up-regulation in neurons is secondary to the inflammatory response.

Exogenously Applied CNTF Triggers CST Sprouting in the Absence of Pyramidotomy

Next, whether exogenously applied CNTF is sufficient to trigger CST sprouting in uninjured adult mice was examined. AAV-Cre was injected into SOCS3f/f mice at P1, and CNTF was injected into the spinal cord at C1 when the animals reached adulthood. CST sprouting was then analyzed 8 weeks after injection. As shown in FIG. 25A-F, CNTF, but not saline, injected into the dorsal spinal cord at the C1 level, indeed triggered a significant CST sprouting response at the C1 (FIG. 25A-D), but not C7 (FIGS. 25E and 25F), spinal cord level. In these animals, many CST sprouts crossed the midline and projected towards the contralateral side of the spinal cord. However, the extent of sprouting is less than after left pyramidotomy. This may be due to the fact that the elevation of CNTF after pyramidotomy might be more prolonged than what was achieved with our single injection. Additionally, other cytokines or growth factors might be involved in sprouting after unilateral pyramidotomy.

Further enhanced CST sprouting induced by co-deletion of SOCS3 and PTEN The results above suggest that denervation-triggered CNTF expression in neurons might be an important extrinsic regulator of CST collateral sprouting. Whether increasing intrinsic growth capacity in uninjured CST neurons by increasing mTOR activity by a deletion of PTEN could further increase the extent of CST sprouting elicited by SOCS3 deletion was examined. Either AAV-Cre or AAV-GFP was injected to the right sensorimotor cortex of PTEN$^{f/f}$/SOCS3f/f mice at P1, performed the pyramidotomy on the left side at 8 weeks of age, and analyzed the extent of CST sprouting at 6 weeks post-injury.

Figure 21A:
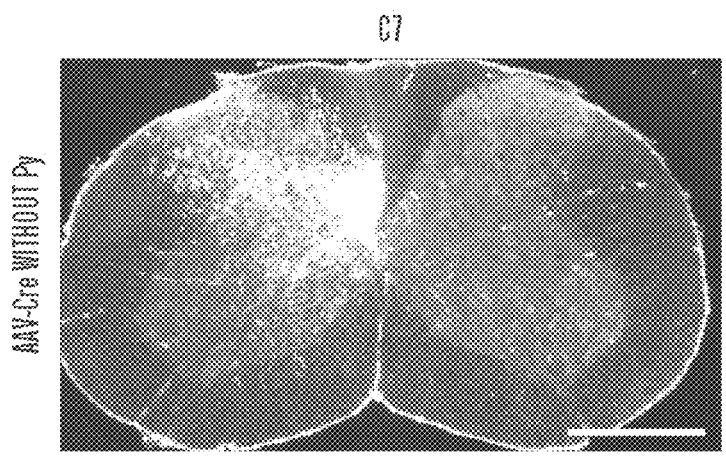
Figure 21B:
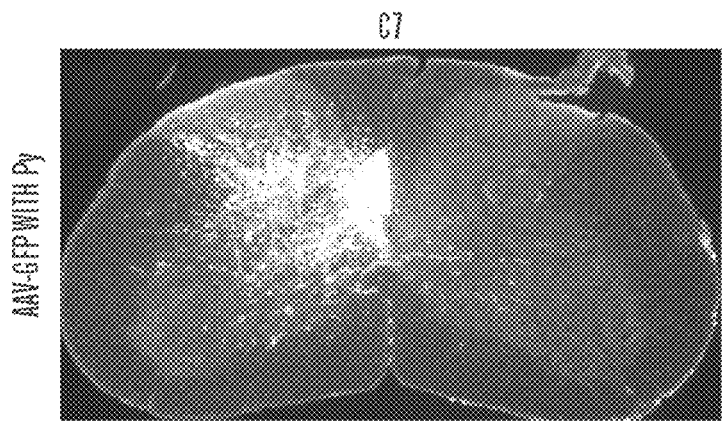
Figure 21C:
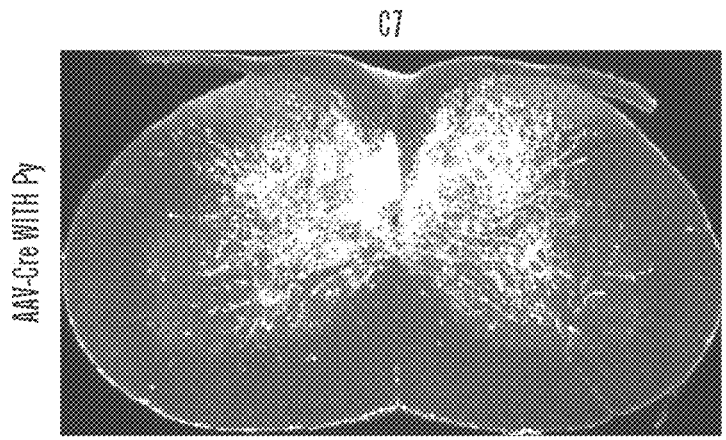
Figure 21D:
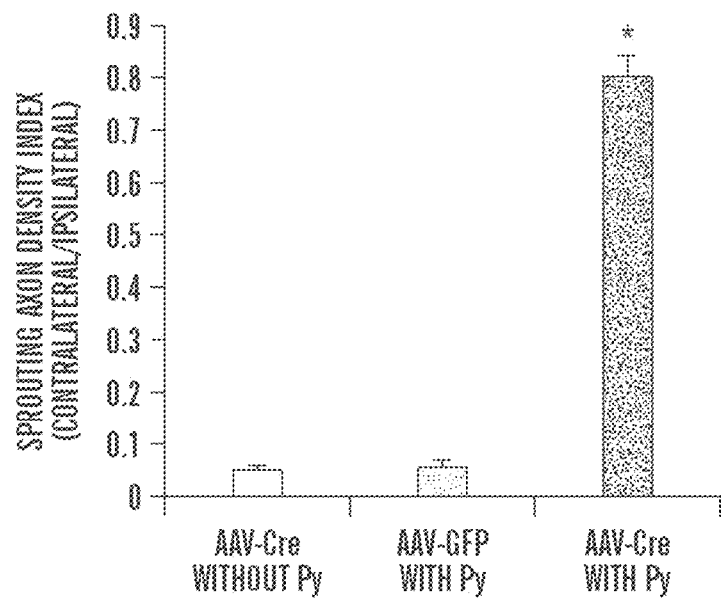
Figure 21E:
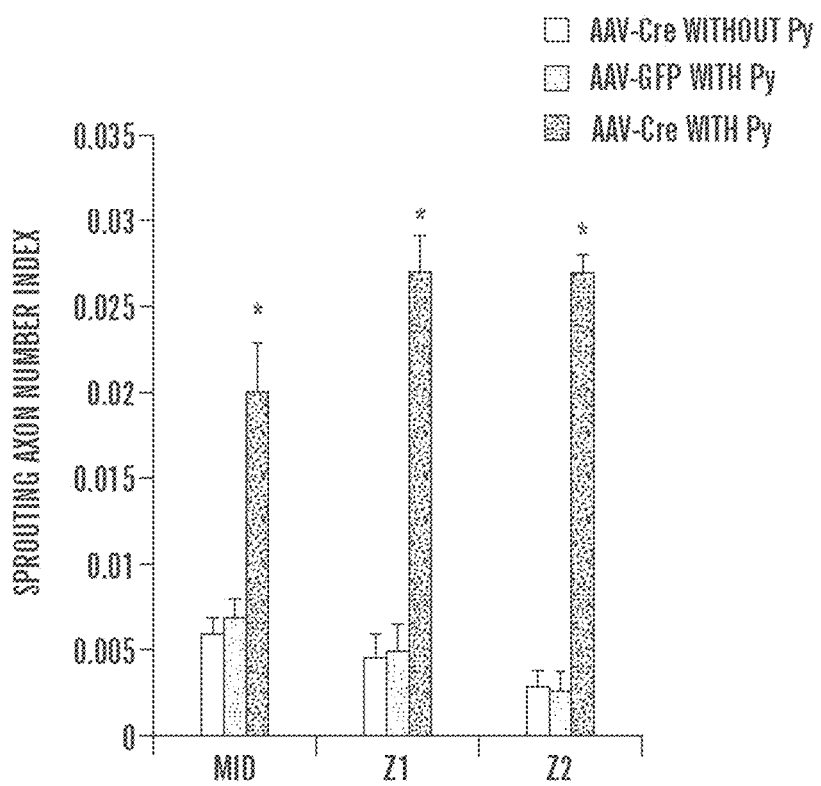

In intact PTEN and SOCS3 double-deleted mice without pyramidotomy, the CST projection pattern remains unaltered (FIG. 21A). However, after unilateral pyramidotomy, uninjured CST axons underwent a significantly increased sprouting response (FIG. 21C-21E, FIG. 26), compared with that seen in the single SOCS3-deleted (FIG. 18C) or single PTEN-deleted (Liu et al., 2010) mice. As shown in FIG. 21D, the number of sprouting axons observed in the double mutants is more than what was seen in the single mutants combined (see FIG. 18 and Liu et al., 2010) and is similar to what was seen after unilateral pyramidotomy performed at P7 (Liu et al., 2010). In these double mutants, sprouting axons innervated almost all of the gray matter on the right side of the spinal cord, although their overall distribution is similar to that seen in the single mutants. These results suggest that the increased intrinsic growth ability resulting from co-deletion of PTEN and SOCS3 greatly enhances corticospinal neuron sprouting after a unilateral pyramidotomy.

Discussion

This study demonstrates that the sprouting response of the CST is regulated by a SOCS3-dependent signaling pathway in that SOCS3 deletion in cortical neurons enhances the sprouting response after unilateral pyramidotomy. This appears to be initiated, at least in part, by CNTF expressed by those neurons on the side of the spinal cord that are deprived of CST inputs. Furthermore, co-deletion of SOCS3 and PTEN further enhances the sprouting of spared CST axons, allowing CST sprouts to occupy the entire empty field left by the injured half. Overall, this study reveals a powerful new strategy for promoting functional reinnervation after injury.

Sprouting-Triggering Cytokines

Mechanistically, an important question regards the nature of the signal(s) that leads to collateral growth from spared CST axons after injury. Previous studies suggest that the expression of many genes is changed in the denervated spinal cord after unilateral pyramidotomy (Bareyre et al., 2002) and in cortical neurons that undergo axonal sprouting (Li et al., 2010), but it is unclear whether these are the primary triggers for axonal sprouting or secondary to changes that occur during or after axonal reorganization. The results strongly suggested that CNTF and perhaps other cytokines could be an important class of triggers for CST collateral sprouting. Three lines of evidence support this notion: SOCS3 deletion in cortical neurons promotes CST sprouting after injury; this injury-induced sprouting is correlated with CNTF expression; and exogenously applied CNTF promotes sprouting in SOCS3-deleted neurons in the absence of an injury.

CNTF and other cytokines have been implicated in promoting neuronal survival and axonal growth in both PNS and CNS. In both dorsal root ganglion neurons (Bareyre et al., 2011) and retinal ganglion neurons (Smith et al., 2009, Sun et al., 2011) CNTF triggers axon regeneration, which is largely mediated by the transcription factor STAT3. The data presented herein indicate that similar mechanisms also mediate the CST sprouting after unilateral pyramidotomy. Interestingly, the sprouting triggered by CNTF injection is less pronounced than what is seen after injury, suggesting possible involvements of other cytokines.

Extrinsic and Intrinsic Control of CST Sprouting

The herein presented dramatically enhanced CST sprouting response from corticospinal neurons with a co-deletion of SOCS3 and PTEN indicates a functional interaction between these two signaling pathways. Because of the established role of SOCS3 as a negative regulator of cytokine-activated JAK/STAT pathway, the effects of SOCS3 deletion are likely triggered by extracellular cytokines such as CNTF. In this aspect, a recent study showed that STAT3 selectively regulates initiation but not later perpetuation of axonal growth in sensory neurons (Bareyre et al., 2011). On the other hand, PTEN deletion could act by enhancing neuronal mTOR activity, a likely determinant of neuronal intrinsic growth ability (Park et al., 2008, Liu et al., 2010). Without being bound by theory, it is thought that SOCS3 deletion primes the neuron for an enhanced response to CNTF, and PTEN deletion acts synergistically to further enhance the intrinsic growth response to injury-induced signals. In axotomized retinal ganglion neurons, co-deletion of SOCS3 and PTEN induces the expression of IGF-1 and Rheb, two positive regulators of the mTOR pathway, suggesting that a positive feedback mechanism might act to sustain mTOR activity in injured neurons (Sun et al., 2011). It would be interesting for the future studies to find out whether similar or different mechanisms are involved in the sprouting response of spared axons after unilateral pyramidotomy.

Denervated Neurons as a Source of Generating CNTF

Surprisingly, despite the inflammatory response associated with Wallerian degeneration of transected CST axons, inflammatory cells do not show CNTF up-regulation. Instead, it was found that after unilateral pyramidotomy, neurons in the denervated spinal cord generate such a sprout-promoting cytokine. Interestingly, CNTF-expressing neurons are concentrated, but not limited to the termination territory of CST axons, suggesting that these CNTF-expressing neurons might be either direct or indirect targets of CST axons in intact animals. It is conceivable that upon denervation these neurons might undergo electrophysiological and/or biochemical alterations that lead to the induction of cytokine expression. Further investigation of denervation-triggered cytokine up-regulation might reveal new insights into the mechanisms of activity-dependent structural reorganization.

In addition to spontaneous recovery from partial injury, axonal sprouting-mediated functional recovery also occurs after certain manipulations such as rehabilitation. For example, robotic-based training was shown to promote extensive reorganization of cortical projections at the brainstem and spinal cord levels, allowing paralyzed rats to regain voluntary locomotion (van den Brand et al., 2012). It will be important to assess the possible involvement of activity-induced cytokines in this and other types of functional recovery. These results provide new insights into designing combinatorial strategies for promoting functional recovery after injury.

Materials and Methods

Mice and Surgeries.

All experimental procedures were performed in compliance with animal protocols approved by the Institutional Animal Care and Use Committee at Children's Hospital, Boston. AAV, serotype 2, preparation was described previously (ref). For AAV injection., neonatal $Pten^{f/f}$, $SOCS3^{f/f}$ or $PTEN^{f/f}/SOCS3^{f/f}$ mice were anesthetized and injected with 2 µl of either $10^{12}$ GC/ml AAV-Cre stir AAV-GFP into four sites of the right sensorimotor cortex using a nanoliter injector attached to a fine glass pipette. Mice were then placed on a warming pad and returned to their mothers after regaining normal color and activity. In other sets of experiments, CamkII-Cre/$SOCS3^{f/f}$ mice were used.

For pyramidotomy, mice were anesthetized with ketamine/xylazine. The procedure is similar to that described previously (ref). Briefly, an incision was made at the left side of the trachea. Blunt dissection was performed to expose the skull base and a craniotomy in the occipital bone allowed for access to the medullary pyramids. The left pyramid was cut with a fine scalpel medially up to the basilar artery. The wound was dosed in layers with 6.0 sutures. The mice were placed on soft bedding on a warming blanket held at 37° C. until fully awake. We traced the intact CST 4 weeks later with BDA (see below). For CNTF injection into adult SOCS3 f/f mice with neonatal AAV-Cre cortical injection, a laminectomy was performed at C1 and 1 ul of CNTF (10 ug/ml, PeproTech, 450-13) was injected with a nanoliter injector into the ventral side of the dorsal column (0.5 mm deep). BDA tracing was performed 6 weeks later.

BDA Tracing.

To label CST axons by anterograde tracing, a total of 2.0 µl of BDA (10%, Invitrogen, D-1956) was injected into the right sensorimotor cortex at five sites (anterior-posterior coordinates from bregma in mm; 1.0, 0.5, 0, −0.5, −1.0, all at 1.0 mm lateral and at a depth of 0.5 mm). Mice were kept for an additional 2 weeks before being sacrificed.

Histology and Immunohistochemistry.

Mice were given a lethal dose of anesthesia and transcardially perfused with 4% paraformaldehyde. Brains and spinal cords were isolated and post-fixed in the same fixative overnight at 4° C. Tissues were cryoprotected via increasing concentrations of sucrose. After embedding into OCT compound, the samples were snap frozen in dry ice. Serial sections (25 µm) were collected and stored at −20° C. until processed. Coronal sections of the lower medulla were cut for counting BDA-labeled CST fibers. For assessing the extent of CST sprouting, serial sections at C7 and other levels of the spinal cords were cut in the transverse plane.

Immunostaining was performed following standard protocols. All antibodies were diluted in a solution consisting of 5% normal goat or donkey serum (NGS) and 1% Triton X-100 in phosphate-buffered saline (PBS). We used goat antibodies to CNTF (5 µg/ml, R&D Systems), rat antibodies to CD68 (1:200, Serotec), rabbit antibody to GFAP (1:200, Wako) and mouse antibody to NeuN (1:100, Millipore). Sections were incubated with primary antibodies overnight at 4° C. and washed three times for 10 min with PBS. Secondary antibodies (Biotin-conjugated donkey antibody to goat and Alexa 488-conjugated goat antibody to rabbit, rat and mouse) were then applied and incubated for 1 h at 20-25° C. For CNTF staining, Elite Avidin biotin Conjugate (ABC, Vector Lab) was applied, followed by ISA Cyanine 3 (perkin Elmer). To detect BDA-labeled fibers, BDA staining was performed by incubating the sections in PBS containing streptavidin-horseradish peroxidase. The remaining staining procedure was performed according to the protocol provided by ISA Cyanine 3 system (Perkin Elmer).

Axonal Counting and Quantifications.

For the groups of pyramidotomy, digital images of C7 or other levels of the spinal cord transverse sections were collected using a Nikon fluorescence microscope. Densitometry measurement on each side of the gray matter was taken using Metamorph software, after being subthresholded to the background and normalized by area. The outcome measure of the sprouting density index was the ratio of contralateral and ipsilateral counts.

To quantify the number of sprouting axons, the methods used in previous studies (Liu et al., 2010) were followed. Briefly, a horizontal line was drawn through the central canal and across the lateral rim of the gray matter. Three vertical lines were then drawn to divide the horizontal line into three equal parts, starting from the central canal to the lateral rim. Only fibers crossing the three lines were counted in each section. The results were presented after normalization with the number of counted CST fibers at the medulla level. At least three sections were counted for each mouse.

References for Example 3

1. Aisaka, A., Aimi, Y., Yasuhara, O., Tooyama, I., Kimura, H., Shimada, M. (1999). Two modes of corticospinal reinnervation occur close to spinal targets following unilateral lesion of the motor cortex in neonatal hamsters. Neuroscience. 90, 53-67.
2. Aoki, M., Fujito, Y., Satomi, H., Kurosawa, Y., Kasaba, T. (1986). The possible role of collateral sprouting in the functional restitution of corticospinal connections after spinal hemisection. Neurosci. Res. 3, 617-627.

3. Bareyre F M, Haudenschild B, Schwab M E. (2002). *Long-lasting sprouting and gene expression changes induced by the monoclonal antibody IN-1 in the adult spinal cord*. J Neurosci. 22, 7097-7110.
4. Bareyre, F. M., Kerschensteiner, M., Raineteau, O., Mettenleiter, T. C., Weinmann, O., Schwab, M. E. (2004). The injured spinal cord spontaneously forms a new intraspinal circuit in adult rats. Nat. Neurosci. 7, 269-277.
5. Bareyre, F. M., Garzorz, N., Lang, C., Misgeld, T., Büning, H., Kerschensteiner, M. (2011). *In vivo imaging reveals a phase-specific role of STAT3 during central and peripheral nervous system axon regeneration*. Proc Natl Acad Sci USA. 108, 6282-6287.
6. Cafferty W B, Strittmatter S M. (2006). *The Nogo-Nogo receptor pathway limits a spectrum of adult CNS axonal growth*. J Neurosci. 26, 12242-12250.
7. Croker, B. A., Mielke, L. A., Wormald, S., Metcalf, D., Kiu, H., Alexander, W. S., Hilton, D. J., and Roberts, A. W. (2008). Socs3 maintains the specificity of biological responses to cytokine signals during granulocyte and macrophage differentiation. Exp Hematol 36, 786-798.
8. Eidelberg, E., Walden, J. G., Nguyen, L. H. (1981). Locomotor control in macaque monkeys. Brain. 104, 647-663.
9. Florence, S. L., Taub, H. B., Kaas, J. H. (1998). Large-scale sprouting of cortical connections after peripheral injury in adult macaque monkeys. Science. 282, 1117-1121.
10. Goldstein, B., Little, J. W., Harris, R. M. (1997). Axonal sprouting following incomplete spinal cord injury: an experimental model. J. Spinal Cord Med. 20, 200-206.
11. Kaas, J. H. (1991). Plasticity of sensory and motor maps in adult mammals. Annu. Rev. Neurosci. 14, 137-167.
12. Kuang, R. Z., Kalil, K. (1990) Specificity of corticospinal axon arbors sprouting into denervated contralateral spinal cord. J. Comp. Neurol. 302, 461-472.
13. Li, S., Overman, J. J., Katsman, D., Kozlov, S. V., Donnelly, C. J., Twiss, J. L., Giger, R. J., Coppola, G., Geschwind, D. H., Carmichael, S. T. (2010). *An age-related sprouting transcriptome provides molecular control of axonal sprouting after stroke*. Nat Neurosci. 13, 1496-1504.
14. Liu, K., Lu, Y., Lee, J. K., Samara, R., Willenberg, R., Sears-Kraxberger, Tedeschi, A., Park, K. K., Connolly, L., Steward, O., Zheng, B., and He, Z. (2010). PTEN deletion enhances the regenerative ability of adult corticospinal neurons. Nature Neurosci. 13, 1075-1081.
15. Liu, K, Tedeschi, A, Park, K. K., He Z. (2011). *Neuronal intrinsic mechanisms of axon regeneration*. Annu Rev Neurosci. 34, 131-52.
16. Maier, I. C., and Schwab, M. E. (2006). Sprouting, regeneration and circuit formation in the injured spinal cord: factors and activity. Philos Trans R Soc Lond B Biol Sci. 361, 1611-1634.
17. Mori, H., Hanada, R., Hanada, T., Aki, D., Mashima, R., Nishinakamura, H., Torisu, T., Chien, K. R., Yasukawa, H., and Yoshimura, A. (2004). Socs3 deficiency in the brain elevates leptin sensitivity and confers resistance to diet-induced obesity. Nat Med 10, 739-743.
18. Nicholson, S. E., De Souza, D., Fabri, L. J., Corbin, J., Willson, T. A., Zhang, J. G., Silva, A., Asimakis, M., Farley, A., Nash, A. D., Metcalf, D., Hilton, D. J., Nicola, N. A., Baca, M. (2000). *Suppressor of cytokine signaling-3 preferentially binds to the SHP-2-binding site on the shared cytokine receptor subunit gp130*. Proc Natl Acad Sci USA. 97, 6493-6498.
19. Park, K. K., Liu, K., Hu, Y., Smith, P. D., Wang, C., Cai, B., Xu, B., Connolly, L., Kramvis, I., Sahin, M., and He, Z. (2008). Promoting axon regeneration in the adult CNS by modulation of the PTEN/mTOR pathway. Science 322, 963-966.
20. Rouiller, E. M., Liang, F. Y., Moret, V., Wiesendanger, M. (1991). Trajectory of redirected corticospinal axons after unilateral lesion of the sensorimotor cortex in neonatal rat; a *Phaseolus vulgaris*-leucoagglutinin (PHA-L) tracing study. Exp. Neurol. 114, 53-65.
21. Smith, P D, Sun, F., Park, K., Cai, B., Wang, C., Kuwako, K., Martinez-Carrasco, I., Connolly, L., and He, Z. (2009). SOCS3 deletion promotes optic nerve regeneration in vivo. Neuron 64, 617-623.
22. Sun, F., Park, K. K., Belin, S., Wang, D., Lu, T., Chen, G., Zhang, K., Yeung, C., Feng, G., Yankner, B. A., and He, Z. (2011). Sustained axon regeneration induced by co-deletion of PTEN and SOCS3. Nature 480, 372-375.
23. Tripathi, R. B., McTigue, D. M. (2008). *Chronically increased ciliary neurotrophic factor and fibroblast growth factor-2 expression after spinal contusion in rats*. J Comp Neurol. 510, 129-144.
24. van den Brand R, Heutschi J, Barraud Q, DiGiovanna J, Bartholdi K, Huerlimann M, Friedli L, Vollenweider I, Moraud E M, Duis S, Dominici N, Micera S, Musienko P, Courtine G. (2012). *Restoring voluntary control of locomotion after paralyzing spinal cord injury*. Science 336, 1182-1185.
25. Yu, H., Saura, C. A., Choi, S. Y., Sun, L. D., Yang, X., et al. (2001). APP processing and synaptic plasticity in Presenilin-1 conditional knockout mice. Neuron 31, 713-726.
26. Woolf, C. J., Shortland, P., Coggeshall, R. E. (1992). Peripheral nerve injury triggers central sprouting of myelinated afferents. Nature 355, 75-78.

What is claimed:

1. A method of treating a subject for a neuronal lesion, comprising:
administering to the subject a therapeutically effective amount of an inhibitor of phosphatase and tensin homolog (PTEN) and a therapeutically effective amount of an inhibitor of suppressor of cytokine signaling 3 (SOCS3), wherein administering results in contacting one or more target neurons of the subject with the inhibitor of PTEN and the inhibitor of SOCS3, to thereby promote sustained survival, sustained regeneration, sustained compensatory outgrowth, or a combination thereof in the target neurons.

2. The method of claim 1, wherein the subject is a human.

3. The method of claim 1, wherein the inhibitor of PTEN is selected from the group consisting of:
(a) potassium bisperoxo(bipyridine)oxovanadate (V) (bpV(bipy));
(b) dipotassium bisperoxo(5-hydroxypyridine-2-carboxyl)oxovanadate (V) (bpV(HOpic));
(c) potassium bisperoxo(1,10-phenanthroline)oxovanadate (V), (bpV(phen));
(d) dipotassium bisperoxo(picolinato)oxovanadate (V), (bpV(pic)); and
(e) combinations thereof.

4. The method of claim 1, wherein the inhibitor of SOCS3 is selected from the group consisting of SOCS3-specific hpRNA, siRNA, antisense SOCS3, dominant negative SOCS3, and combinations thereof.

5. The method of claim 1, wherein the neuronal lesion results from an acute injury.

6. The method of claim 1, wherein the acute injury is selected from the group consisting of crush, severing, and acute ischemia.

7. The method of claim 1 wherein administration first occurs within 24 hours of the injury.

8. The method of claim 1, wherein administration first occurs within 3 days of the injury.

9. The method of claim 1, wherein administration first occurs within 6 days of the injury.

10. The method of claim 1, wherein the neuronal lesion results from chronic neurodegeneration.

11. The method of claim 1, wherein the neuronal lesion results from a traumatic injury.

12. The method of claim 1, wherein the lesioned neuron is a sensory neuron.

13. The method of claim 1, wherein one or both inhibitors are administered intravenously.

14. The method of claim 1, wherein one or both inhibitors are administered locally at the target neuron.

* * * * *